(12) United States Patent
Savarese et al.

(10) Patent No.: US 9,220,700 B2
(45) Date of Patent: Dec. 29, 2015

(54) CYSTEINE FOR PHYSIOLOGICAL INJECTION

(75) Inventors: John J. Savarese, Southbury, CT (US); Paul M. Heerdt, Greenwich, CT (US)

(73) Assignee: Cornell University, Ithaca, NY (US)

(*) Notice: Subject to any disclaimer, the term of this patent is extended or adjusted under 35 U.S.C. 154(b) by 771 days.

(21) Appl. No.: 13/391,154

(22) PCT Filed: Aug. 18, 2010

(86) PCT No.: PCT/US2010/045907
§ 371 (c)(1),
(2), (4) Date: May 7, 2012

(87) PCT Pub. No.: WO2011/022491
PCT Pub. Date: Feb. 24, 2011

(65) Prior Publication Data
US 2012/0214873 A1 Aug. 23, 2012

Related U.S. Application Data

(60) Provisional application No. 61/235,191, filed on Aug. 19, 2009.

(30) Foreign Application Priority Data

Mar. 17, 2010 (WO) ................ PCT/US2010/000796

(51) Int. Cl.
*A61K 31/195* (2006.01)
*A61K 31/198* (2006.01)
*A61K 9/00* (2006.01)
*A61K 9/06* (2006.01)
(Continued)

(52) U.S. Cl.
CPC ............. *A61K 31/198* (2013.01); *A61K 9/0019* (2013.01); *A61K 9/06* (2013.01); *A61K 31/375* (2013.01); *A61K 47/22* (2013.01)

(58) Field of Classification Search
CPC .......................... A61K 31/195; A61K 31/198
USPC .......................................................... 514/562
See application file for complete search history.

(56) References Cited

U.S. PATENT DOCUMENTS 3,004,031 A 10/1961 Taylor et al.
4,036,959 A 7/1977 Green et al.
4,039,682 A 8/1977 Ausman et al.
(Continued)

FOREIGN PATENT DOCUMENTS

CN 101366695 A 2/2009
EP 0008824 A1 3/1980
(Continued)

OTHER PUBLICATIONS

"U.S. Appl. No. 13/257,214, Notice of Allowance mailed Jul. 19, 2013", 19 pgs.
(Continued)

*Primary Examiner* — San-Ming Hui
(74) *Attorney, Agent, or Firm* — Schwegman Lundberg & Woessner, P.A.

(57) ABSTRACT

This application describes methods of making and using physiological cysteine solutions useful for reversing a neuromuscular blockade caused by a cysteine-reversible neuromuscular blockade agent, that overcomes problems of cysteine precipitation and dimerization.

6 Claims, 5 Drawing Sheets

(51) Int. Cl.
*A61K 31/375* (2006.01)
*A61K 47/22* (2006.01)

(56) References Cited

U.S. PATENT DOCUMENTS

| | | | |
|---|---|---|---|
| 4,179,507 A | 12/1979 | Stenlake et al. | |
| 4,192,877 A | 3/1980 | Savarese et al. | |
| 4,235,906 A | 11/1980 | Savarese et al. | |
| 4,491,665 A | 1/1985 | El-Sayad et al. | |
| 4,556,712 A | 12/1985 | Rice | |
| 4,666,918 A | 5/1987 | Ivanova et al. | |
| 4,686,228 A | 8/1987 | Campbell et al. | |
| 4,701,460 A | 10/1987 | El-Sayad et al. | |
| 4,707,485 A | 11/1987 | Kaiser et al. | |
| 4,727,146 A | 2/1988 | Rice | |
| 4,727,147 A | 2/1988 | Wintermeyer et al. | |
| 4,761,418 A | 8/1988 | Swaringen, Jr. et al. | |
| 5,240,939 A | 8/1993 | Demko | |
| 5,438,140 A | 8/1995 | Oftring et al. | |
| 5,453,510 A | 9/1995 | Hill et al. | |
| 5,556,978 A | 9/1996 | Hill et al. | |
| 5,684,154 A | 11/1997 | Chamberlin | |
| 6,177,445 B1 | 1/2001 | Bigham et al. | |
| 6,187,789 B1 | 2/2001 | Bigham et al. | |
| 6,194,421 B1 | 2/2001 | Cohen et al. | |
| 6,548,521 B1 | 4/2003 | Cohen et al. | |
| 6,562,836 B1 | 5/2003 | Szarek et al. | |
| 6,838,270 B1* | 1/2005 | Kurosawa et al. | 435/189 |
| 6,858,750 B2 | 2/2005 | Joshi | |
| 7,037,489 B2 | 5/2006 | Uchiwa et al. | |
| 8,592,451 B2 | 11/2013 | Savarese et al. | |
| 2003/0149082 A1 | 8/2003 | Makriyaannis et al. | |
| 2003/0191115 A1 | 10/2003 | Pinto et al. | |
| 2004/0054001 A1 | 3/2004 | Joshi et al. | |
| 2004/0180925 A1 | 9/2004 | Matsuno et al. | |
| 2005/0192243 A1 | 9/2005 | Savarese | |
| 2006/0177408 A1 | 8/2006 | Uchiwa et al. | |
| 2006/0205659 A1 | 9/2006 | Joshi et al. | |
| 2008/0139482 A1 | 6/2008 | Savarese | |

FOREIGN PATENT DOCUMENTS

| | | |
|---|---|---|
| EP | 1380573 A2 | 1/2004 |
| EP | 1526130 A1 | 4/2005 |
| EP | 1676580 A1 | 7/2006 |
| JP | 54-055577 A | 5/1979 |
| JP | 61-087666 A | 5/1986 |
| JP | 5-017431 A | 1/1993 |
| WO | WO-98/42674 A1 | 10/1998 |
| WO | WO-98/42675 A1 | 10/1998 |
| WO | WO 98/47534 A1 | 10/1998 |
| WO | WO-2004/035869 A1 | 4/2004 |
| WO | WO-2005/041960 A2 | 5/2005 |
| WO | WO-2007/074454 A2 | 7/2007 |
| WO | WO-2008/070121 A1 | 6/2008 |
| WO | WO-2010/107488 A1 | 9/2010 |
| WO | WO-2011/022491 A1 | 2/2011 |

OTHER PUBLICATIONS

"U.S. Appl. No. 13/257,214, Response filed May 9, 2013 to Restriction Requirement mailed Apr. 24, 2013", 52 pgs.
"U.S. Appl. No. 13/257,214, Restriction Requirement mailed Apr. 24, 2013", 8 pgs.
"Chinese Application Serial No. 201080047362.6, Office Action mailed Sep. 9, 2013", (w/ English Translation), 15 pgs.
"Chinese Application Serial No. 201080047362.6, Response filed May 9, 2013 to Office Action mailed Dec. 25, 2012". (w/ English Translation of Amendments), 19 pgs.
"Chinese Application Serial No. 201080047362.6, Response filed Nov. 25, 2013 to Office Action mailed Sep. 9, 2013", 4 pgs.
"U.S. Appl. No. 11/951,114 Response filed Oct. 14, 2010 to Restriction Requirement mailed Jul. 16, 2010", 40 pgs.
"Australian Application Serial No. 2007328210, Response filed Oct. 22, 2012 to Office Action mailed Apr. 13, 2012", 15 pgs.
"Chinese Application Serial No. 201080047362.6, Office Action mailed Dec. 25, 2012", (w/ English Translation), 17 pgs.
"Indian Application Serial No. 2432/KOLNP/2009, Voluntary Amendment filed Nov. 22, 2010", 25 pgs.
"Japanese Application Serial No. 2009-540280, Office Action mailed Nov. 16, 2012", (w/ English Translation), 5 pgs.
"Japanese Application Serial No. 2009-540280, Response filed Jan. 30, 2013 to Office Action mailed Nov. 16, 2012", (w/ English Translation of Claims), 15 pgs.
"U.S. Appl. No. 10/975,197, Advisory Action mailed Jan. 24, 2007", 3 pgs.
"U.S. Appl. No. 10/975,197, Final Office Action mailed Oct. 18, 2007", 15 pgs.
"U.S. Appl. No. 10/975,197, Final Office Action mailed Sep. 26, 2006", 16 pgs.
"U.S. Appl. No. 10/975,197, Non-Final Office Action mailed Feb. 24, 2006", 9 pgs.
"U.S. Appl. No. 10/975,197, Non-Final Office Action mailed May 2, 2007", 13 pgs.
"U.S. Appl. No. 10/975,197, Response and Declaration filed Jul. 24, 2006 to Non-Final Office Action mailed Feb. 24, 2006", 23 pgs.
"U.S. Appl. No. 10/975,197, Response filed Jan. 13, 2006 to Restriction Requirement mailed Dec. 27, 2005", 10 pgs.
"U.S. Appl. No. 10/975,197, Response filed Jul. 30, 2007 to Non-Final Office Action mailed May 2, 2007", 17 pgs.
"U.S. Appl. No. 10/975,197, Response filed Oct. 30, 2007 to Final Office Action mailed Oct. 18, 2007", 17 pgs.
"U.S. Appl. No. 10/975,197, Response filed Dec. 22, 2006 to Final Office Action mailed Sep. 26, 2006", 13 pgs.
"U.S. Appl. No. 10/975,197, Restriction Requirement mailed Dec. 27, 2005", 5 pgs.
"U.S. Appl. No. 10/975,197, Non-Final Office Action mailed Feb. 4, 2008", 17 pgs.
"U.S. Appl. No. 11/951,114, Restriction Requirement mailed Jul. 16, 2010", 7 pgs.
"U.S. Appl. No. 11/951,114, Non Final Office Action mailed May 25, 2011", 7 pgs.
"U.S. Appl. No. 11/951,114, Non Final Office Action mailed Dec. 15, 2010", 6 pgs.
"U.S. Appl. No. 11/951,114, Notice of Allowance mailed Nov. 30, 2011", 9 pgs.
"U.S. Appl. No. 11/951,114, Preliminary Amendment filed Jan. 7, 2009", 16 pgs.
"U.S. Appl. No. 11/951,114, Response filed Mar. 15, 2011 to Non Final Office Action mailed Dec. 15, 2010", 12 pgs.
"U.S. Appl. No. 11/951,114, Response filed Sep. 26, 2011 to Non Final Office Action mailed May 25, 2011", 15 pgs.
"Canadian Application Serial No. 2,671,904, Office Action mailed Jun. 15, 2011", 3 pgs.
"Canadian Application Serial No. 2,671,904, Response filed Sep. 14, 2011 to Office Action mailed Jun. 23, 2011", 30 pgs.
"Chinese Application Serial No. 200780050532.4, Office Action mailed Sep. 20, 2010", (w/ English Translation), 10 pgs.
"Chinese Application Serial No. 200780050532.4, Response filed Feb. 5, 2011 to Office Action mailed Sep. 20, 2010", (w/ English Translation of Claims), 15 pgs.
"Chinese Application Serial No. 200780050532.4, Response filed Dec. 8, 2011 to Office Action mailed Sep. 26, 2011", (w/ English Translation of Claims), 22 pgs.
"Chinese Application Serial No. 200780050532.4, Second Office Action mailed Sep. 26, 2011", (w/ English Translation), 11 pgs.
"Database WPI Week 199309", *Thomson Scientific*, London, GB; AN 1993-071085, JP 5 017431 A (Seiko Epson Corp), (Jan. 26, 1993), 2 pgs.
"Database WPI Week 200923", *Thomson Scientific*, London, GB; AN 2009-G02209, CN 101366695 A (Jiangsu Sihuan Biological Co Ltd), (Feb. 18, 2009), 2 pgs.
"European Application Serial No. 07862551.4, Response filed Jun. 2, 2011 to Office Action dated Nov. 25, 2010", 9 pgs.
"European Application Serial No. 07862551.4, Supplemental European Search Report mailed Oct. 29, 2010", 7 pgs.

(56) References Cited

OTHER PUBLICATIONS

"International Application Serial No. PCT/US07/24914, International Search Report mailed Apr. 17, 2008", 3 pgs.
"International Application Serial No. PCT/US07/24914, Written Opinion mailed Apr. 17, 2008", 8 pgs.
"International Application Serial No. PCT/US2004/035869, International Preliminary Report on Patentability and Written Opinion mailed May 11, 2006", 9 pgs.
"International Application Serial No. PCT/US2004/035869, International Search Report mailed May 3, 2005", 3 pgs.
"International Application Serial No. PCT/US2010/000796, International Preliminary Report on Patentability mailed Sep. 29, 2011", 12 pgs.
"International Application Serial No. PCT/US2010/000796, International Search Report mailed Aug. 4, 2010", 2 pgs.
"International Application Serial No. PCT/US2010/000796, Written Opinion mailed Aug. 4, 2010", 13 pgs.
"International Application Serial No. PCT/US2010/045907, International Search Report mailed Nov. 10, 2010", 4 pgs.
"International Application Serial No. PCT/US2010/045907, Written Opinion mailed Nov. 10, 2010", 8 pgs.
"Le Chatelier's Principle", © Jim Clark 2002. Retrieved from the Internet: <URL: http://www.chemguide.co.uk/physical/equilibria/lechatelier.html>, (2002), 6 pgs.
"Rate equation",2006 Wikipedia® [online]. Retrieved from the Internet: <URL:http://en.wikipedia.org/wiki/rRate_equation>, *From Wikipedia®, Free Encyclopedia*, (2006), 6 pgs.
Agoston, S., et al., "The Neuromuscular Blocking Action of Org NC 45, A New Pancuronium Derivative, in Anaesthetized Patients", *British Journal of Anaesthesia*, 52(Supplement 1), (1980), 53S-59S.
Baird, W. L. M., et al., "A New Neuromuscular Blocking Drug, Org NC 45", *British Journal of Anaesthesia*, 52(Supplement 1), (1980), 61S-62S.
Bedford, R. F., "From the FDA", *Anesthesiology*, 82, (1995), p. 33A.
Belmont, M. R., "Succinylcholine/Suxamethonium", *Current Opinion in Anaesthesiology*, 8, (1995), 362-366.
Bencini, A., et al., "Use of the Human "Isolated Arm" Preparation to Indicate Qualitative Aspects of a New Neuromuscular Blocking Agent, Org NC 45", *British Journal of Anaesthesia*, 52(Supplement 1), (1980), 43S-47S.
Bevan, D. R., "Newer Neuromuscular Blocking Agents", *Pharmacology & Toxicology*, 74(1), (1994), 3-9.
Boros, E. E., et al., "Neuromuscular Blocking Activity and Therapeutic Potential of Mixed-Tetrahydroisoquinolinium Halofumarates and Halosuccinates in Rhesus Monkeys", *Journal of Medicinal Chemistry*, 46, (2003), 2502-2515.
Boros, E. E, et al., "Bis- and mixed-tetrahydroisoquinolinium chlorofumarates: New ultra-short-acting nondepolarizing neuromuscular blockers", *Journal of Medicinal Chemistry*, 42(2), (1999), 206-209.
Boros, E. E., "Neuromuscular Blocking Activity and Therapeutic Potential of Mixed-Tetrahydroisoquinolinium Halofumarates and Halosuccinates in Rhesus Monkeys", *Journal of Medicinal Chemistry*, 46, (Jun. 2003), 2502-2515.
Buckett, W. R., et al., "Pancuronium Bromide and Other Steroidal Neuromuscular Blocking Agents Containing Acetylcholine Fragments", *Journal of Medicinal Chemistry*, 16(10), (1973), 1116-1124.
Buzello, W., "The New Non-Depolarizing Muscle Relaxant Org NC 45 in Clinical Anaesthesia: Preliminary Results", *British Journal of Anaesthesia*, 52 (Supplement 1), (1980), 62S-64S.
Crul, J. F., et al., "First Clinical Experiences With Org NC 45", *British Journal of Anaesthesia*, 52(Supplement 1), (1980), 49S-52S.
De Rosa, S. C, "N-acetylcysteine Replenishes Glutathione in HIV Infection", *European Journal of Clinical Investigation*, 30, (2000), 915-929.
Dizdar, N., et al., "Comparison of N-acetylcysteine and i-2-oxothiazolidne-4-carboxylate as cysteine deliverers and glutathione Precursors in Human Malignant Melanoma Transplants in Mice", *Cancer Chemother Pharmacol*, 45, (2000), 192-198.

Durant, N. N., et al., "Suxamethonium", *British Journal of Anaesthology*, 54, (1982), 195-208.
Fahey, M. R., et al., "Clinical Pharmacology of ORG NC45 (Norcuron TM): A New Nondepolarizing Muscle Relaxant", *Anesthesiology*, 55(1), (1981), 6-11.
Foldes, F. F., et al., "Influence of Halothane and Enflurane on the Neuromuscular Effects of Org NC 45 in Man", *British Journal of Anaesthesia*, 52(Supplement 1), (1980), 64S-65S.
Huang, T. C., et al., "Mechanistic Studies on Thiazolidine Formation in Aldehyde/Cysteamine Model Systems", *J Agric Food Chem.*, 46(1), (Jan. 1998), 224-227.
Kharkevich, D. A., "New Curare-Like Agents", *J. Pharm. Pharmac.*, 26, (1974), 153-165.
Khromov-Borisov, N. V., et al., "Removal of a Curare-Like Effect by Direct Inactivation of the Myorelaxant Molecule by Disruption of the Disulfide Bond", Doklady Biological Sciences, *Proceedings of the Academy of Sciences of the USSR*, 186(1), (1968), 460-463.
Kreig N., et al., "Preliminary Review of the Interactions of Org NC 45 With Anaesthetics and Antibiotics in Animals", *British Journal of Anaesthesia*, 52(Supplement 1), (1980), 33S-36S.
Kulawaska, et al., "Kinetics of the esterification of maleic anhydride with octyl, decyl or dodecyl 68-69 alcohol over dowex catalyst", (Abstract Only), *Reaction Kinetics and Catalysis Letters*, 85(1), (2005),51-56.
Lee, C., "Structure, Conformation, and Action of Neuromuscular Blocking Drugs", *British Journal of Anaesthesia*, 87(5), (2001), 755-769.
Li, J., et al., "Dietary supplementation with cysteine prodrugs selectively restores tissue glutathione levels and redox status in protein-malnourished mice", *Journal of Nutritional Biochemistry*,13, (2002), 625-633.
Lien, C. A, "The Pharmacology of GW280430A: A New Nondepolarizing Neuromuscular Blocking Agent", *Seminars in Anesthesia: Perioperative Medicine and Pain*, 21(2), (Jun. 2002), 86-91.
Mahajan, R. P., "Focus on: Controversies in Anaesthesia—Is Suxamethonium Now Obsolete?", *Current Anaesthesia and Critical Care*, 7, (1996), 289-294.
Marshall, I. G., et al., "Pharmacology of Org NC 45 Compared With Other Non-Depolarizing Neuromuscular Blocking Drugs", *British Journal of Anaesthesia*, 52(Supplement 1), (1980), 11S-19S.
Marshall, R. J., et al., "Comparison of the Cardiovascular Actions of Org NC 45 With Those Produced by Other Non-Depolarizing Neuromuscular Blocking Agents in Experimental Animals", *British Journal of Anaesthesia*, 52(Supplement 1), (1980), 21S-32S.
McNulty, M., "The Ultra-Short Acting Nondepolarizing Relaxant GW280430A Undergoes Rapid Degradation by Chemical Mechanisms", *Anesthesiology Abstracts of Scientific Papers Annual Meeting*—2002, (2002). 1 pg.
Miller, R. D., "Org NC 45", *British Journal of Anaesthesia*, 52(Supplement 1), (1980), 71S-72S.
Morrison, R. T., et al., *In: Organic Chemistry* (Second Edition), Allyn and Bacon, Inc., Boston, MA, (1966), 290-293.
Murphy, G.S., "Residual neuromuscular blockade:incidence, assessment, and relevance in the postoperative period", *Minerva Anestesiol*, vol. 72(3), (2006), 97-109.
Naguib, M., et al., "Advances in Neurobiology of the Neuromuscular Junction", *Anesthesiology*, 96(1), (2002), 202-231.
Nebergall, W. H., "Chapter 7—Molecular Structure and Hybridization", *in: General Chemistry* (6th Edition), D. C. Heath and Company, (1980), 149-152.
Norman, J., et al., "Introduction", *British Journal of Anaesthesia*, 52(Supplement 1), (1980), S1-S2.
Rees, D. C., et al., "Chapter 5. Drugs in Anesthetic Practice", *Annual Reports in Medicinal Chemistry* , 31, (1994), 41-50.
Reese, M J, "Comparative Metabolic Profiles of the Neuromuscular Blocker GW280430 in Human, Monkey, and Dog, and Characterization of a Major Metabolite as an Unusal Cyclized Cysteine conjugate", (Abstract 282), Presented at the *9th North American ISSX Meeting* (issx.org); Nashville, TN, (Oct. 1999), p. 142.
Saitoh, Y., et al., "Infusion of Amino Acid Enriched Solution Hastens Recovery From Neuromuscular Block Caused by Vecuronium", *British Journal of Anaesthesia*, 86, (2001), 814-821.

(56) References Cited

OTHER PUBLICATIONS

Sakuraba, H., et al., "Asymmetric Michael Addition of Aromatic Thiols to 2-Cyclohexenone and Maleic Acid Esters Via Formation of Crysatiline Cyclodextrin Complexes", *Journal of Inclusion Phenomena and Molecular Recognition in Chemistry*, (1991), 195-204.

Savage, D. S., et al., "The Emergence of ORG NC 45, 1-[(2beta,3alpha,16beta,17beta)-3, 17-Bis(Acetyloxy)-2-(1-Piperidinyl)-Androstan-16-YL]-1-Methylpiperidinium Bromide, From the Pancuronium Series", *British Journal of Anaesthesia*, 52(*Supplement* 1), (1980), 3S-9S.

Savarese, J. J., et al., "Chapter 14. Pharmacology of Muscle Relaxants and Their Antagonists", *in: Anesthesia*, vol. 1, (Fourth Edition), Miller, R. D., et al., Editors, Churchill Livingstone Inc., (1994), 417-487.

Savarese, J. J, et al., "Rapid chemical antagonism of neuromuscular blockade by L-cysteine adduction to and inactivation of the olefinic (double-bonded) isoquinolinium diester compounds gantacurium (AV430A), CW 002, and CW 011.", *Anesthesiology*, 113(1), (Jul. 2010), 58-73.

Schaer, H., et al., "Preliminary Clinical Observations With Org NC 45", British Journal of *Anaesthesia*, 52(*Supplement* 1), (1980), 65S-67S.

Son, S. L., et al., "A Comparison of the Neuromuscular Blocking and Vagolytic Effects of ORG NC45 and Pancuronium", *Anesthesiology*, 55(1), (1981), 12-18.

Speight, T. M., et al., "Pancuronium Bromide: A Review of its Pharmacological Properties and Clinical Application", *Drugs*, 4(1-2), 163-226.

Sunaga, H., et al., "Cysteine reversal of the novel neuromuscular blocking drug CW002 in dogs: pharmacodynamics, acute cardiovascular effects, and preliminary toxicology", *Anesthesiology*, 112(4), (Apr. 2010), 900-909.

Van Der Veen, F., et al., "Pharmacokinetics and Pharmacodynamics of Org NC 45 in Man", *British Journal of Anaesthesia*, 52(*Supplement* 1), (1980), 37S-41S.

Viby-Mogensen, J., et al., "On Org NC 45 and Halothane Anaesthesia", *British Journal of Anaesthesia*, 52(*Supplement* 1), (1980), 67S-69S.

Zhang, L., et al., "Thiazolidine formation as a general and site-specific conjugation method for synthetic peptides and proteins", *Anal Biochem.*, 233(1), (Jan. 1, 1996), 87-93.

\* cited by examiner

CYSTEINE FOR PHYSIOLOGICAL INJECTION

This application is a U.S. National Stage Filing under 35 U.S.C. 371 from International Application No. PCT/US2010/045907, filed Aug. 18, 2010, and published as WO 2011/022491 A1 on Feb. 24, 2011, which application claims priority to U.S. Provisional Patent Application Ser. No. 61/235,191, filed Aug. 19, 2009 and to PCT Application Ser. No. PCT/US2010/000796, filed Mar. 17, 2010, the contents of each of which applications and publication are specifically incorporated herein by reference in their entireties.

This application is also related to U.S. Ser. No. 11/951,114, filed Dec. 5, 2007; U.S. application Ser. No. 10/975,197, filed Oct. 28, 2004; PCT Application Ser. No. PCT/US2004/035869, filed Oct. 28, 2004; U.S. Application Ser. No. 60/515,048, filed Oct. 28, 2004; and U.S. Provisional Application Ser. No. 61/160,915, filed Mar. 19, 2009, the contents of each of which applications are specifically incorporated herein by reference in their entireties.

BACKGROUND OF THE INVENTION

During certain surgical procedures, neuromuscular blocking agents must be employed. However, neuromuscular blocking agents literally paralyze a patient for the time during which they are active. Hence, the use of neuromuscular blocking agents is restricted to situations where muscle relaxation is essential for effective treatment of a patient, for example, selected surgical procedures involving intubation of the trachea. Because paralysis can interfere with essential body functions (e.g. breathing) the physician selects a neuromuscular blocking agent that will be active for as long as needed but no more than is needed. For example, when a breathing tube must be inserted into the trachea of a patient, a neuromuscular blocking agent is used to relax the tracheal muscles and permit intubation. However, the neuromuscular blocking agent also relaxes the muscles of the chest, thereby causing the patient to stop breathing. The anesthesiologist must quickly insert the breathing tube into the patient's trachea and begin ventilation of the lungs. If the tube cannot be inserted quickly enough, the physician must intervene with some form of artificial resuscitation or the patient may suffer oxygen deprivation, and the associated tissue and brain damage that may result from lack of oxygen. Fast reversal of the neuromuscular blocking agent by a rapidly acting antagonist can remove the patient from danger and avoid, or minimize, the duration of artificial resuscitation.

The inventors have developed neuromuscular blocking agents that, surprisingly, are quickly reversed by injection of a thiol such as the amino acid, cysteine. However, physiological cysteine solutions at useful concentrations are unstable and easily oxidize or dimerize.

SUMMARY OF THE INVENTION

Thus, one aspect of the invention is a method of making a cysteine solution for physiological administration that includes:
(a) obtaining an aqueous solution of cysteine with a pH of about 1.80 to about 2.20; and
(b) mixing the aqueous solution of cysteine with a buffering solution to generate a cysteine solution for physiological administration that has a pH of about 4.5 to about 5.5, wherein oxygen is substantially removed from the aqueous solution of cysteine, the buffering solution and/or cysteine solution for physiological administration.

In some embodiments, the aqueous solution of cysteine has a pH of about 1.90 to about 2.00. The aqueous solution of cysteine can be made from physiologically acceptable solvents, for example, water, physiological saline, sugar solutions and combinations thereof.

As used herein, the term "cysteine" includes both L-cysteine and D-cysteine, or any mixture thereof, e.g., a racemate, unless other specified. As described below, use of the L- or D-isomer of cysteine can be beneficial in certain situations. For example, L-cysteine is typically cheaper and more readily available. However, when administering large amounts of cysteine, the D-isomer of cysteine may be preferred because it is also active and tends to minimize side effects (e.g., adverse cardiovascular effects).

The buffering solution used solution to generate a cysteine solution for physiological administration can include a weak base. Examples of compounds that can be present in the buffering solution include tris(hydroxymethyl)methylamine (Tris), N,N-bis(2-hydroxyethyl)glycine (Bicine), N-tris(hydroxymethyl)methylglycine (Tricine), 4-2-hydroxyethyl-1-piperazineethanesulfonate (HEPES), {[tris(hydroxymethyl)methyl]amino}ethanesulfonate (TES),3-(N-morpholino)propanesulfonate (MOPS), piperazine-N,N'-bis(2-ethanesulfonate (PIPES),2-(N-morpholino)ethanesulfonate (MES) or combinations thereof.

As described herein, cysteine solutions with more than 50 mg/ml cysteine are difficult to make, however the cysteine solution for physiological administration described herein can have a cysteine concentration of about 100 to about 300 mg/ml, or about 150-250 mg/ml.

The aqueous solution of cysteine and/or the stable solution of cysteine can include other ingredients, for example, glutathione. When glutathione is present it can be included at a concentration of 100 to 200 mg/ml. Mixtures of L-cysteine and D-cysteine can also be included in the aqueous solution of cysteine and/or the stable solution of cysteine. Other ingredients that can be included in the aqueous solution of cysteine and/or the stable solution of cysteine are, for example, a bacteriostatic agent, a chelating agent, an antioxidant or a combination thereof. Examples of antioxidants that can be present in the aqueous solutions of cysteine and/or the stable solutions of cysteine include vitamins, cofactors and combinations thereof. For example, the antioxidant can be ascorbic acid, vitamin A, vitamin E, coenzyme Q10, a flavonoid and/or combinations thereof. Examples of chelating agents that can be present in the aqueous solutions of cysteine and/or the stable solutions of cysteine include citric acid, dicarboxymethyl-glutamic acid, ethylenediaminedisuccinic acid (EDDS), ethylenediaminetetraacetic acid (EDTA), hepta sodium salt of diethylene triamine penta (methylene phosphonic acid) (DTPMP.Na$_7$), malic acid, nitrilotriacetic acid (NTA), methionine, oxalic acid, phosphoric acid, polar amino acids (e.g., arginine, asparagine, aspartic acid, glutamic acid, glutamine, lysine, and ornithine), siderophores (e.g., Desferrioxamine B), succinic acid and combinations thereof.

Another aspect of the invention is a method of making a stable cysteine solution that can be stored prior to physiological administration, where the method involves:
(a) removing oxygen from a volume of physiological saline or water;
(b) adding sufficient cysteine to the physiological saline or water to generate a 150-250 mg/ml cysteine solution;

(c) adjusting the pH of the 150-250 mg/ml cysteine solution to a pH of about 1.90 to about 2.00 to generate a cysteine solution with a pH of about 1.90 to about 2.00;

(d) sparging the cysteine solution with the pH of about 1.90 to about 2.00 with non-oxygen containing gas to generate a deoxygenated cysteine solution; and (e) dispensing the deoxygenated cysteine solution into a container and sealing the container, to thereby make the stable cysteine solution that can be stored prior to physiological administration.

Such a stable cysteine solution, for example, can be stored for up to about 1 year without significant precipitation or dimerization of the cysteine. In some embodiments, the stable cysteine is stored frozen.

When administration of the cysteine is desired, the stable cysteine solution can be adjusted to a pH to about 4.4 to about 5.5, to thereby generate a physiological solution of cysteine. Thus, to adjust the pH of the stable cysteine solution, the following steps can be followed:

f) adding a buffering solution to the stable cysteine solution to adjust the pH to about 4.4 to about 5.5 without exposing the stable cysteine solution to significant oxygen;

g) mixing the buffering solution into the stable cysteine solution to generate a cysteine solution for physiological administration that has a pH of about 4.5 to about 5.5, wherein the mixing is performed without substantial exposure of the stable cysteine solution or the buffering solution to oxygen.

In many embodiments, it is advisable to substantially remove oxygen from the buffering solution before adding the buffering solution to the stable cysteine solution.

Another aspect of the invention is a kit that includes:

(a) a first container with a stable solution of cysteine that has a pH of about 1.8 to about 2.1;

(b) a second container with a buffering solution for raising the pH of the stable solution of cysteine; and (c) instructions for storing the kit, for raising the pH of the stable solution of cysteine to an appropriate pH and/or for administering the physiological solution of cysteine to reverse a neuromuscular blockade.

The kit can also include other components. For example, the kit can include one or more syringes and needles for transferring an appropriate amount of the buffering solution to the stable solution of cysteine and/or administering the physiological solution of cysteine to a patient. Moreover, the kit can also include a third container that contains a neuromuscular blocking agent, wherein a neuromuscular blockade generated in a subject by the neuromuscular blocking agent can be reversed by cysteine. In many embodiments, it is advisable to substantially remove oxygen from the first container and/or the second container. The stable solution of cysteine can be made by any of the methods and procedures described herein.

Another aspect of the invention is a method of reversing a neuromuscular blockade in a patient comprising administering an effective amount of a physiological solution of cysteine to the patient, wherein the physiological solution of cysteine is made by a method comprising:

(a) removing oxygen from a volume of physiological saline or water;

(b) adding sufficient cysteine to the physiological saline or water to generate a 150-250 mg/ml cysteine solution;

(c) adjusting the pH of the 150-250 mg/ml cysteine solution to a pH of about 1.90 to about 2.00 to generate a cysteine solution with a pH of about 1.90 to about 2.00;

(d) sparging the cysteine solution with the pH of about 1.90 to about 2.00 with non-oxygen containing gas to generate a deoxygenated cysteine solution;

(e) dispensing the deoxygenated cysteine solution into a container and sealing the container to thereby make the stable cysteine solution that can be stored prior to physiological administration;

(f) adding a buffering solution to the stable cysteine solution to adjust the pH to about 4.4 to about 5.5 without exposing the stable cysteine solution to significant oxygen; and (g) mixing the buffering solution into the stable cysteine solution to generate a physiological solution of cysteine that has a pH of about 4.5 to about 5.5, wherein the mixing is performed without substantial exposure of the stable cysteine solution or the buffering solution to oxygen.

In many embodiments, it is advisable to substantially remove oxygen from the buffering solution.

DESCRIPTION OF THE FIGURES

FIG. 5A) and heart rate (HR; FIG. 5B) responses to both D and L-cysteine in the same animals. Tracings represent the composite of 5 second averages for each animal beginning at the time of cysteine injection. Numerical data (mean±standard error) for variables at the time of injection (baseline) and peak response are shown, with the p value for the comparison.

DETAILED DESCRIPTION OF THE INVENTION

Definitions

Figure 1:
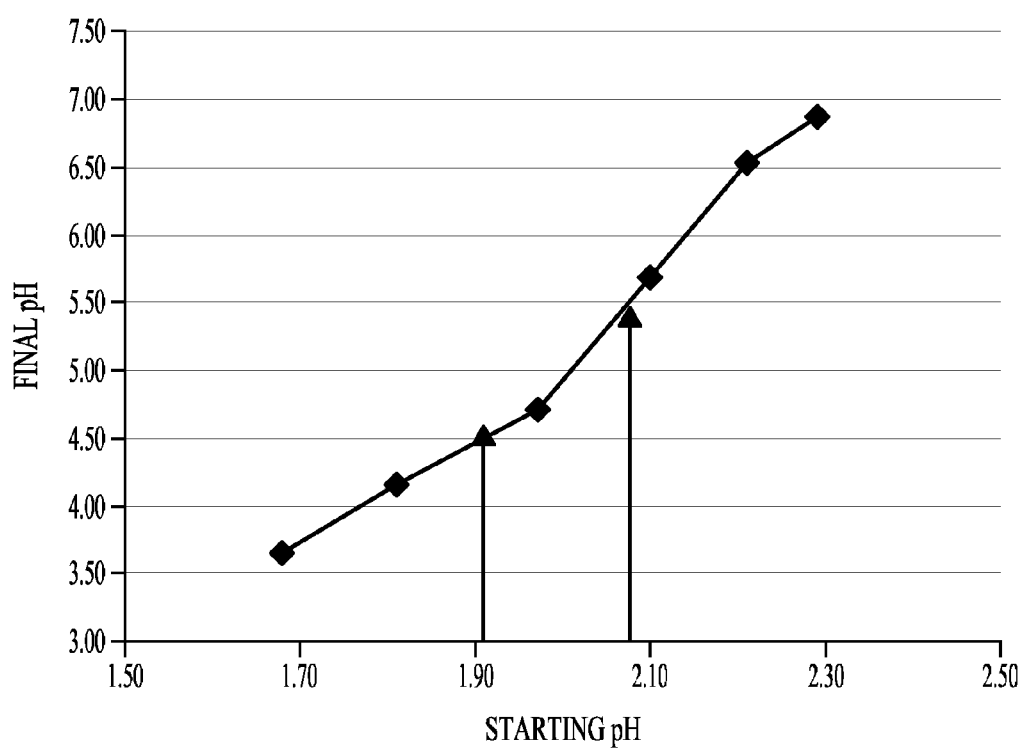
FIG. 1 graphically illustrates the final pH of L-Cys-HCl pH 1.95 Solutions after mixing with 1.0 mL 3.6M Tris pH 8.0, for cysteine sample WFJ-00017.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

All structures encompassed within a claim are "chemically feasible", by which is meant that the structure depicted by any combination or subcombination of optional substituents meant to be recited by the claim is physically capable of existence with at least some stability as can be determined by the laws of structural chemistry and by experimentation. Structures that are not chemically feasible are not within a claimed set of compounds.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SW, SOW, SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', N(R')C(=NR)N(R')$_2$, C(=NH)N(R')$_2$, N(R')C(=NH)N(R')$_2$, C(O)N(OR')R', or C(=NOR')R' wherein R' can be hydrogen or a carbon-based moiety, and wherein the carbon-based moiety can itself be further substituted. Further, any substituent can be bonded to a carbon or other atom by a linker, such as (CH$_2$)$_n$ or (CR'$_2$)$_n$ wherein n is 1, 2, 3, or more, and each R' is independently selected.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring systems such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S," or "[variable] is O, S . . . " are used, they are understood to encompass all of the sulfide, sulfoxide and sulfone oxidation states of sulfur.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

Cycloalkyl groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH3), —CH=C(CH3)2, —C(CH3)=CH2, —C(CH3)=CH(CH3), —C(CH2CH3)=CH2, cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C (CH$_2$CH$_3$), —CH$_2$C≡CH, —CH$_2$C≡C(CH$_3$), and —CH$_2$C≡C(CH$_2$CH$_3$), among others.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. The aryl moiety or the alkyl moiety or both are optionally substituted with other groups, including but not limited to alkyl, halo, amino, hydroxy, cyano, carboxy, nitro, thio, or alkoxy groups. Aralkenyl group are alkenyl groups as defined above in which a hydrogen or carbon bond of an alkyl group is replaced with a bond to an aryl group as defined above.

Heterocyclyl groups include aromatic and non-aromatic ring compounds containing 3 or more ring members, of which one or more is a heteroatom such as, but not limited to, N, O, S, or P. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

The term "amine" (or "amino"), where referring to a compound, includes primary, secondary, tertiary amines and quaternary ammonium salts, and to molecules containing one or more amino groups. When referring to a substituent group, the terms include functional groups having a basic nitrogen in free, salt, or quaternarized form, e.g., the formula —NR$_2$ or —NR$_3^+$ wherein each R can independently be hydrogen, alkyl, aryl, heterocyclyl, and the like. Amino groups include, but are not limited to, —NH$_2$, alkylamino, dialkylamino, arylamino, alkylarylamino, diarylamino, aralkylamino, and heterocyclylamino groups and the like. Quarternary ammonium salts are amine or amino groups within the meaning herein, for example a trimethylammonium group bonded to a carbon moiety is an amino group. Thus, trimethylammonium hydrochloride and tetramethylammonium chloride are both ammonium ions, and amines, within the meaning herein.

The term "amide" ("carboxamido" or "amido") includes C- and N-amide groups, i.e., —C(O)NR$_2$, and —NRC(O)R groups, respectively. Amide groups therefore include but are not limited to primary amido groups (—C(O)NH$_2$) and formamido groups (—NHC(O)H).

The term "urethane" (or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$).

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

"Halo," "halogen," and "halide" include fluorine, chlorine, bromine and iodine.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

In various embodiments, the compound or set of compounds, either per se or as are used in practice of embodiments of the inventive methods, can be any one of any of the combinations and/or sub-combinations of the various embodiments recited.

Detailed Description

Cysteine has been shown to rapidly antagonize a neuromuscular blockade induced by nondepolarizing neuromuscular blocking drugs, for example, isoquinolinium diesters of fumaric, maleic, and chlorofumaric acids. To accomplish the reversal of a neuromuscular blockade generated by one of these agents, cysteine is administered by intravenous injection. However, the natural pH of cysteine hydrochloride solutions at concentrations of 50 mg/ml or more in aqueous solution (e.g., 0.9% saline) is very low, ranging from about pH 0.8 to about pH 1.0. Moreover, cysteine is not soluble at concentrations greater than 50 mg/ml in its base form, but higher concentrations of cysteine are more conveniently administered for reversal of neuromuscular blockades. For example, bolus administration of volumes greater than 50 ml over a time period of 5-10 sec is generally not convenient in an operating room. Therefore, to be administered to patients, cysteine solutions have been developed that have higher concentrations and higher pH values as described herein.

In general, cysteine solutions for use as a neuromuscular blockade reversal agent in clinical practice have some or all of the following general properties:

1. A physiological solution with about 150-300 mg/ml (or 150-250 mg/ml) cysteine;
2. A pH of the solution of 4.0-5.0 to prevent venous irritation and/or trauma; and/or
3. Antioxidant additives to prevent formation of the cysteine dimer, cystine, which is inactive and insoluble.

According to the invention, cysteine solutions with these properties are stable, nonirritating and appropriate for bolus injection in an operating room scenario.

In general, cysteine dosages in humans for reversal of neuromuscular blockades are about 10-100 mg/kg or about 30-50 mg/kg. Thus, the typical dosages and volumes of cysteine to be injected will likely be in the range of about 1000-10000 mg or about 2000-5000 mg of cysteine (based on body weights of 70-100 kg).

Thus, compositions and methods have been developed to provide these amounts of cysteine in convenient volumes of about 5 ml to about 50 ml or about 10 ml to about 25 ml. Such compositions can be administered quickly, for example, as a single bolus intravenous injection over a period of time of about 2 seconds to about 60 seconds, or about 5 seconds to about 10 seconds. The solutions described herein have concentrations of cysteine that are about 100-300 mg/ml or about 180-250 mg/ml cysteine so that appropriate in vivo concentrations of cysteine are achieved after administration to quickly reverse a neuromuscular blockade.

Either the L-isomer or the D-isomer of cysteine can be used in the cysteine solutions provided herein, or a combination of L-cysteine and D-cysteine can be employed, e.g., the racemic form L-cysteine is produced endogenously and crosses the blood-brain barrier largely via a specific amino acid transporter. Thus, L-cysteine may contribute to central nervous stimulation following administration of large doses (e.g., 100 mg/kg or more). In contrast, the D-isomer of cysteine is not normally found in substantial quantities within the body, and is not a substrate for metabolic processes involving L-cysteine such as glutathione synthesis. In addition, D-cysteine is not a major substrate for the amino acid transporters which are L-isomer specific. As illustrated herein, D-cysteine can effectively reverse a neuromuscular blockade by neuromuscular blocking agent. Moreover, at 100 mg/kg, D-cysteine elicits less of a rise in mean arterial pressure than L-cysteine, consistent with the probability of less entry into the central nervous system.

Making Physiological Cysteine Compositions

The natural pH of cysteine hydrochloride solutions (e.g., at concentrations of 50 mg/ml or more in 0.9% saline) is very low, for example, about pH 0.8 to pH 1.0. If a solution of cysteine were administered that had such a low pH, the patient would experience extensive irritation if not outright trauma. Such irritation and trauma can be avoided by administering cysteine solutions that have somewhat higher pH values of about pH 4.0 to about pH 5.5. However, cysteine can oxidize and/or dimerize to form cystine, which is an inactive precipitate, and cysteine solutions adjusted with sodium hydroxide to pH values above 3 exhibit rapid cystine precipitation. Moreover, cysteine is not soluble at concentrations greater than 50 mg/ml in its base form, and this concentration is generally too dilute for convenient administration to a patient. Instead, a solution containing 100 to 300 mg/ml, or 150-250 mg/ml, or more, cysteine is much more convenient for administration to patients.

In view of these and other issues, the inventors have developed methods of making solutions of cysteine that are physiologically acceptable, that are of sufficient concentration for efficient reversal of a neuromuscular blockade in a patient, and that are sufficiently stable to be stored for significant periods of time.

In one embodiment, the inventors provide a method of making a cysteine solution for physiological administration that involves obtaining an aqueous solution of cysteine with a pH of about 1.80 to about 2.20, and mixing the cysteine solution with a buffering solution to generate a cysteine solution for physiological administration that has a pH of about 4.5 to about 5.5, wherein each of the solutions are maintained under an atmosphere that is substantially without oxygen. In some embodiments the aqueous solution of cysteine has a pH of about 1.90 to about 2.00. The aqueous solution of cysteine is dissolved in a physiologically acceptable aqueous medium. For example, the aqueous solution of cysteine can be made from water (e.g., pyrogen-free, sterile water), physiological saline (e.g., 0.9% or 0.91% sodium chloride, weight per volume), sugar-water solutions (e.g., glucose or dextrose), or combinations thereof.

In another embodiment, the inventors provide a method of making a stable cysteine solution that can be stored prior to physiological administration, where the method involves:

a) removing oxygen from a volume of physiological saline or water;
b) adding sufficient cysteine to the physiological saline or water to generate a 150-350 mg/ml cysteine solution;
c) adjusting the pH of the cysteine solution to a pH of about 1.90 to about 2.00;
d) sparging the cysteine solution having the pH of about 1.90 to about 2.00 with non-oxygen containing gas to generate a deoxygenated cysteine solution; and
e) dispensing the deoxygenated cysteine solution into a container and sealing the container, to thereby make the stable cysteine solution that can be stored prior to physiological administration.

The stable cysteine solution can be stored for up to about 1 year, or up to about 8 months or up to about 6 months. In some embodiments, the stable cysteine solution is stored frozen. Thus, it may be advantageous to store the stable cysteine solutions at about −70° C. to about −10° C., or at about −20° C.

The stable cysteine solutions can be prepared for physiological administration by adjustment of the cysteine solution pH to about 4.4 to about 5.5 as follows:

f) adding a buffering solution to the stable cysteine solution to adjust the pH to about 4.4 to about 5.5 without exposing the stable cysteine solution to significant oxygen;

g) mixing the buffering solution into the stable cysteine solution to generate a cysteine solution for physiological administration that has a pH of about 4.5 to about 5.5, wherein the mixing is performed without exposing stable cysteine solution or the each of the solutions are maintained under an atmosphere that is substantially without oxygen.

To remove oxygen from the aqueous solution of cysteine, the buffering solution and/or the cysteine solution for physiological administration, the water or physiological saline can be de-gassed under a vacuum, and/or bubbled with a gas such as nitrogen or other inert gas (e.g., argon) for a time sufficient to significantly remove or replace the dissolved gases (e.g., oxygen) in the water or saline. Such de-gassing and replacement of dissolved gases can be done prior to addition of the solid cysteine or buffering solution. Alternatively, such de-gassing and/or replacement of dissolved gases can be after addition of the solid cysteine or buffering solution, or both before and after addition of the solid cysteine or buffering solution. The phrase "oxygen has been substantially removed" therefore means that a solution has been de-gassed under a vacuum, and/or bubbled with a gas such as nitrogen or other inert gas (e.g., argon) for a time sufficient to significantly remove or replace the dissolved gases (e.g., oxygen) in the water or saline.

The stable solutions of cysteine, with a pH of about 1.8 to about 2.1, or a pH of about 1.9 to about 2.0, can be sparged with a non-oxygen containing gas (e.g., nitrogen or argon) to remove dissolved oxygen prior to sealing the stable solutions of cysteine in a container.

The term "stable" means that the cysteine remains substantially in solution and the majority of the cysteine does not dimerize to form cystine for up to about 12 months, or up to about 8 months, or up to about 6 months, or up to about 3 or 4 months.

For example, the following formulations of cysteine were generated and exhibited sufficient stability after pH adjustment to about pH 4.5 to 5.5 for physiological administration.

1) Formulation 1, L-Cysteine Hydrochloride Monohydrate, 250 mg/mL, CaNa$_2$EDTA at 0.2 mg/mL, pH 2.2, Lot WFJC0003_1

L-Cysteine Hydrochloride Monohydrate was prepared by weighing 125 grams of L-Cysteine Hydrochloride Monohydrate into a 500-mL glass beaker containing about 300 mL of deoxygenated deionized Milli Q water by nitrogen gas for at least 1 hour prior to use, and 100 milligrams of edatate calcium disodium (EDTA).

As the L-Cysteine Hydrochloride Monohydrate dissolved, the solution became extremely cold so the temperature on the hot plate stirrer was turned up until the solution reached room temperature and the contents completely dissolved. The pH was then adjusted to 2.2±0.1 with 6.0N sodium hydroxide. The contents of the beaker were then quantitatively transferred to a 500 mL volumetric flask and QS to the mark with degassed Milli-Q water and sparged with nitrogen gas for about 30 minutes prior to filling into glass vials.

After degassing, the solution was then filtered through a 0.22 micron PVDF filter and filled with a repeat pipettor to a target volume of 8.0 mL into clean 10 cc vials in a laminar flow hood. The filled vials were sealed with 20 mm grey rubber stoppers, sealed by crimping with (blue) aluminum caps and label appropriately with formulation components including the date of manufacturing (DOM).

The appearance and pH were recorded after filtration in the notebook and samples stored at −20° C. until used for mixing studies.

2) Formulation 2, L-Cysteine Hydrochloride Monohydrate, 250 mg/mL, ascorbic acid at 10 mg/mL, pH 2.2, Lot WFJC0003_2

L-Cysteine Hydrochloride Monohydrate was prepared by weighing 125 grams of L-Cysteine Hydrochloride Monohydrate and 5 grams of ascorbic acid into a 500-mL glass beaker containing about 300 mL of deoxygenated deionized Milli Q water by nitrogen gas for at least 1 hour prior to use As the L-Cysteine Hydrochloride Monohydrate dissolved, the solution became extremely cold so the temperature on the hot plate stirrer was turned up until the solution reached room temperature and the contents completely dissolved. The pH was then adjusted to 2.2±0.1 with 6.0N sodium hydroxide. The contents of the beaker were then quantitatively transferred to a 500 mL volumetric flask and QS to the mark with degassed Milli-Q water and sparged with nitrogen gas for about 30 minutes prior to filling into glass vials.

After degassing, the solution was then filtered through a 0.22 micron PVDF filter and filled with a repeat pipettor to a target volume of 8.0 mL into clean 10 cc vials in a laminar flow hood. The filled vials were sealed with 20 mm grey rubber stoppers, sealed by crimping with (green) aluminum caps and label appropriately with formulation components including the date of manufacturing (DOM).

The appearance and pH were recorded after filtration in the notebook and samples stored at −20° C. until used for mixing studies.

3) Formulation 5, L-Cysteine Hydrochloride Monohydrate at 250 mg/mL, ascorbic acid at 10 mg/mL and sodium acetate at 2.6 mg/mL pH 2.2, Lot WFJC0003_5.

L-Cysteine Hydrochloride Monohydrate was prepared by weighing 125 grams of L-Cysteine Hydrochloride Monohydrate, 5 grams of ascorbic acid and 1.3 grams of sodium acetate into a 500-mL glass beaker containing about 300 mL of deoxygenated deionized Milli Q water by nitrogen gas for at least 1 hour prior to use.

As the L-Cysteine Hydrochloride Monohydrate dissolved, the solution became extremely cold so the temperature on the hot plate stirrer was turned up until the solution reached room temperature and the contents completely dissolved. The pH was then adjusted to 2.2±0.1 with 6.0N sodium hydroxide. During the formulation, the total volume the solution ended up at 580 mL because too much solvent was added initially and not leaving enough room for volume of solute added. This oversight was learned as this was the first solution prepared and was not repeated with the other formulations. The final solution was sparged with nitrogen gas for about 30 minutes prior to filling into glass vials.

After degassing, the solution was then filtered through a 0.22 micron PVDF filter and filled with a repeat pipettor to a target volume of 8.0 mL into clean 10 cc vials in a laminar flow hood. The filled vials were sealed with 20 mm grey rubber stoppers, sealed by crimping with (silver) aluminum caps and label appropriately with formulation components including the date of manufacturing (DOM).

The stable cysteine solution may contain bacteriostatic agents, chelating agents, antioxidants, glutathione or other pharmaceutically acceptable additives that do not contribute to the oxidation and/or dimerization of cysteine. For example, the stable cysteine solutions can contain antioxidant vitamins and cofactors such as ascorbic acid, vitamin A, vitamin E, coenzyme Q10, flavonoids, and the like. Examples of chelating agents that the stable cysteine solutions can contain include citric acid, dicarboxymethylglutamic acid, ethylenediaminedisuccinic acid (EDDS), ethylenediaminetetraacetic acid (EDTA), hepta sodium salt of diethylene triamine penta (methylene phosphonic acid) ($DTPMP.Na_7$), malic acid, nitrilotriacetic acid (NTA), methionine, oxalic acid, phosphoric acid, polar amino acids (e.g., arginine, asparagine, aspartic acid, glutamic acid, glutamine, lysine, and ornithine), siderophores (e.g., Desferrioxamine B), succinic acid and the like.

The buffering solution employed for raising the pH of the cysteine solutions is an aqueous solution of a compound that can bind one or more hydrogen atoms. In some embodiments, such a compound is a weak base or anion. Examples of compounds that can be employed in the buffering solution include tris(hydroxymethyl)methylamine (Tris), N,N-bis(2-hydroxyethyl)glycine (Bicine), N-tris(hydroxymethyl)methylglycine (Tricine), 4-2-hydroxyethyl-1-piperazineethanesulfonate (HEPES), {[tris(hydroxymethyl) methyl] amino}ethanesulfonate (TES), 3-(N-morpholino)propanesulfonate (MOPS), piperazine-N,N'-bis(2-ethanesulfonate (PIPES), 2-(N-morpholino)ethanesulfonate (MES) and combinations thereof. In some embodiments, the compound employed in the buffering solution is Tris.

Kits

Another embodiment of the invention is a kit that can include at least two containers, a first container with a stable solution of cysteine that has a pH of about 1.8 to about 2.1, and a second container with a buffering solution for raising the pH of the stable solution of cysteine.

The kits can contain additional items. Examples include one or more syringes and needles for transferring an appropriate amount of the buffering solution to the stable solution of cysteine and administering the physiological solution of cysteine to a patient, as well as instructions for storing the kit, for raising the pH of the stable solution of cysteine to an appropriate pH and/or for administering the physiological solution of cysteine to reverse a neuromuscular blockade.

In another aspect of the invention, the kit can include a third container that contains a neuromuscular blocking agent, for example, any neuromuscular blocking agent whose blockade can be reversed by cysteine. Examples of neuromuscular blocking agents are provided herein and are described herein as well as those described in PCT/US2010/000796, filed Mar. 17, 2010; U.S. Ser. No. 11/951,114, filed Dec. 5, 2007; U.S. application Ser. No. 10/975,197, filed Oct. 28, 2004; PCT Application Ser. No. PCT/US2004/035869, filed Oct. 28, 2004; U.S. Application Ser. No. 60/515,048, filed Oct. 28, 2004; and U.S. Provisional Application Ser. No. 61/160,915, filed Mar. 19, 2009, the contents of each of which applications are specifically incorporated herein by reference in their entireties.

Such kits are useful during surgical procedures involving a neuromuscular blockade and reversal of the blockade. The present invention also provides the use of cysteine or glutathione with or without a neuromuscular blocking agent for reversing neuromuscular blockade in a mammal, including in a human.

Methods of Use

The present invention also provides a method for reversing muscle relaxation in a mammal caused by neuromuscular blocking agents. Such methods include administering to the mammal a physiological solution of cysteine or glutathione in an amount effective for reversing the neuromuscular block produced by neuromuscular blocking agent. In some embodiments, the method involves administration of L-cysteine. In other embodiments, the method involves administration of D-cysteine. In further embodiments, a mixture of L-cysteine, D-cysteine and/or glutathione can be administered.

A suitable dose of cysteine and/or glutathione to reverse a neuromuscular block in adult humans (150 lbs. or 70 kg) is about 50 mg to about 2000 mg or about 150 to about 750 mg. Thus a suitable physiological solution of cysteine or glutathione for administration to humans will preferably contain 100 to 300 mg/ml or 150-250 mg/ml or more cysteine or glutathione in one or more single dose vials.

The physiological solution of cysteine or glutathione may be administered parenterally, intramuscularly or intravenously as a bolus over about 5 seconds to about 15 seconds or, alternatively, as a slower or drip infusion over about 1 to about 2 minutes of a saline solution, e.g., Ringer's solution in drip form.

Neuromuscular Blocking Agents

The physiological cysteine solutions can be used to reverse neuromuscular blockades generated by a variety of neuromuscular blocking agents, including those having ultra-short to intermediate to long duration. The physiological cysteine solutions can include L-cysteine or D-cysteine and combinations thereof. In some embodiment the physiological cysteine solutions can also include glutathione, which in some may extend the reversal activity of cysteine and/or reduce the cysteine dosage to be administered.

For example, the physiological cysteine solutions can be used to reverse neuromuscular blockades that have a duration time of about 5 to 60 minutes. However, when cysteine and/or glutathione compounds are administered the patient will recover from the effects of the halofumarate neuromuscular blocking agents within about 30 seconds to about 300 seconds and, in some embodiments within about 30 to about 180 seconds, or even within about 30 seconds to about 120 seconds. Hence, use of the methods, compositions and kits of the invention will provide increased safety over known antagonists for available neuromuscular blocking agents because of the speed at which the cysteine works and the absence of any side effects.

Examples of neuromuscular blocking agents that can be inactivated by the cysteine and/or glutathione provided herein include compounds described herein and in U.S. Pat. No. 6,187,789, which is specifically incorporated herein by reference. Other examples include the neuromuscular blocking agents described in U.S. Ser. No. 11/951,114, filed Dec. 5, 2007; U.S. application Ser. No. 10/975,197, filed Oct. 28, 2004; PCT Application Ser. No. PCT/US2004/035869, filed Oct. 28, 2004; U.S. Application Ser. No. 60/515,048, filed Oct. 28, 2004; and U.S. Provisional Application Ser. No. 61/160,915, filed Mar. 19, 2009, the contents of each of which applications are specifically incorporated herein by reference in their entireties.

In some embodiments, the neuromuscular blocking agent is a compound of formula (I)

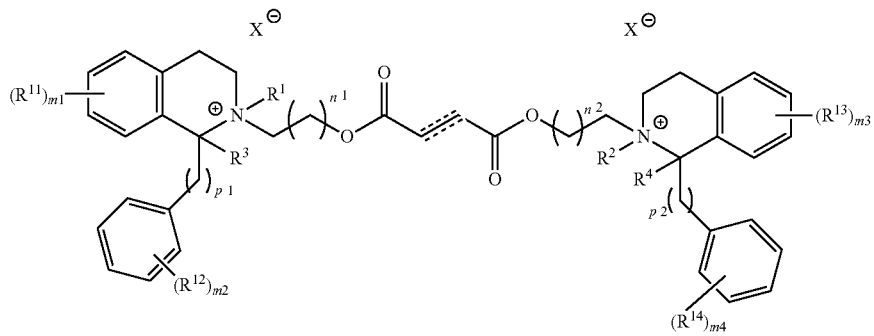

wherein
a double dashed line indicates that a double bond or a triple bond is present at that position; the double bond, when present, is of Z or E configuration and each carbon atom of the double bond is substituted with a single respective hydrogen atom; for the single bond, when present, each carbon atom bears two respective hydrogen atoms;

$R^1$ and $R^2$ are each independently $(C_1-C_4)$alkyl, $(C_1-C_4)$alkenyl, or $(C_1-C_4)$alkynyl;

$R^3$ and $R^4$ are each independently hydrogen or $(C_1-C_4)$alkyl, $(C_1-C_4)$alkenyl, or $(C_1-C_4)$alkynyl;

$R^{11}$, $R^{12}$, $R^{13}$, and $R^{14}$ are each independently $(C_1-C_4)$alkoxy or $(C_1-C_4)$acyloxy; or any two adjacent $R^{11}$, $R^{12}$, $R^{13}$, or $R^{14}$ are methylenedioxy;

m1 and m3 are each independently 2, 3, or 4;

m2 and m4 are each independently 2 or 3;

n1 and n2 are each independently 1 to about 4;

p1 and p2 are each independently 0 or 1;

X is independently at each occurrence a pharmaceutically acceptable anion;

including any stereoisomer thereof, or, any combination, solvate, hydrate, metabolite or prodrug thereof.

In various embodiments, compounds of the invention can be diesters of maleic acid, fumaric acid, or acetylenedicarboxylic acid, including any stereoisomer thereof, or, any combination, solvate, hydrate, metabolite or prodrug thereof.

Accordingly, in various embodiments, compound of the invention can be compounds wherein the double dashed line indicates a double bond in the Z configuration of the maleate formula

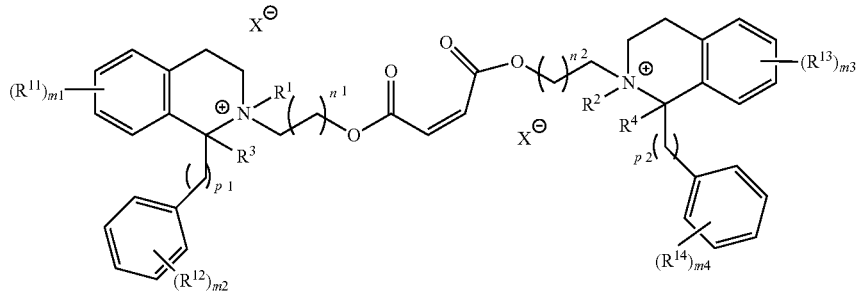

including any stereoisomer thereof, or, any combination, solvate, hydrate, metabolite or prodrug thereof.

Or, compounds of the invention can be compounds wherein the double dashed line indicates a double bond in the E configuration, of the fumarate formula

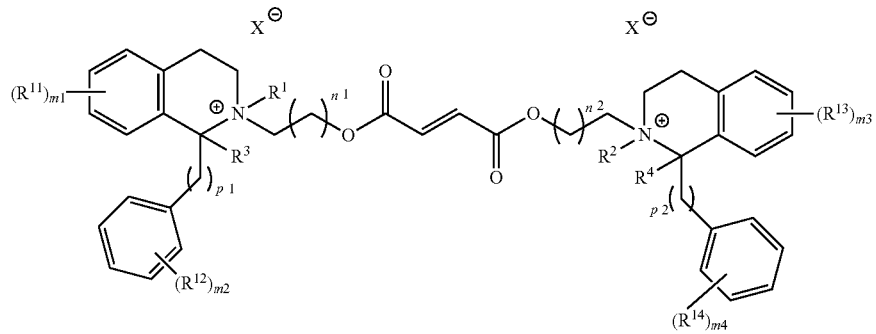

including any stereoisomer thereof, or, any combination, solvate, hydrate, metabolite or prodrug thereof.

Or, compounds of the invention can be compounds wherein the double dashed line indicates a triple bond of the acetylenedicarboxylate formula

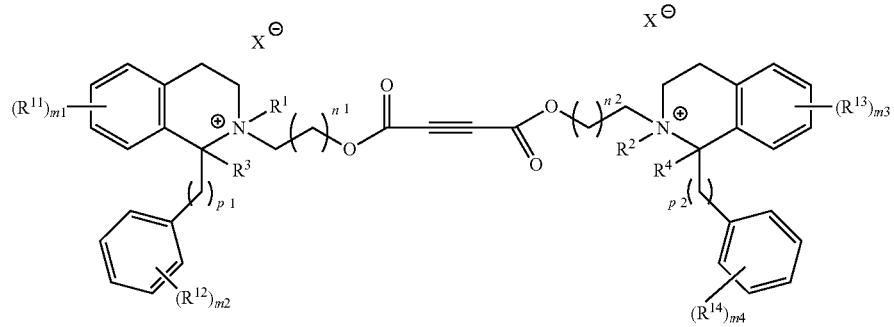

including any stereoisomer thereof, or, any combination, solvate, hydrate, metabolite or prodrug thereof.

Various embodiments are now described wherein particular substituents are more narrowly defined. These embodiments are not intended to limit the invention, but only to provide illustrative examples.

In various embodiments, a compound of the invention can be a compound wherein $R^1$, $R^2$, or both, are methyl.

In various embodiments, a compound of the invention can be a compound wherein $R^3$, $R^4$, or both, are hydrogen.

In various embodiments, a compound of the invention can be a compound wherein n1 and n2 are both 2.

In various embodiments, a compound of the invention can be a compound wherein m1 and m3 are each independently 2 or 3.

In various embodiments, a compound of the invention can be a compound wherein m2 and m4 are each independently 2 or 3.

In various embodiments, a compound of the invention can be a compound wherein $R^{11}$, $R^{12}$, $R^{13}$, and $R^{14}$ are all methoxy, or wherein any two of $R^{11}$, any two of $R^{12}$, any two of $R^{13}$, or any two of $R^{14}$, are methylenedioxy, or any combination thereof.

In various embodiments, a compound of the invention can be a compound wherein $R^1$ and $R^3$ are in a trans configuration.

In various embodiments, a compound of the invention can be compounds wherein $R^2$ and $R^4$ are in a trans configuration.

In various embodiments, a compound of the invention can be a compound wherein the carbon atom bearing $R^3$, the carbon atom bearing $R^4$, or both carbon atoms, are in the R absolute configuration.

In various embodiments, a compound of the invention can be a compound wherein the nitrogen atom bearing $R^1$, the nitrogen atom bearing $R^2$, or both nitrogen atoms, are in the S absolute configuration.

In various embodiments, a compound of the invention can be a compound wherein both X are chloride.

In various embodiments, a compound of the invention can comprise an R-trans, R-trans compound of formula (II)

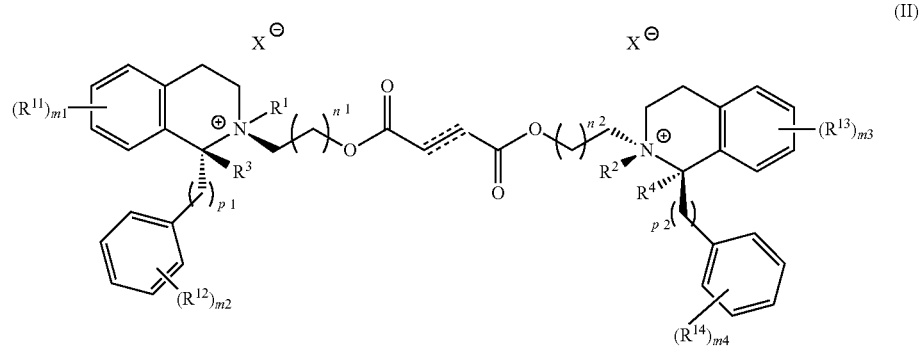

(II)

wherein a dashed line indicates a double bond or a triple bond, or any combination, solvate, hydrate, metabolite, or prodrug thereof. By an "R-trans, R-trans" compound is meant a compound having an R absolute stereochemical configuration at each of the carbon atoms bearing groups $R^3$ and $R^4$, wherein the benzyl moieties bonded to those carbon atoms are both disposed trans to the alkanol substituent on the respective adjacent nitrogen atom. Similarly, an "R-cis, R-cis" compound refers to a compound wherein an absolute R stereochemical configuration exists at the two carbon atoms bearing the $R^3$ and $R^4$ groups, wherein the benzyl moieties bonded to those carbon atoms are both disposed cis to the alkanol substituent on the respective adjacent nitrogen atom. In this manner, the stereochemistry of the two isoquinolylalkanol moieties bonded to the two carboxylic acid groups of the fumarate, maleate, or acetylenedicarboxylate moieties can be fully defined. For example, for a maleate compound (the terminology of which defines the stereochemistry of the central double bond as opposed to a fumarate compound), isomers such as "S-trans, S-trans," "S-trans, R-cis," "R-cis, S-trans," and all the other possible permutations can be specified. The present invention includes all such isomers of the specified generic structures disclosed herein and of all specific structures in which the stereochemistry is otherwise unspecified, encompassing R and S stereoisomers and cis and trans ring configurations in all combinations.

In various embodiments, a compound of the invention can comprise an R-trans, R-trans compound of formula (IIA)

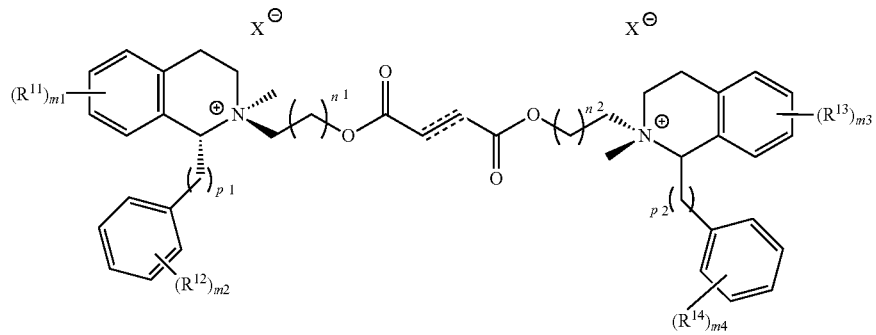

or any combination, solvate, hydrate, metabolite, or prodrug thereof.

In various embodiments, a compound of the invention can be a compound comprising an R-trans, R-trans compound of formula (IIA), wherein n1 and n2 are both equal to 2. For example, an R-trans, R-trans compound of formula (IIA), wherein n1 and n2 are both equal to 2 can be a maleate diester, or a fumarate diester, or an acetylenedicarboxylate diester. In various embodiments, for any of these compound, p1 and p2 can both be 1, or one of p1 and p2 is 0 and one of p1 and p2 is 1, or, p1 and p2 are both 0.

In various embodiments, a compound of the invention can be any of the following maleates:

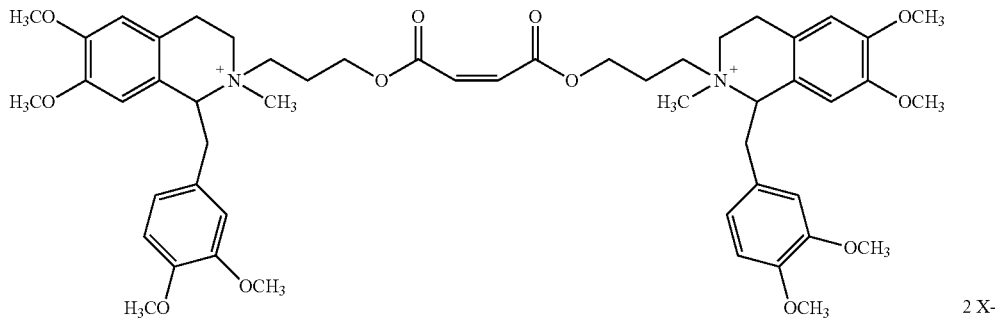

[R-trans, R-trans]

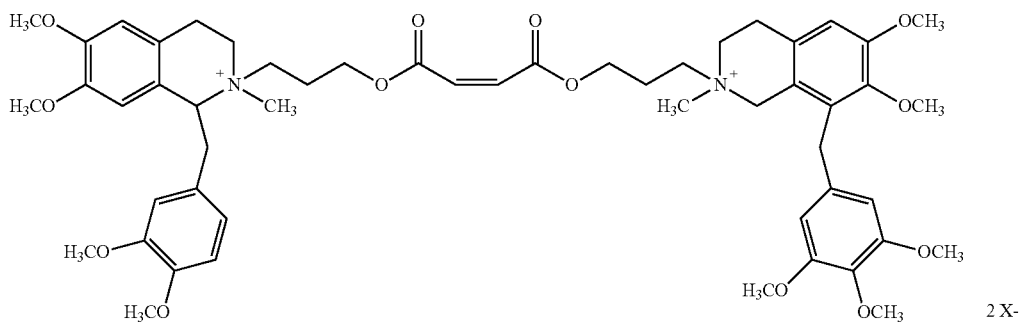

[R-trans, R-trans is NB 1043-46 (CW011)]

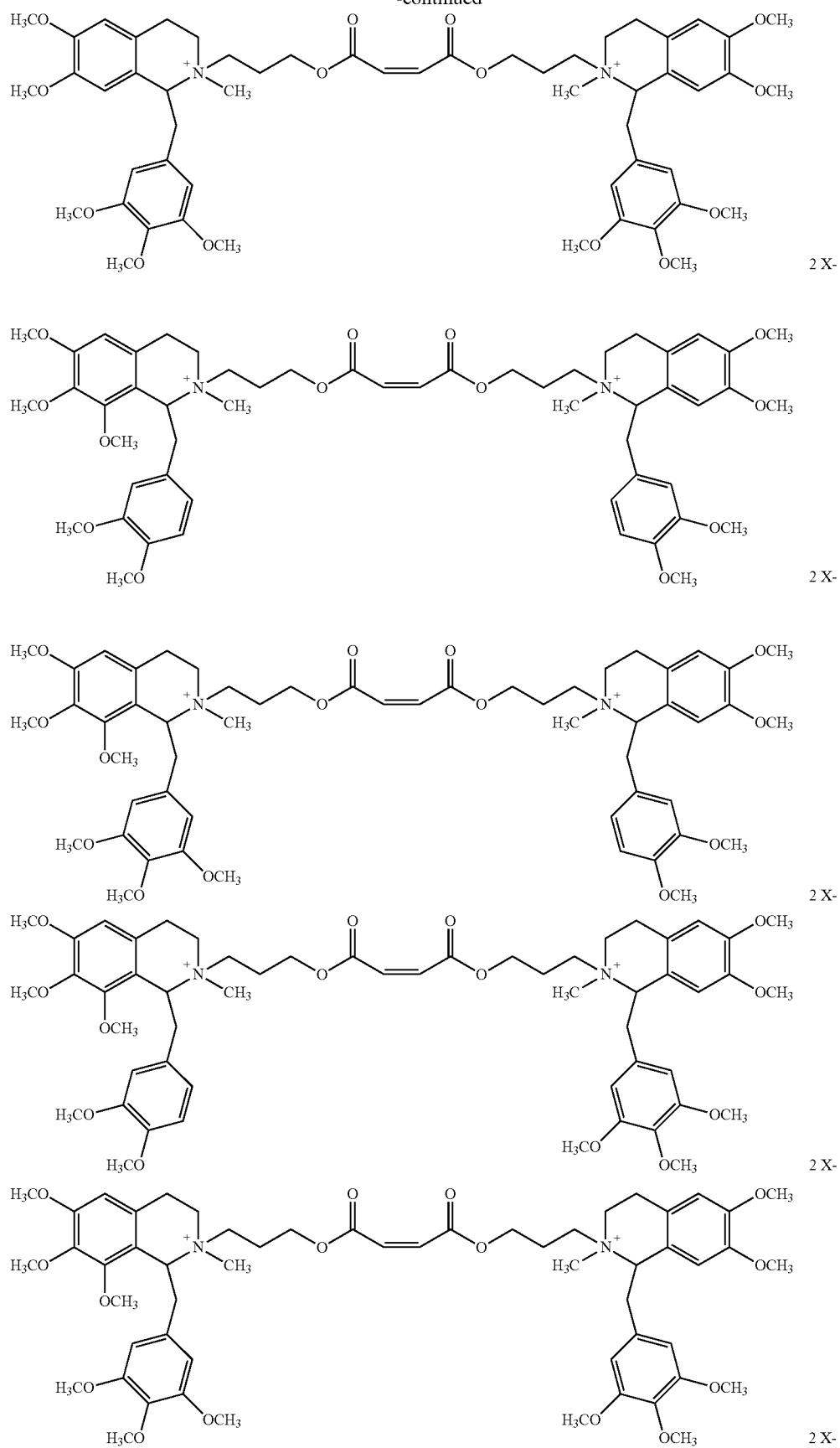

-continued
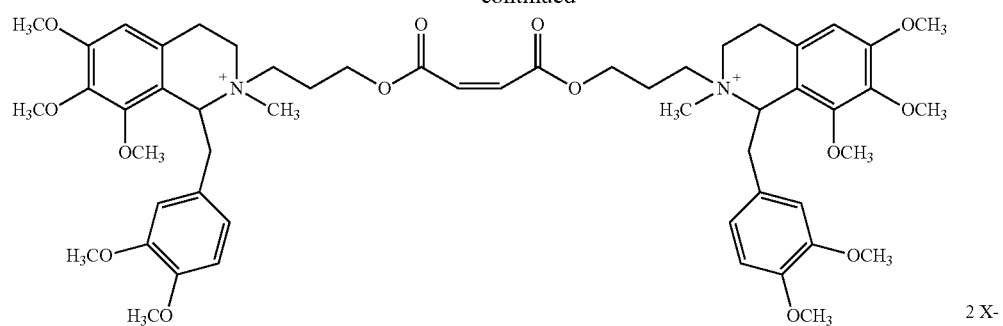
2 X-
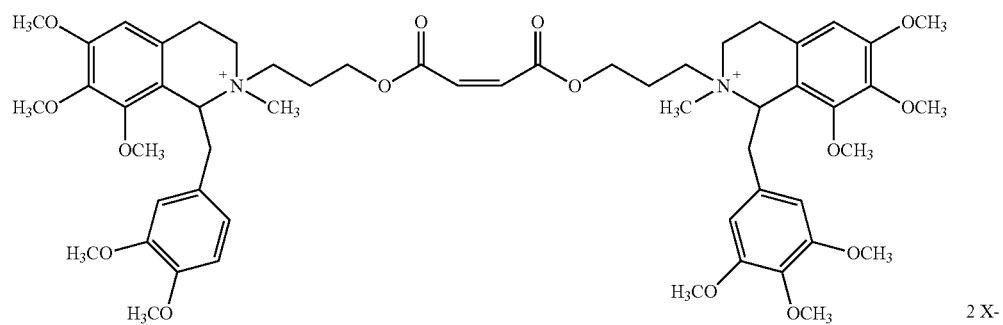
2 X-
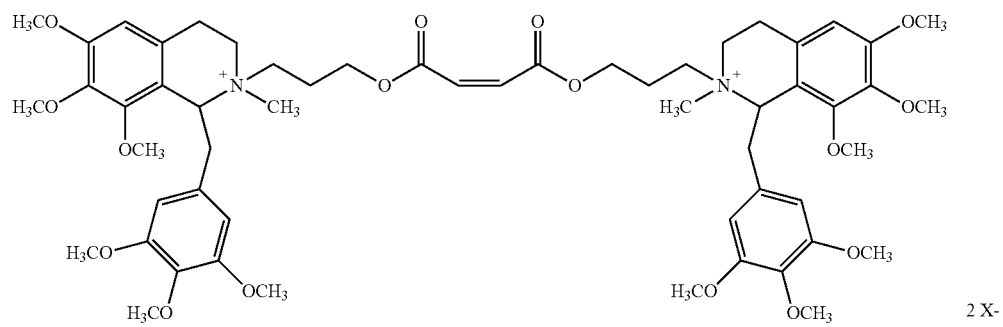
2 X-
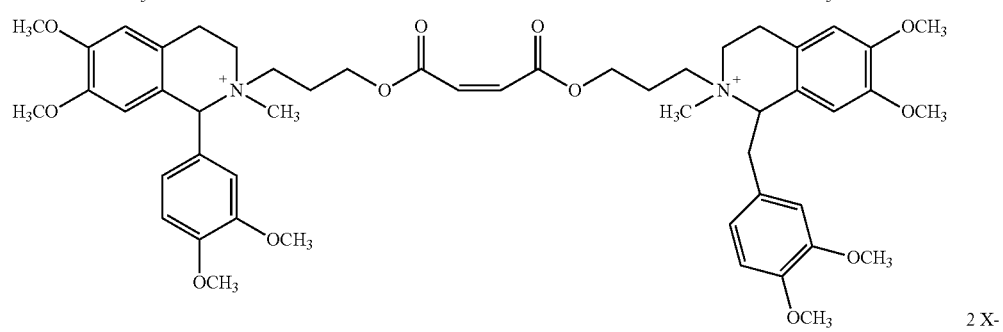
2 X-
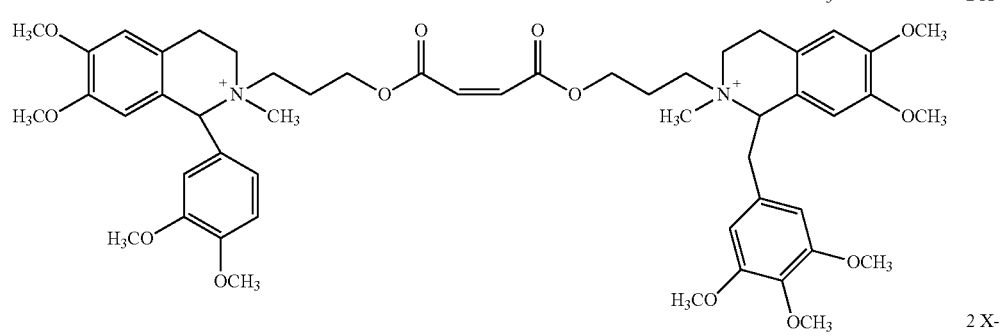
2 X-

-continued
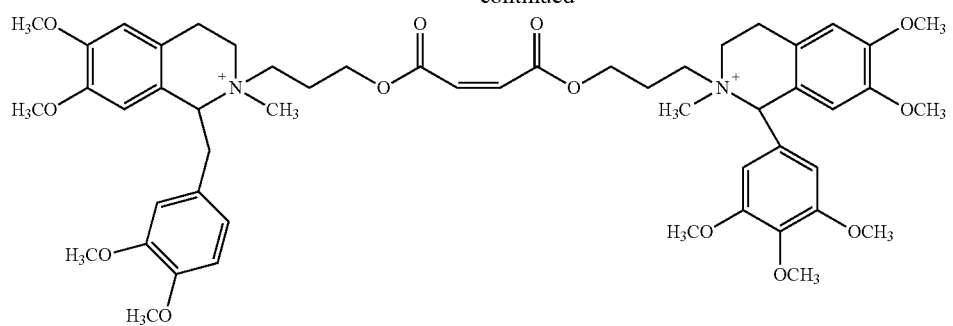
2 X⁻
[R-trans, R-trans is NB 1064-81]
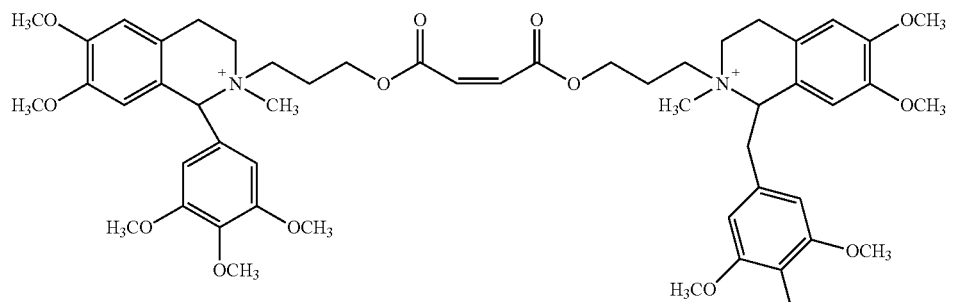
2 X⁻
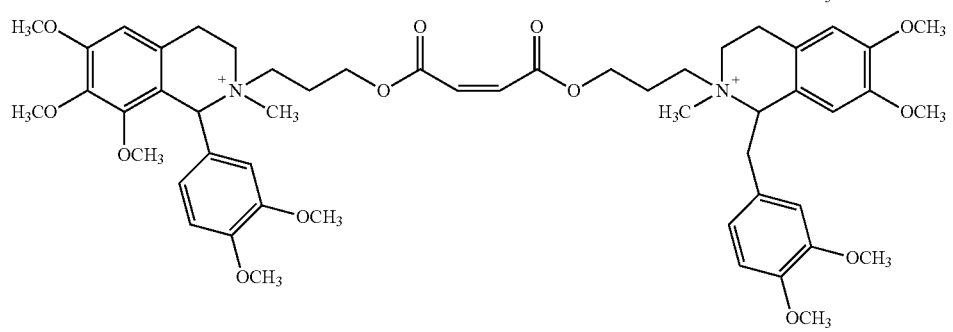
2 X⁻
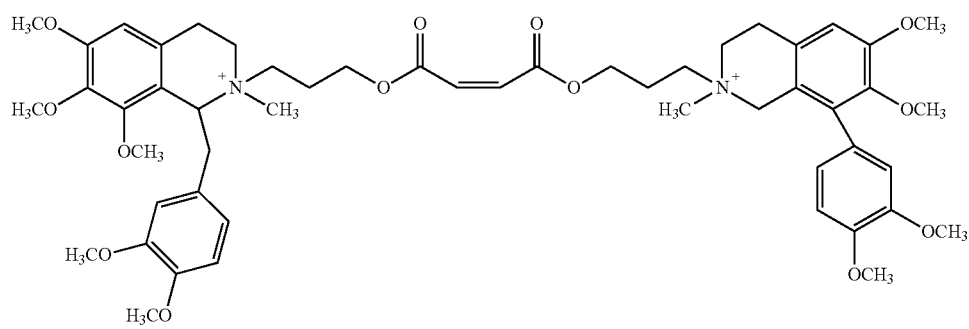
2 X⁻
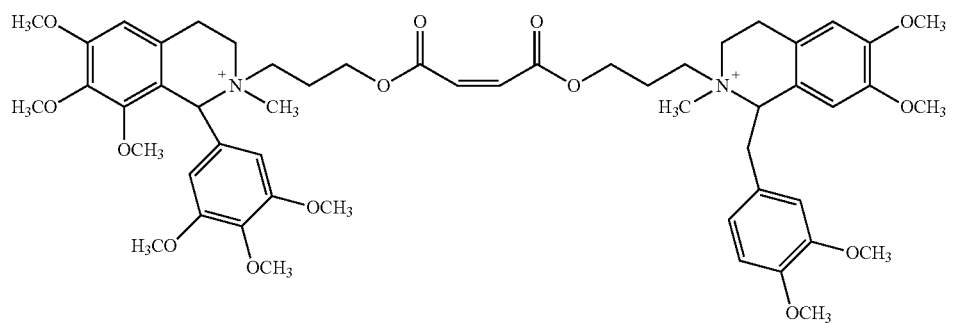
2 X⁻

-continued
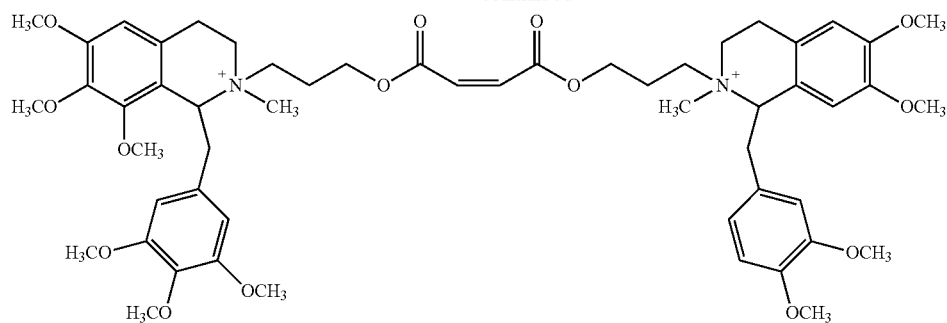
2 X−
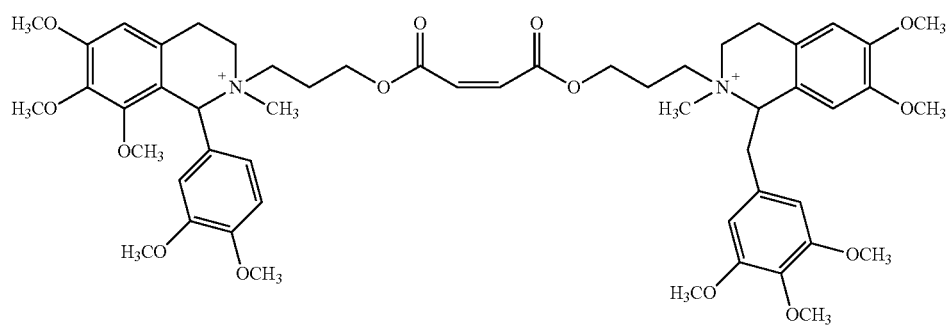
2 X−
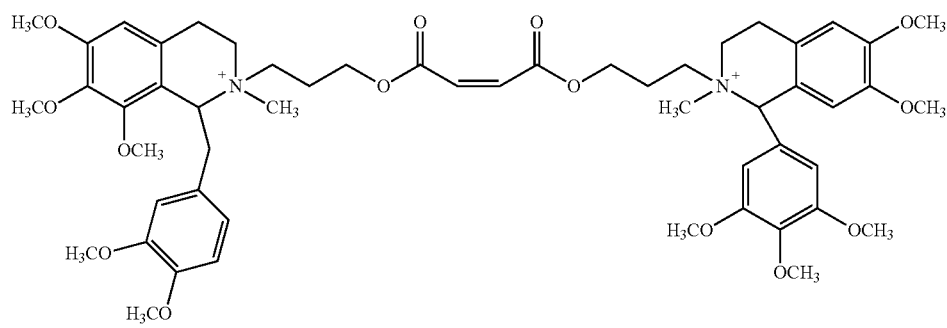
2 X−
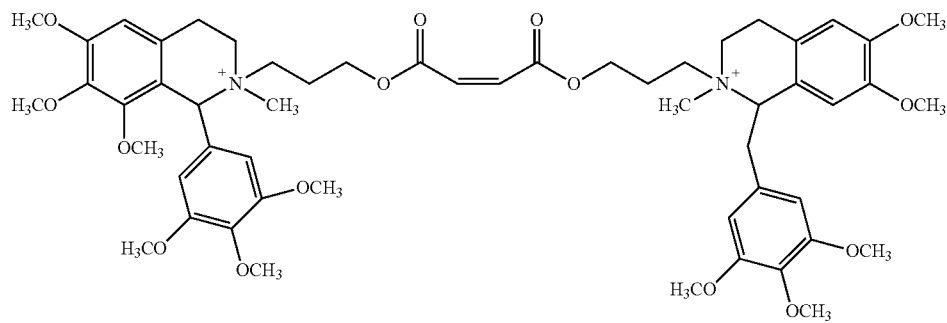
2 X−
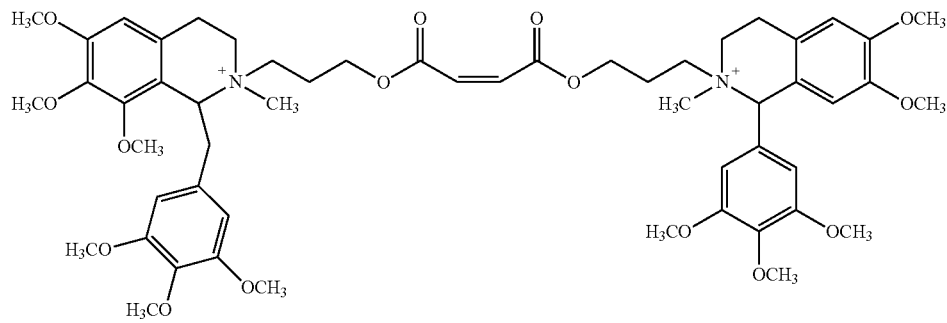
2 X−

-continued
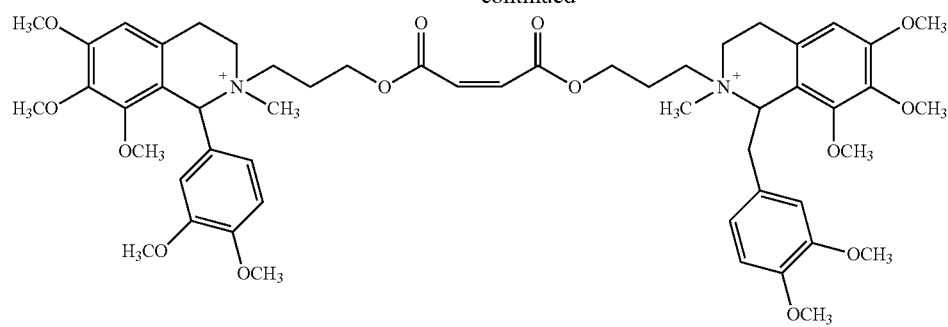
2 X-
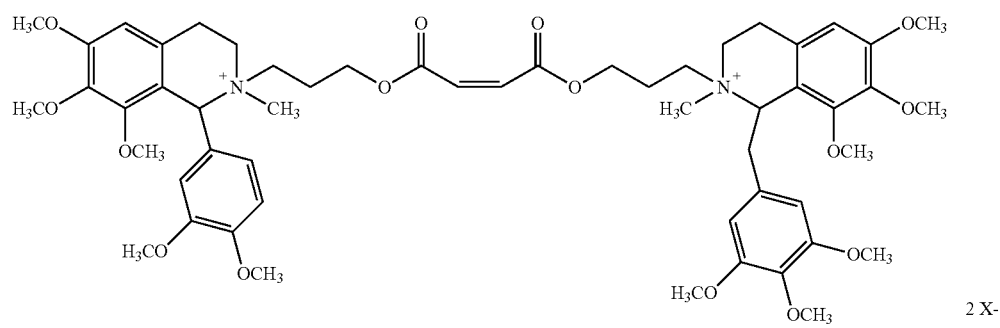
2 X-
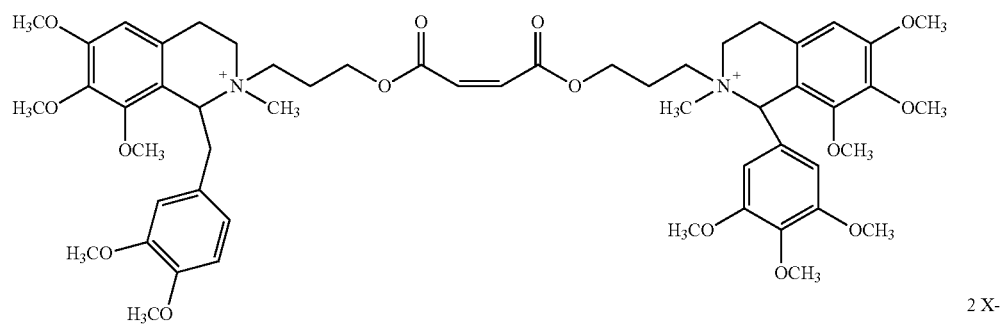
2 X-
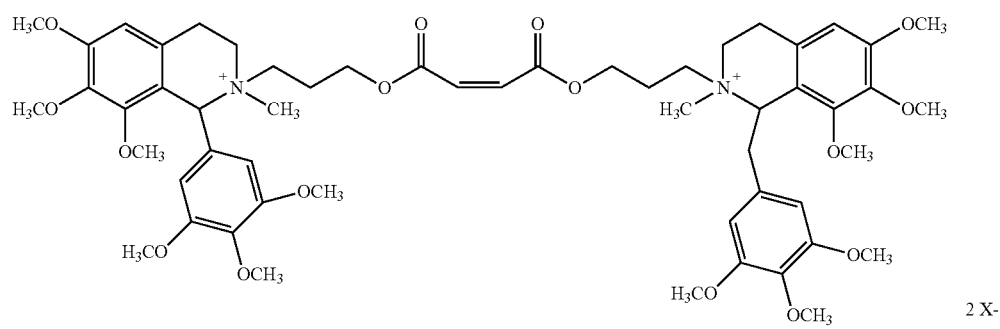
2 X- including any stereoisomer thereof, or any combination, solvate, hydrate, metabolite, or prodrug thereof.
In various embodiments, the maleate compound can be any of the following:
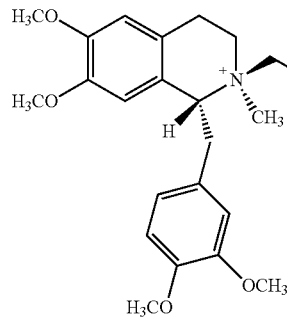 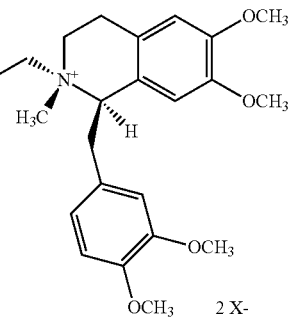
[NB 968-39]
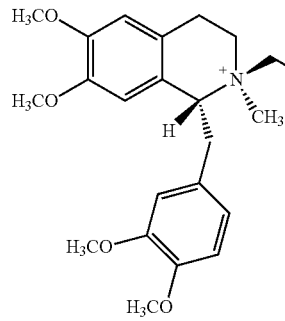 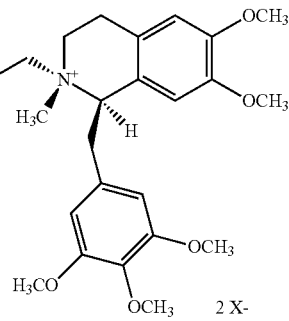
[NB 1043-46 (CW011)]
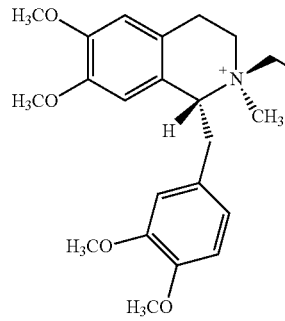 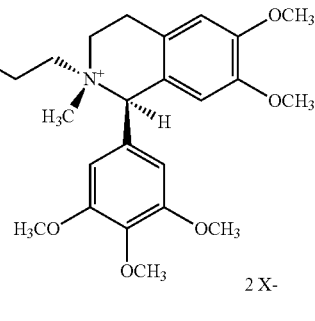
[NB 1064-81]
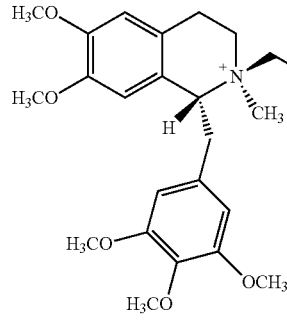 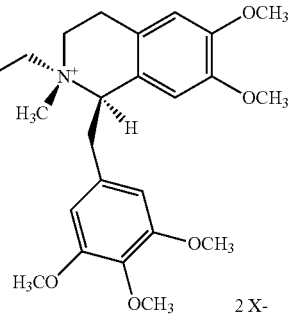

or any combination, solvate, hydrate, metabolite, or prodrug thereof.
In various embodiments, a compound of the invention can be any of the following fumarates:
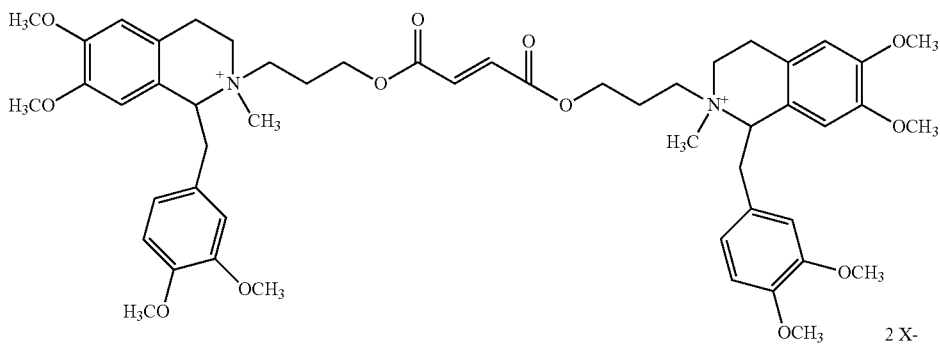
[R-trans, R-trans is NB 1025-68 (CW002), R-cis, R-cis is NB 832-65 (CW003)]
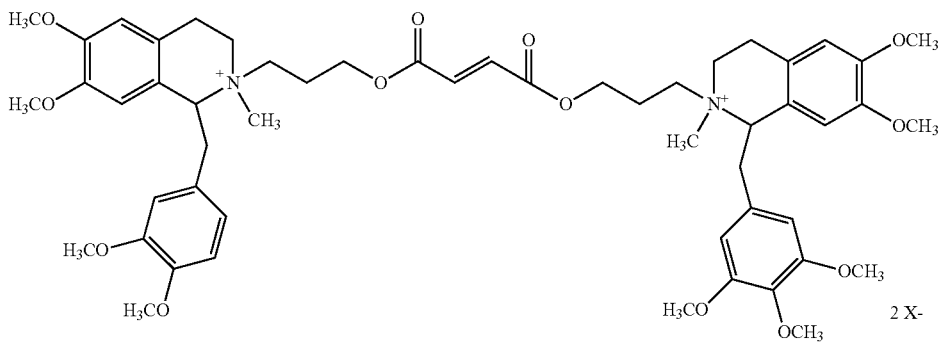
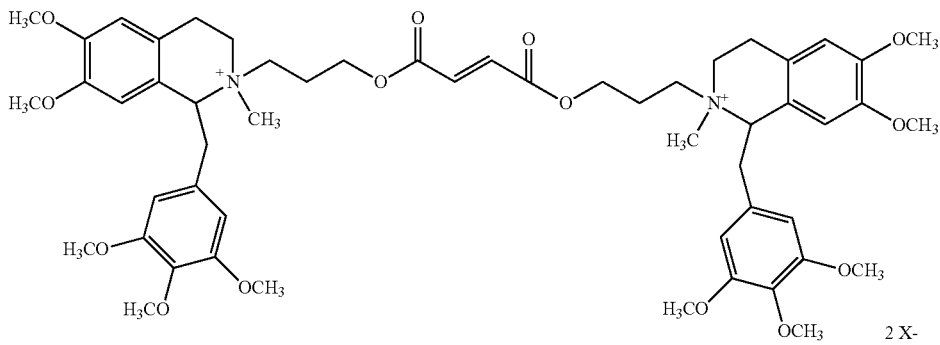
[R-trans, R-trans is NB 802-17 (CW001)]
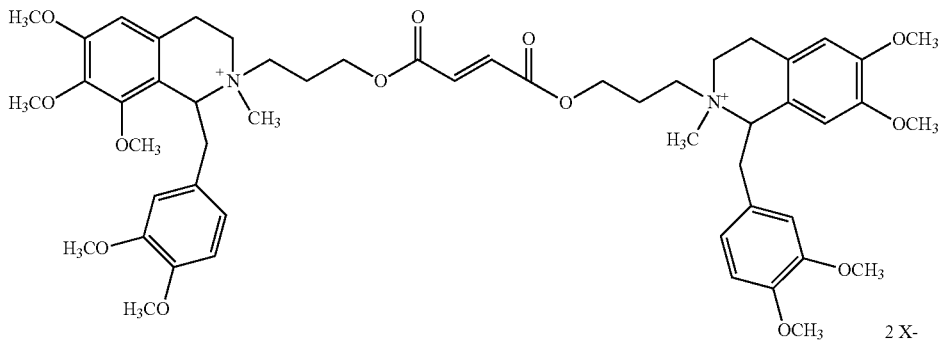

-continued
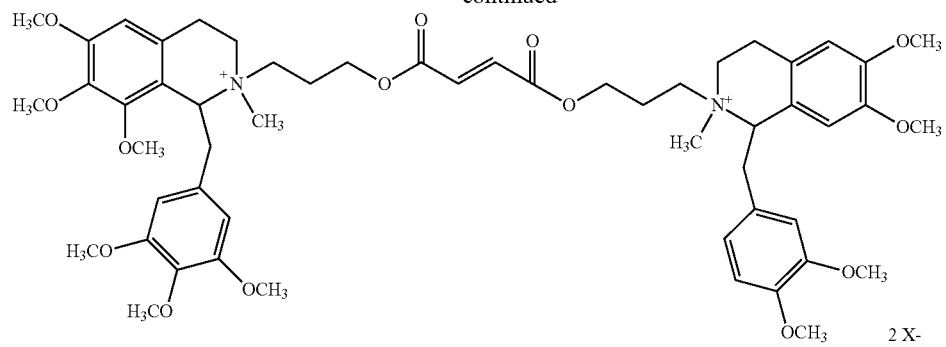
2 X−
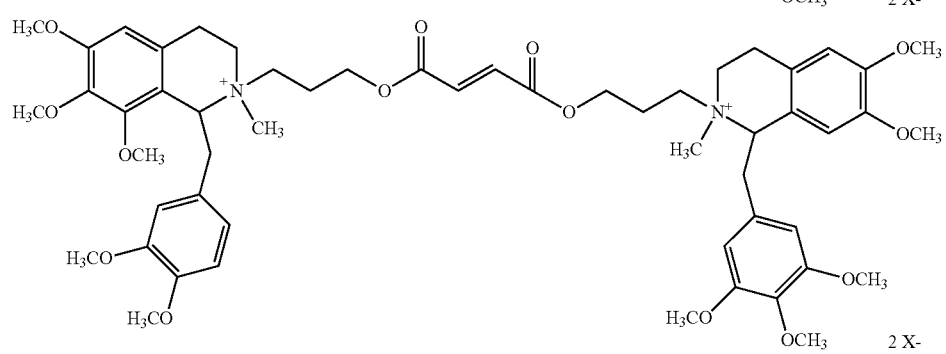
2 X−
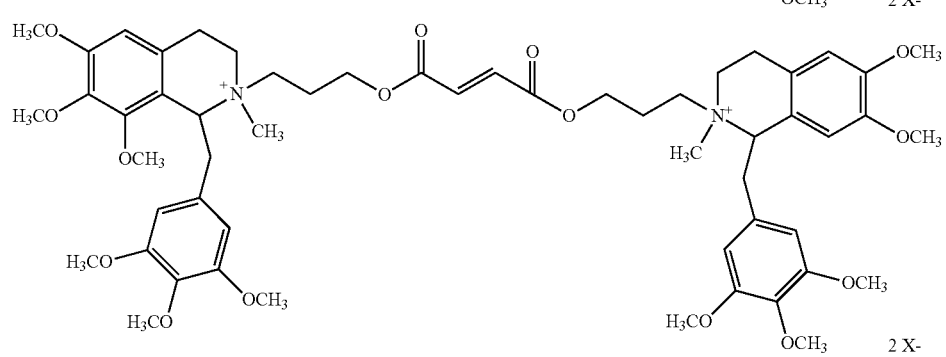
2 X−
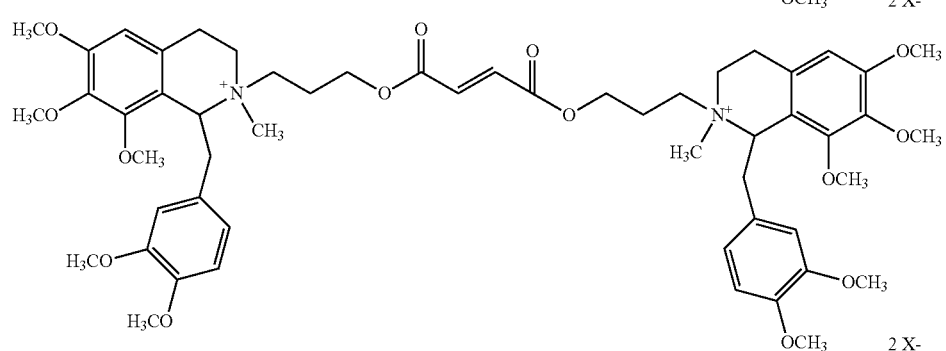
2 X−
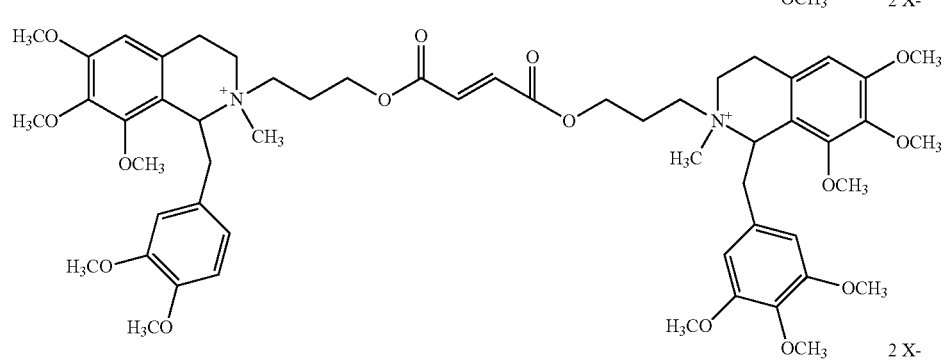
2 X−

-continued
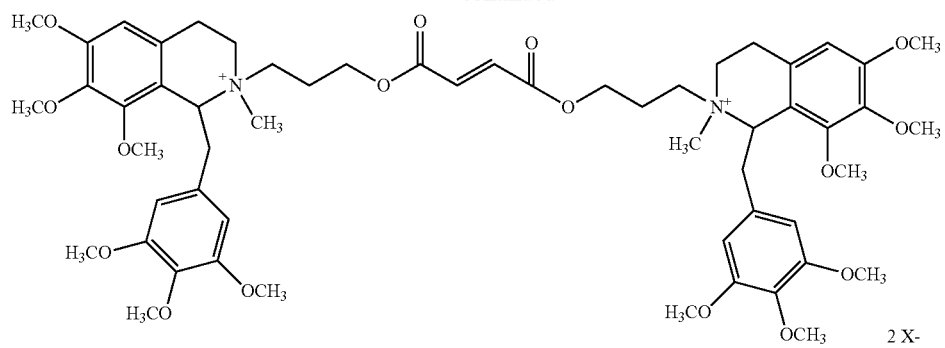
2 X-
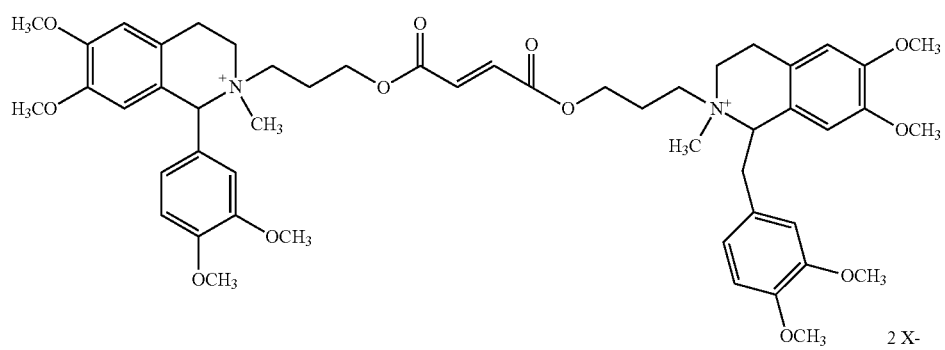
2 X-
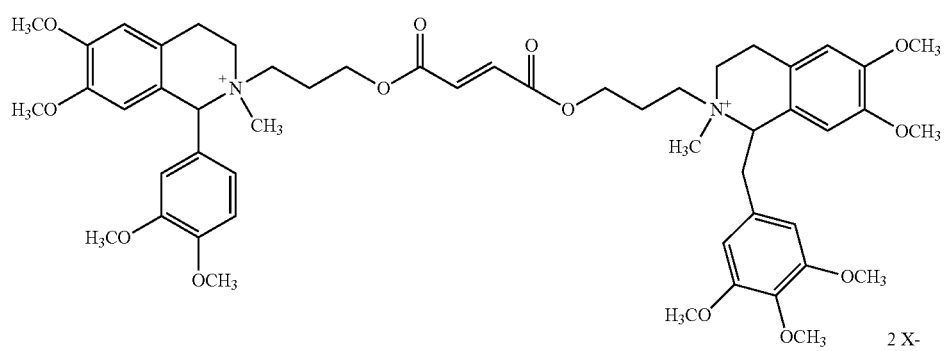
2 X-
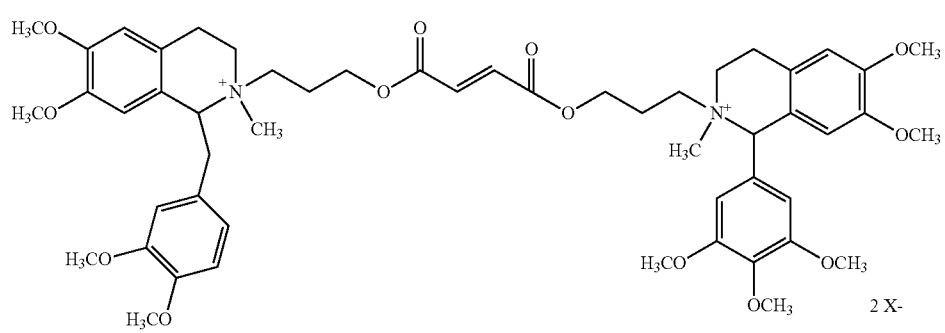
2 X-
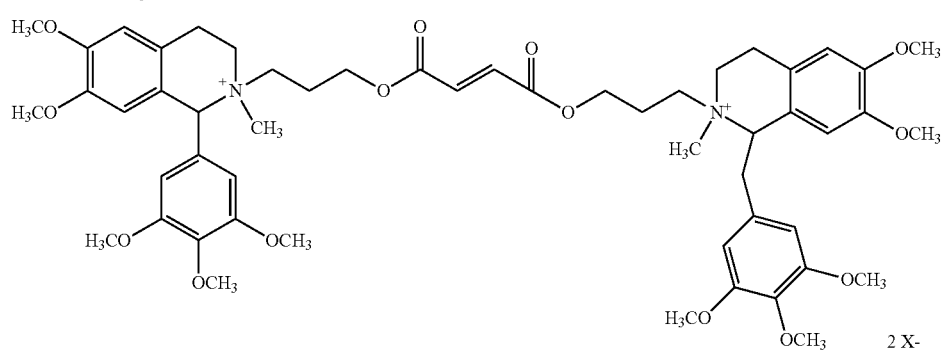
2 X-

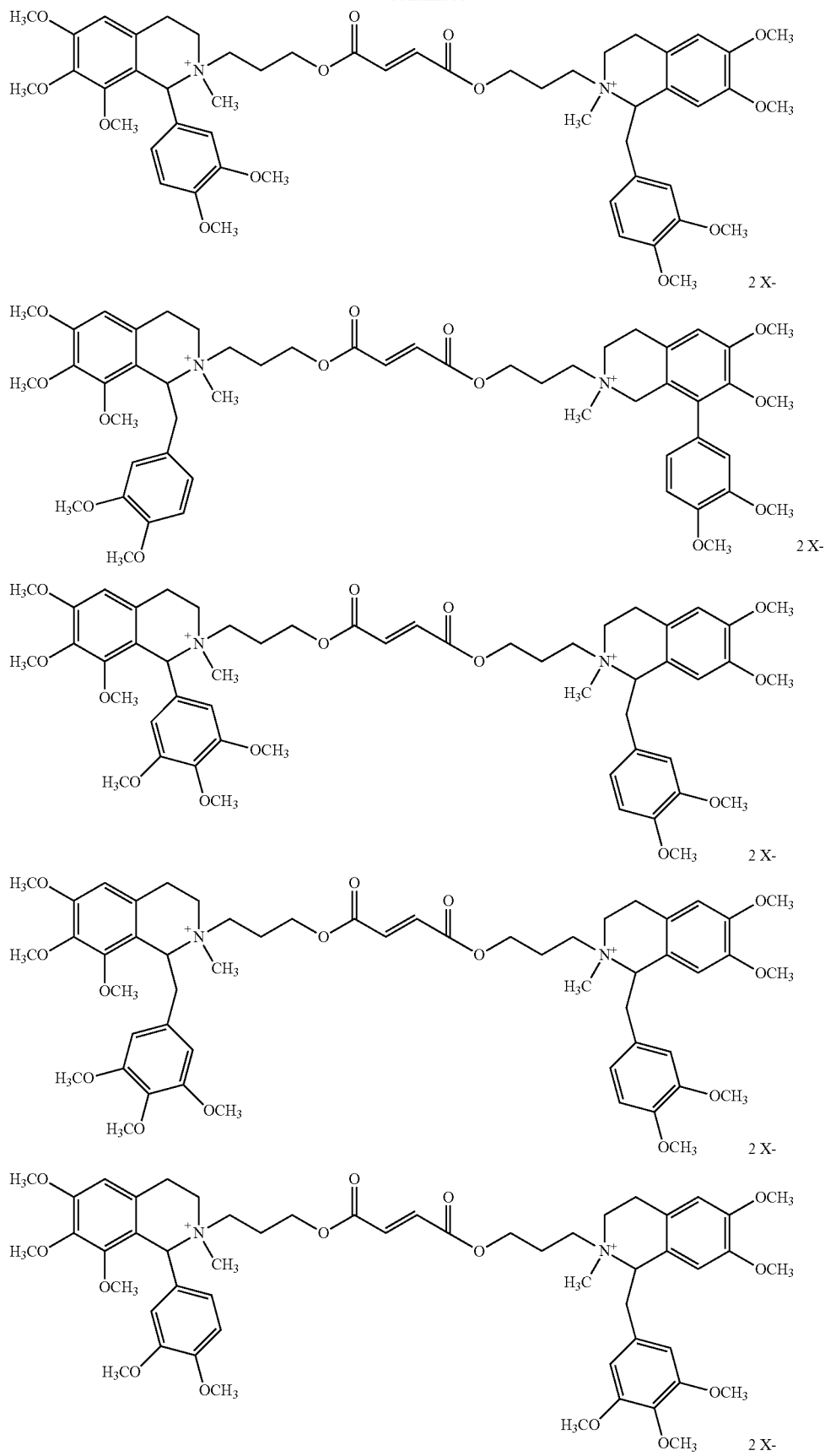
-continued

-continued
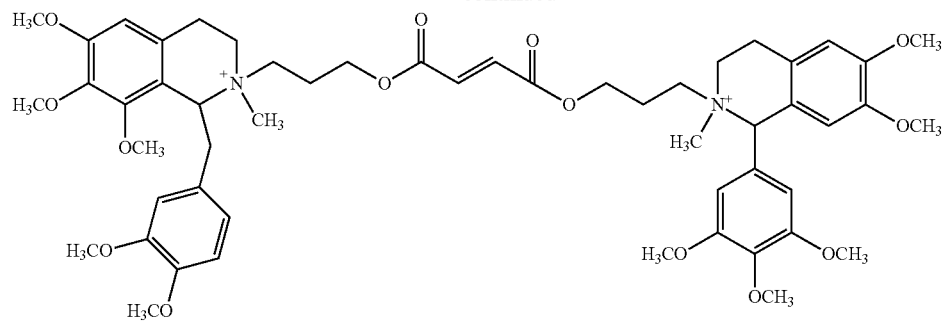
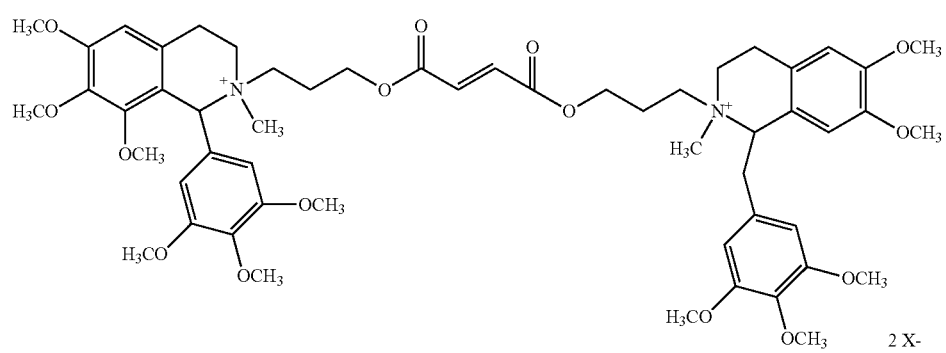
2 X⁻
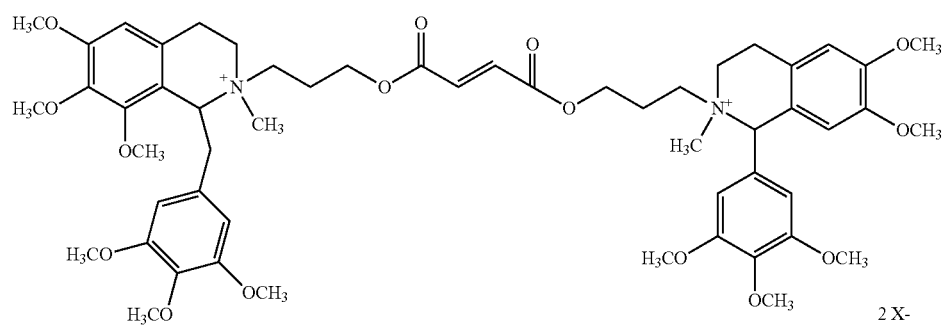
2 X⁻
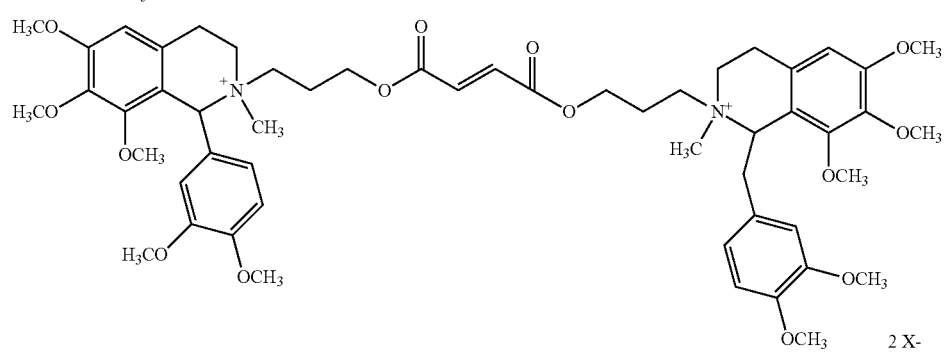
2 X⁻
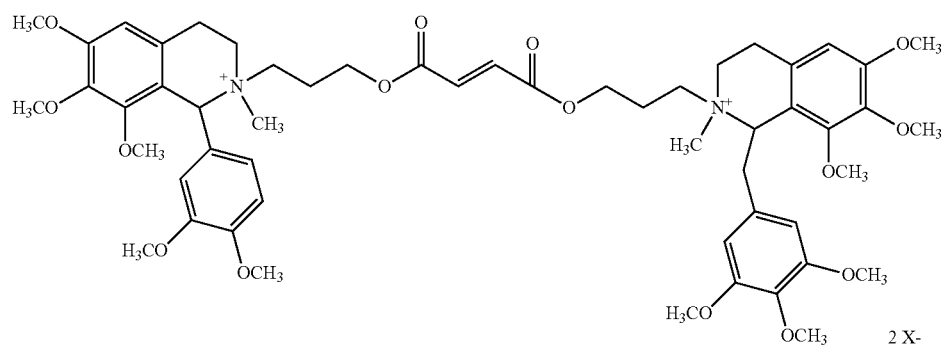
2 X⁻

-continued
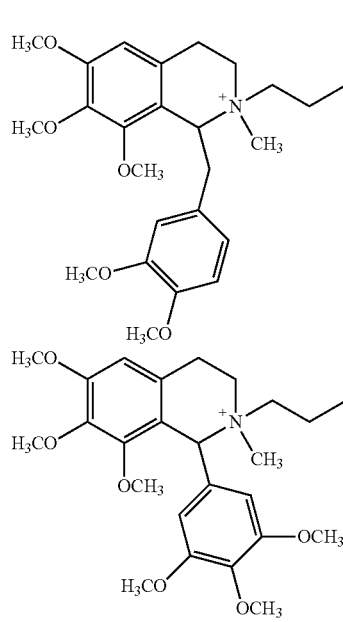
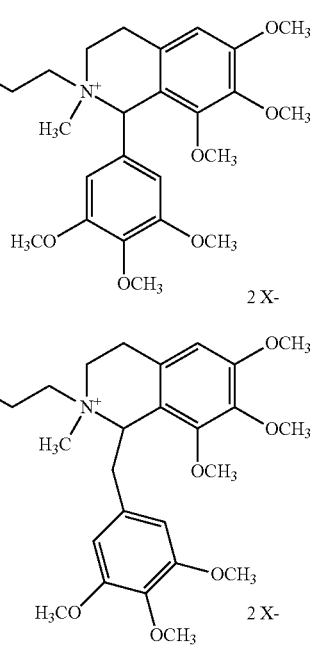
2 X-
including any stereoisomer thereof, or any combination, solvate, hydrate, metabolite, or prodrug thereof.
In various embodiments, the fumarate compound can be any of the following:
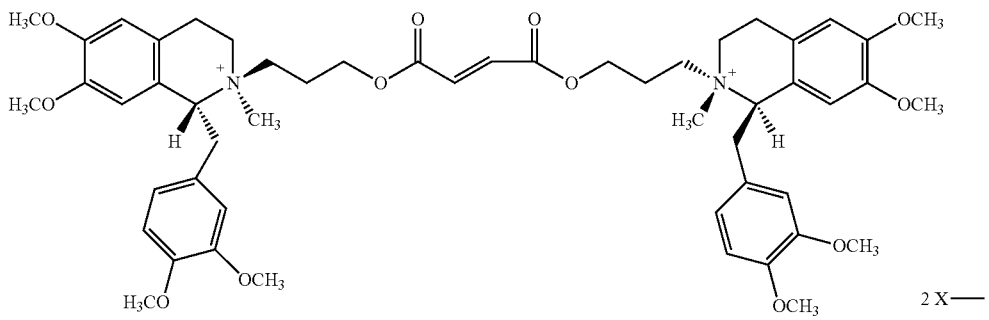
[NB 1025-68 (CW002)]
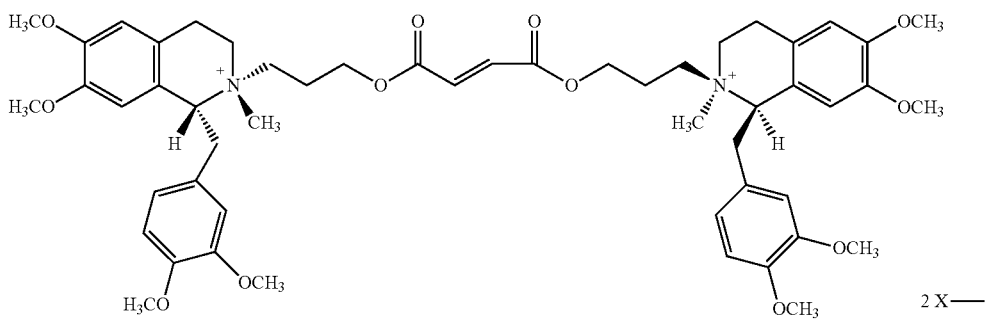
[NB 832-65 (CW003)]

-continued
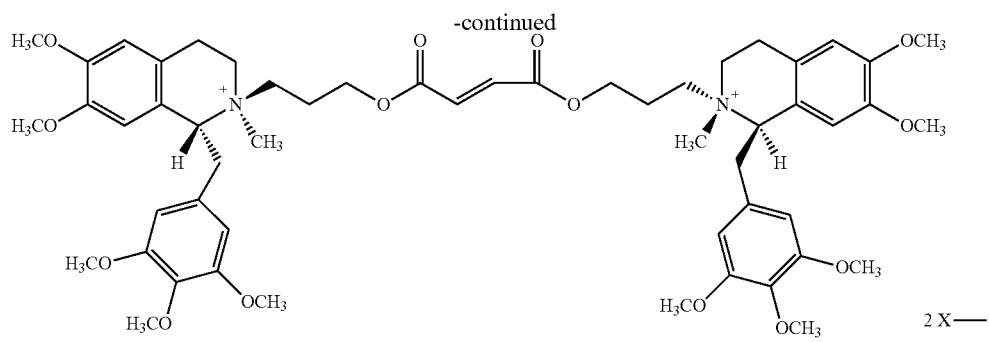
[NB802-17 (CW001)]
or any combination, solvate, hydrate, metabolite, or prodrug thereof.
In various embodiments, a compound of the invention can be any of the following acetylenedicarboxylates:
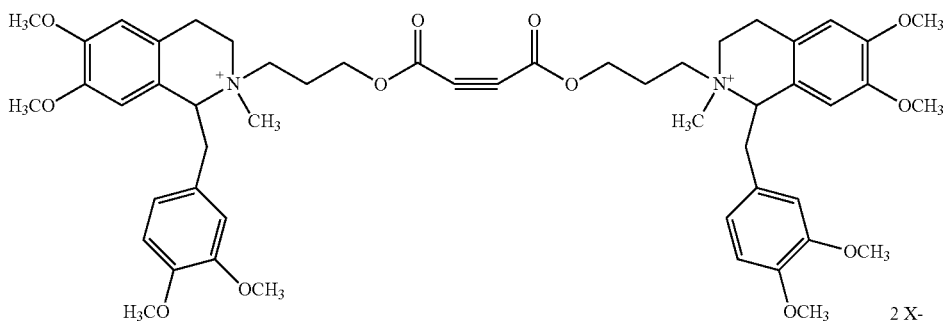
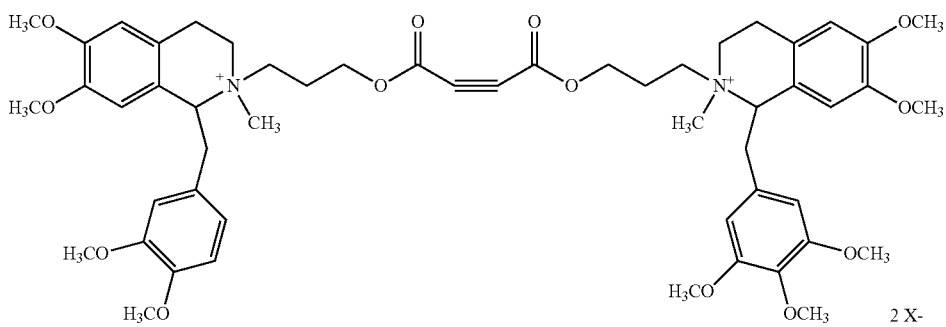
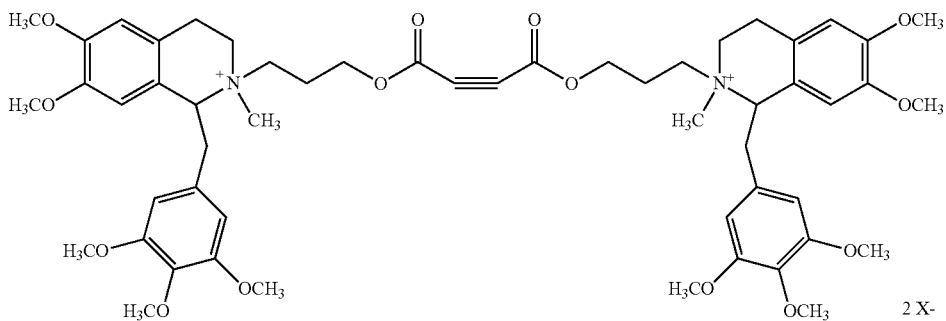

-continued
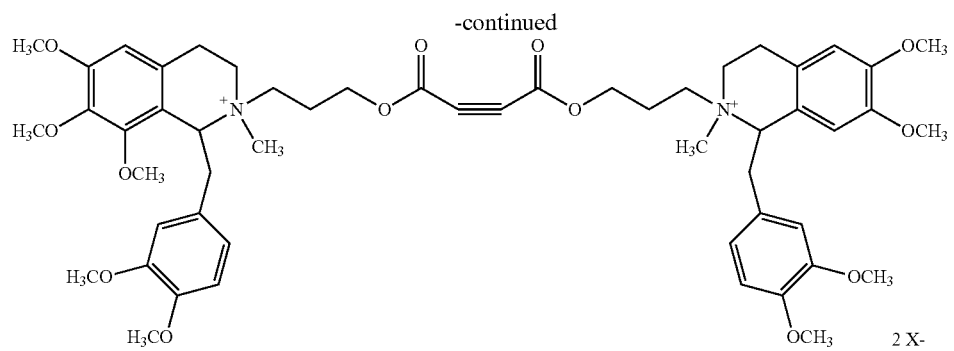
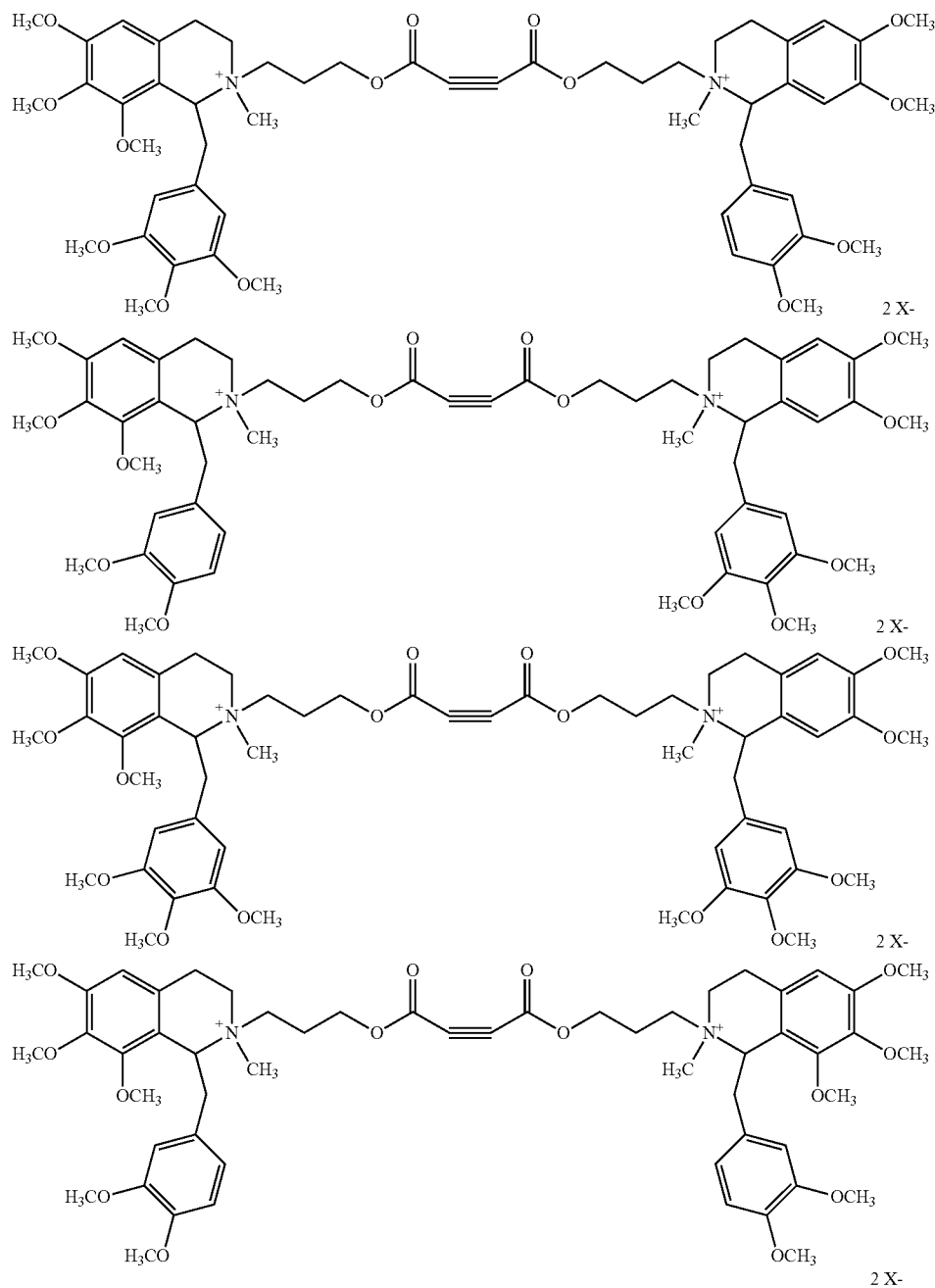

-continued
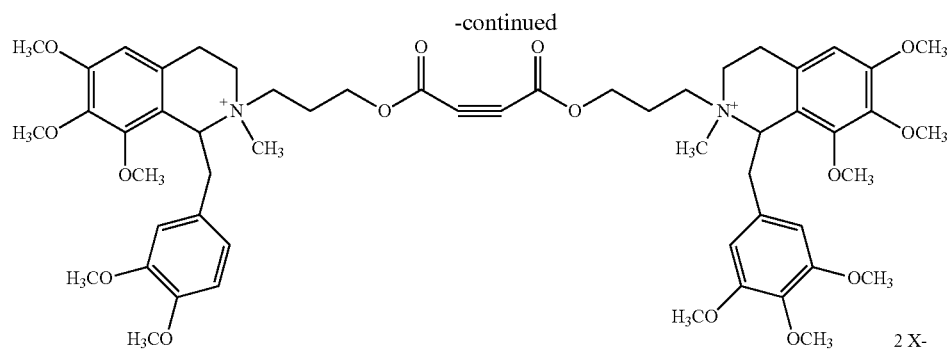
2 X-
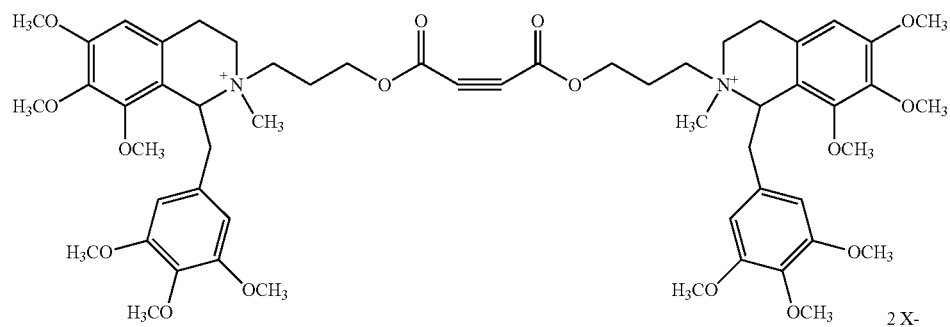
2 X-
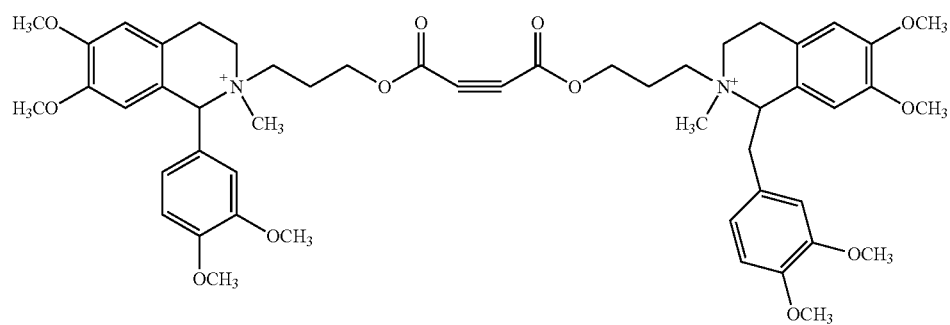
2 X-
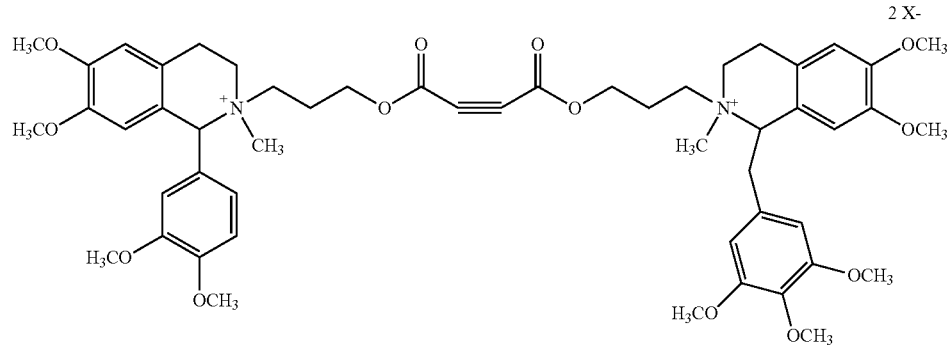
2 X-
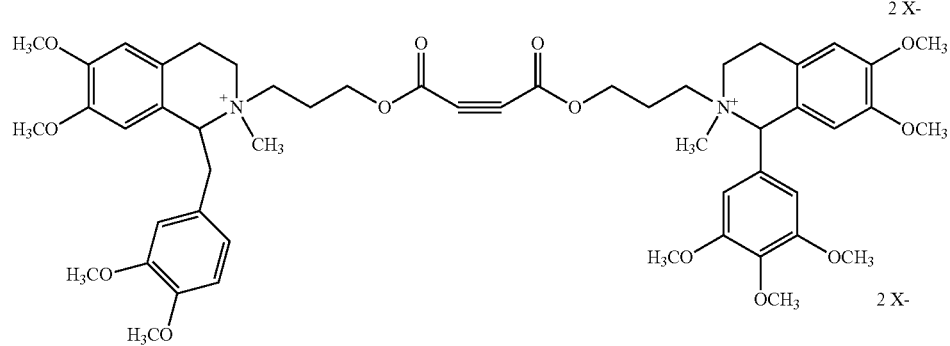
2 X-

-continued
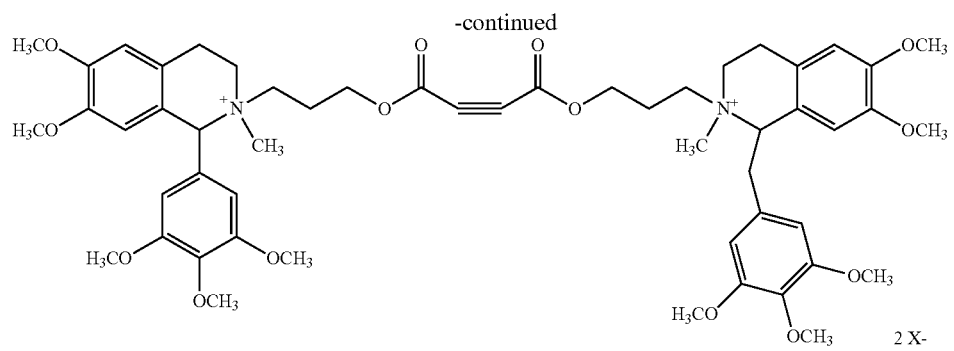
2 X−
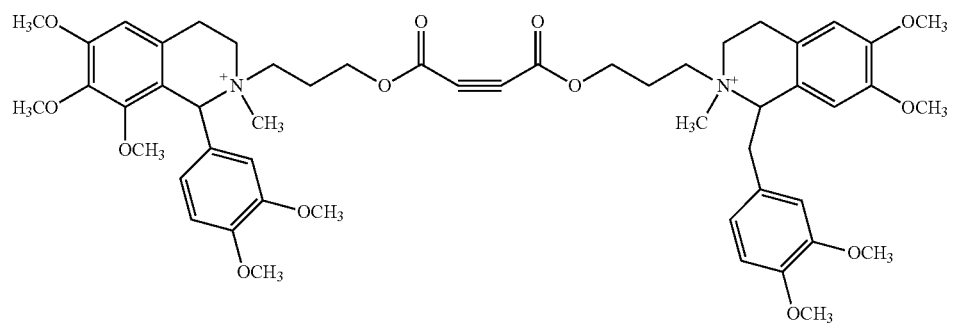
2 X−
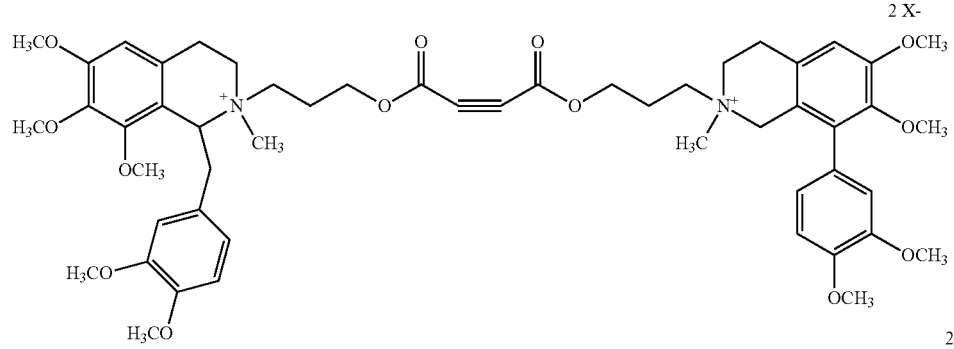
2 X−
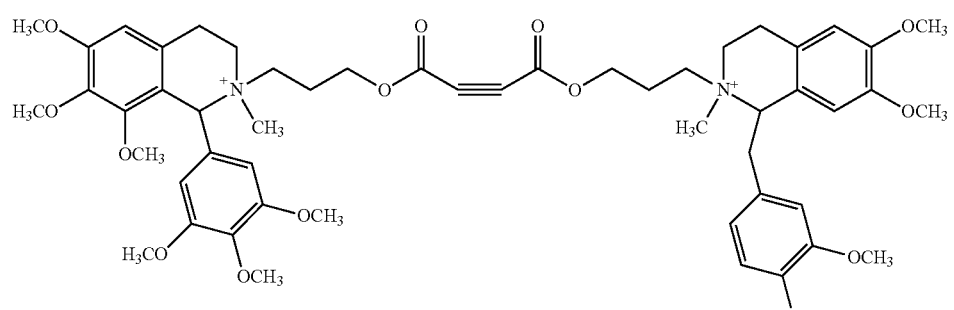
2 X−
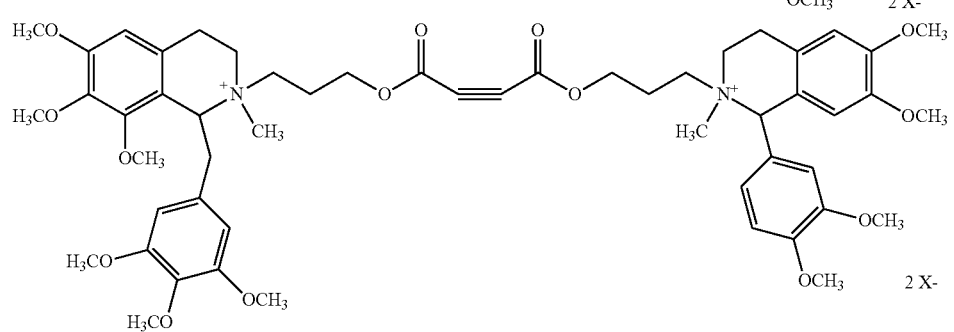
2 X−

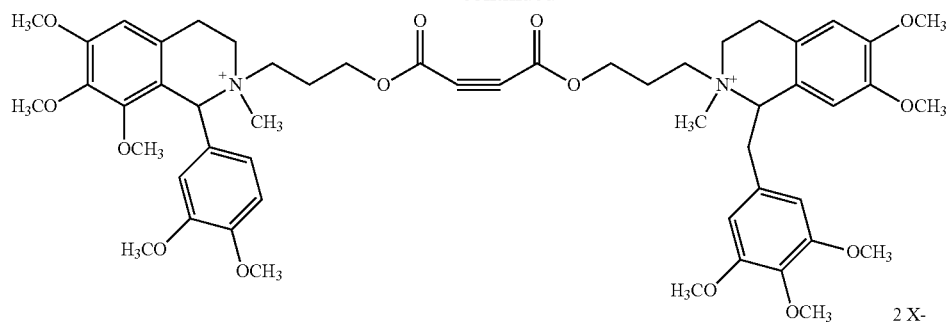
2 X-
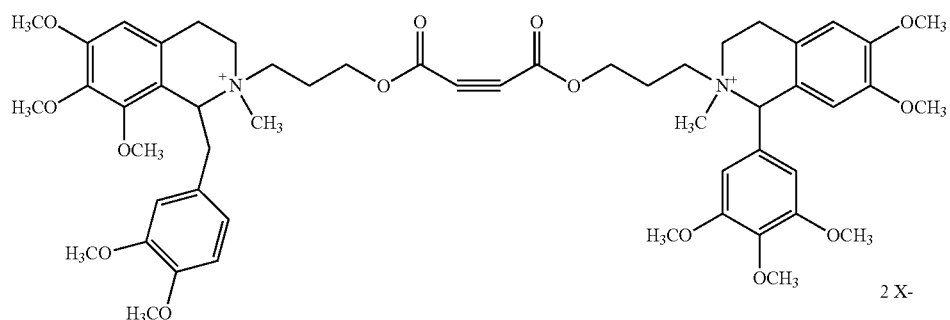
2 X-
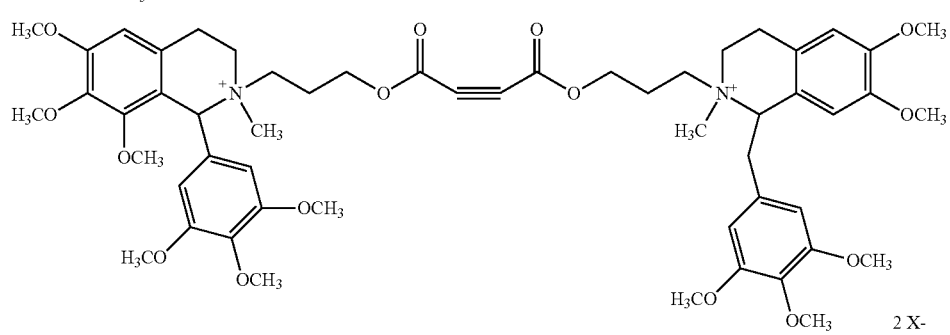
2 X-
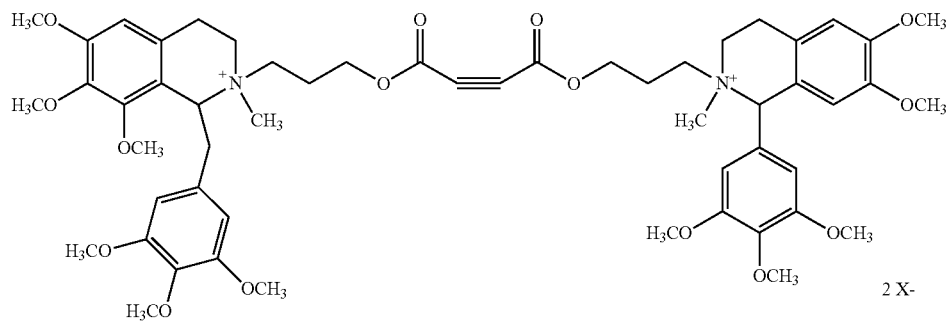
2 X-
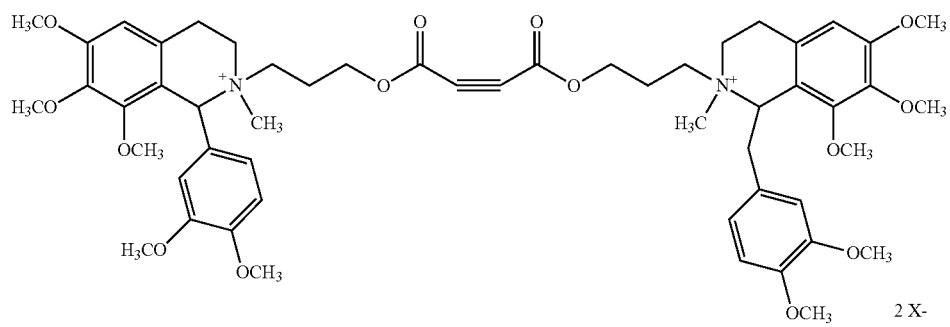
2 X-

-continued
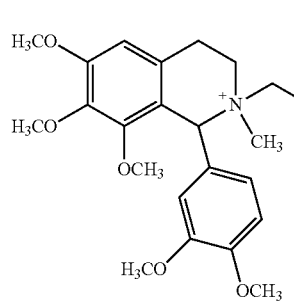 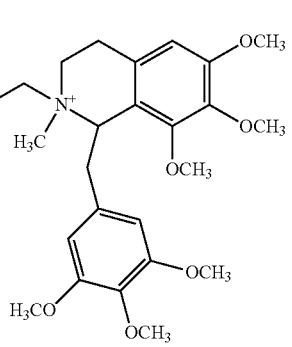
2 X−
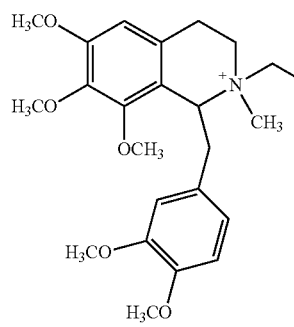 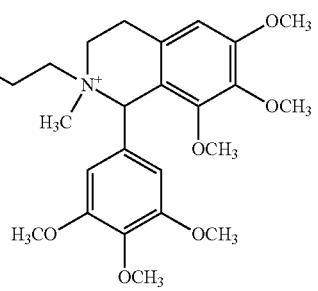
2 X−
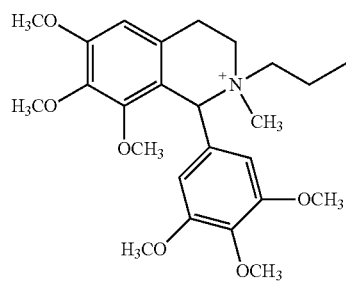 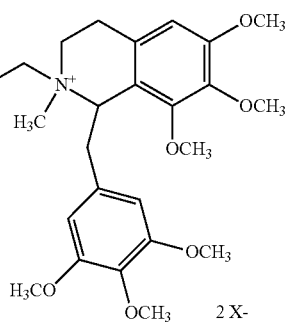
2 X−
including all stereoisomers thereof, or any combination, solvate, hydrate, or prodrug thereof.
In various embodiments, an acetylenedicarboxylate of the invention can be any of the following:
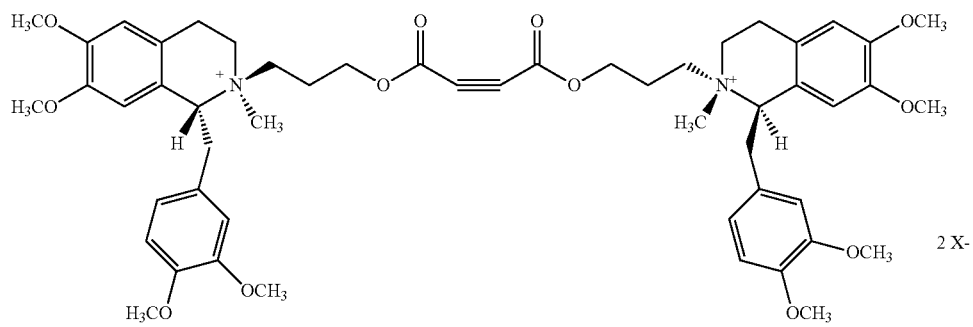
2 X−

-continued
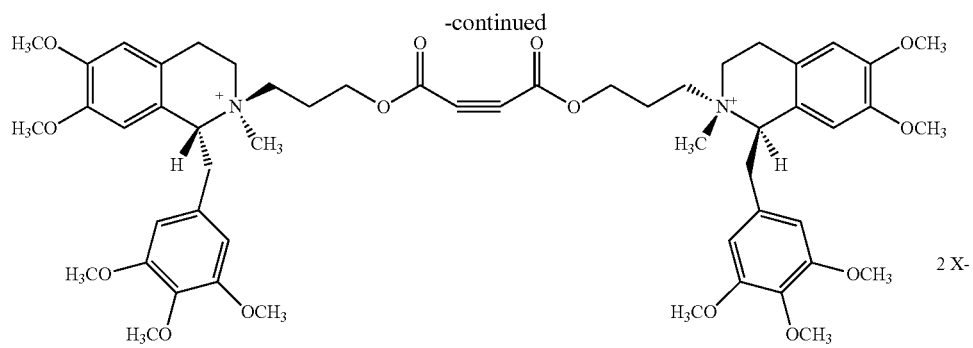
2 X⁻
or any combination, solvate, hydrate, or prodrug thereof.
Other neuromuscular blocking agents that can be employed include:
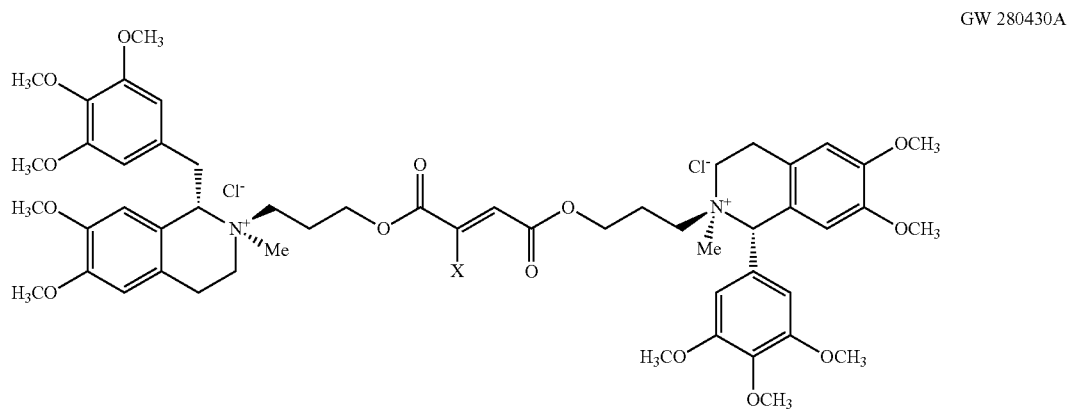
GW 280430A
(Z)-2-Chloro-4-{3-[(1S,2R)-6,7-dimethoxy-2-methyl-1-(3,4,5-trimethoxyphenyl)-1,2,3,4-tetrahydro-2-isoquinolinio]propyl}-1-{3{(1R,2S)-6,7-dimethoxy-2-methyl-1-[(3,4,5-trimethoxyphenyl)methyl]-1,2,3,4-tetrahydro-2-isoquinolinio}propyl}-2-butenedioate dichloride (the GW280430A compound),
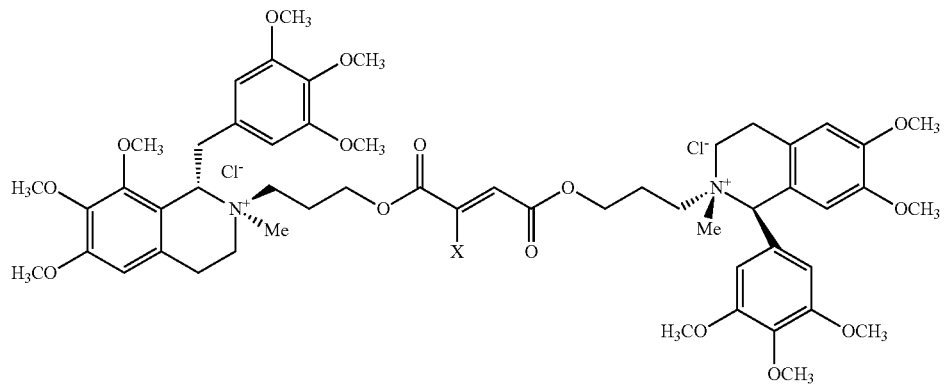
GW 353044A (Z)-2-Chloro-4-{3-[(1R,2S)-6,7-dimethoxy-2-methyl-1-(3,4,5-trimethoxyphenyl)-1,2,3,4-tetrahydro-2-isoquinolinio]propyl}-1-{3{(1R,2S)-2-methyl-6,7-dimethoxy-1-[(3,4,5-trimethoxyphenyl)methyl]-1,2,3,4-tetrahydro-2-isoquinolinio}propyl}-2-butenedioate dichloride (the GW353044A compound), 2,2-Difluoro-4-{3-[(1S,2R)-6,7-dimethoxy-2-methyl-1-(3,4,5-trimethoxyphenyl)-1,2,3,4-tetrahydro-2-isoquinolinio]propyl}1-{3-{(1R,2S)-6,7-dimethoxy-2-methyl-1-[(3,4,5-trimethoxyphenyl)methyl]-1,2,3,4-tetrahydro-2-isoquinolinio}propyl}-butenedioate dichloride, (Z)4-{3-[(1S,2R)-6,7-Dimethoxy-2-methyl-1-(3,4,5-trimethoxyphenyl)-1,2,3,4-tetrahydro-2-isoquinoliniolpropyl}-1-{3-{(1R,2S)-6,7-dimethoxy-2-methyl-1-[(3,4,5-trimethoxyphenyl)methyl]-1,2,3,4-tetrahydro-2-isoquinolinio}propyl}-2-fluoro-2-butenedioate dichloride 2,2-Difluoro-4-{3-[(1S,2R)-6,7-dimethoxy-2-methyl-1-(3,4,5-trimethoxyphenyl)-1,2,3,4-tetrahydro-2-isoquinolinio]propyl}-1-{3-{(1R,2S)-2-methyl-6,7,8-trimethoxy-1-[(3,4,5-trimethoxyphenyl)methyl]-1,2,3,4-tetrahydro-2-isoquinolinio}propyl}butanedioate dichloride;

or any combination, solvate, hydrate, or prodrug thereof.

Synthesis of Neuromuscular Blocking Agents

The neuromuscular blocking agents can be made by a variety of procedures. These procedures include those described herein, and those available in the art, which involve only use of only routine skill and knowledge of the ordinary practitioner of synthetic organic chemistry to make the neuromuscular blocking agents and the physiological cysteine solutions described herein.

Generally speaking, diesters of dibasic acids such as maleic, fumaric, and acetylenedicarboxylic acids can be prepared by formation of esters of both carboxylic acids, either concurrently or sequentially, with alcohols. The two esters can comprise either the same alcohol moiety, or differing alcohol moieties. In the present application, a diester is termed "symmetric" or "symmetrical" when both alcohol moieties are identical, and "asymmetric" or "asymmetrical" when the two alcohol moieties are not identical.

Generally speaking, diesters of dibasic acids such as maleic, fumaric, and acetylenedicarboxylic acids can be prepared by formation of esters of both carboxylic acids, either concurrently or sequentially, with alcohols. The two esters can comprise either the same alcohol moiety, or differing alcohol moieties. In the present application, a diester is termed "symmetric" or "symmetrical" when both alcohol moieties are identical, and "asymmetric" or "asymmetrical" when the two alcohol moieties are not identical.

Condensation of a diacid with an alcohol can be carried out using substantially any of the carboxyl activation procedures known in the art. When the dicarboxylic acid can cyclize to form a cyclic anhydride, as in the case of maleic acid, a cyclic anhydride can be used. In all cases, activated carboxyl groups such as acyl chlorides and activated esters (e.g., N-hydroxysuccinimide esters, N-hydroxybenztriazole esters, and the like) can be used. When a cyclic anhydride is used as the activated carboxyl species, only one mole of alcohol can react in that step, providing a diacid-monoester species. This intermediate can be activated and condensed with a second mole of an alcohol, the same or different, to provide a diester. For example, see Synthetic Scheme 1, below. This approach can be used to prepare both symmetric and asymmetric diesters for those diacids having sterically accessible cyclic anhydride forms.

Condensation of maleic cyclic anhydride (XI), wherein a dotted bond indicates a double bond, with a first isoquinolylalkanol (XII) yields monoester (XIII). The free carboxyl group of monoester (XIII) can be activated by means known in the art, such as by formation of an activated ester, e.g., with N-hydroxysuccinimide/dicyclohexyl-carbodiimide, to provide activated ester (XIV) wherein A represents a carboxyl activating moiety, which is then condensed with a second isoquinolylalkanol (XV) which can be the same as or different from isoquinolylalkanol (XII) to provide a symmetric or asymmetric compound of formula (I).

Synthetic Scheme 1: Reaction of cyclic anhydrides with isoquinolylalkanol

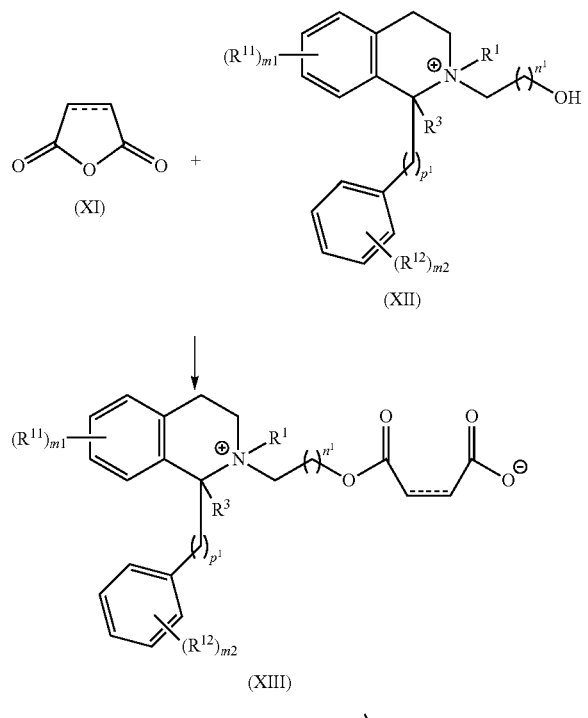

-continued
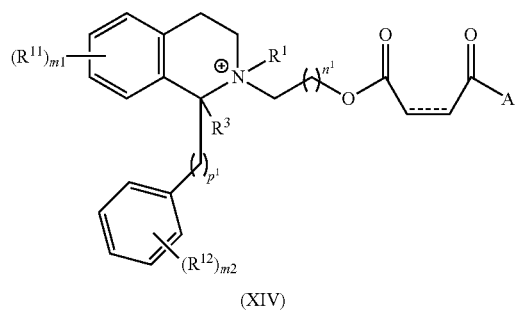
(XIV)
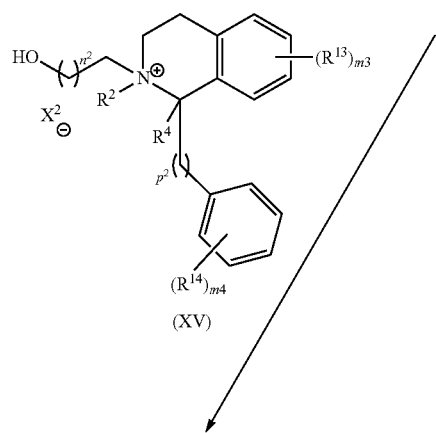
(XV)
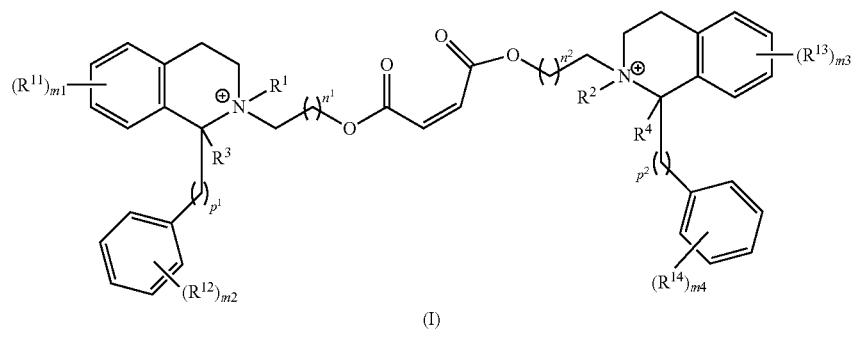
(I)

Whether or not a cyclic anhydride form is sterically accessible to a diacid, carboxyl activation procedures and intermediates that do not involve formation of a ring can be used. For example, for all of maleic, fumaric, and acetylenedicarboxylic acids, formula (XXI) wherein the dotted lines indicate a Z or E double bond, or a triple bond, formation of bis acyl halides (e.g., bis acyl chlorides) can be employed to provide a reactive intermediate. Similarly formation of activated esters can be used to provide a reactive intermediate. If a symmetrical diester is desired, an activated diacid can be condensed with an excess of the alcoholic reagent to provide a diester incorporating two moles of the alcohol moiety. For example, see Synthetic Scheme 2, below.

Synthetic Scheme 2: Reaction of activated diacids with isoquinolylalkanol

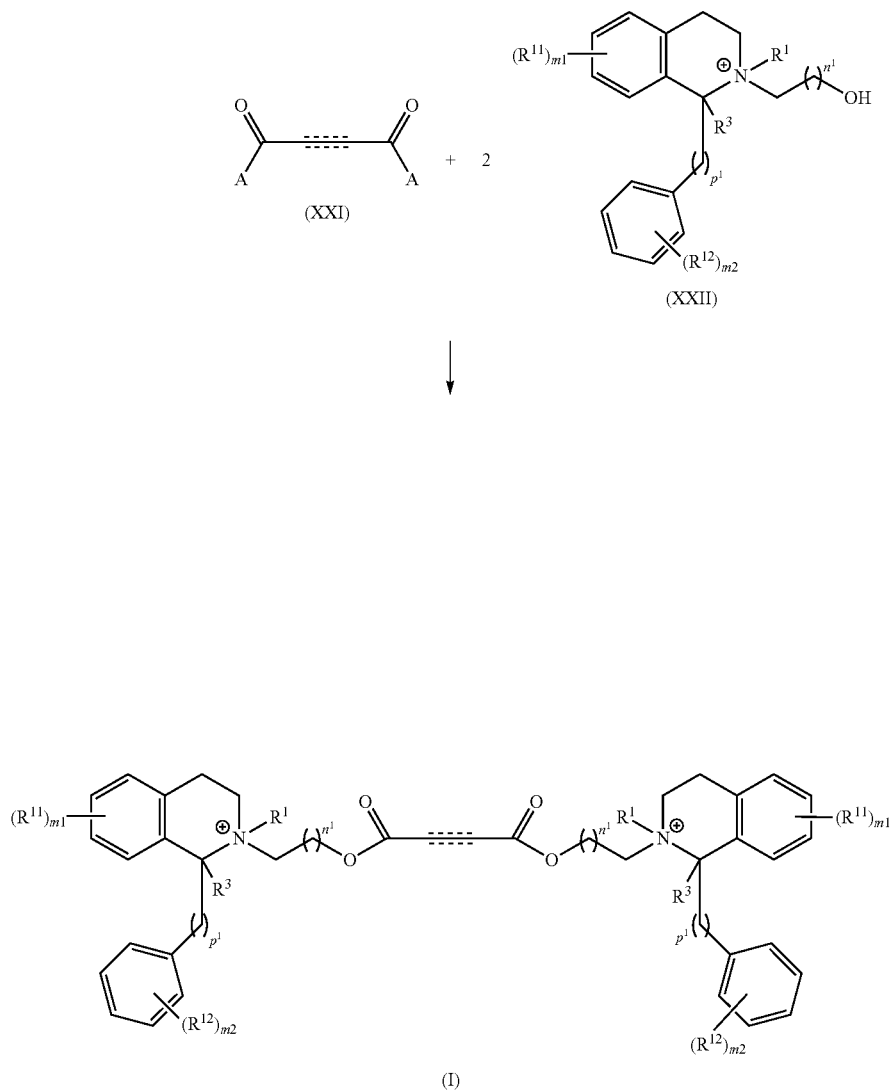

A carboxyl-activated diacid (XXI), which can be a bis-carboxyl-activated form of maleic, fumaric, or acetylenedicarboxylic acid, is condensed with an isoquinolylalkanol, preferably at least two molar equivalents thereof, to provide a symmetric compound of formula (I) of the invention. As described above, carboxyl activation can employ any of the many methods well known in the art. The use of less than two equivalents of the isoquinolylalkanol (XXII) will result in formation of significant quantities of the corresponding monoester, which can be separated and used in a second esterification step, using a different isoquinolylalkanol if desired, to prepare an asymmetric compound of formula (I).

Synthesis Scheme 3: Stepwise preparation of diesters
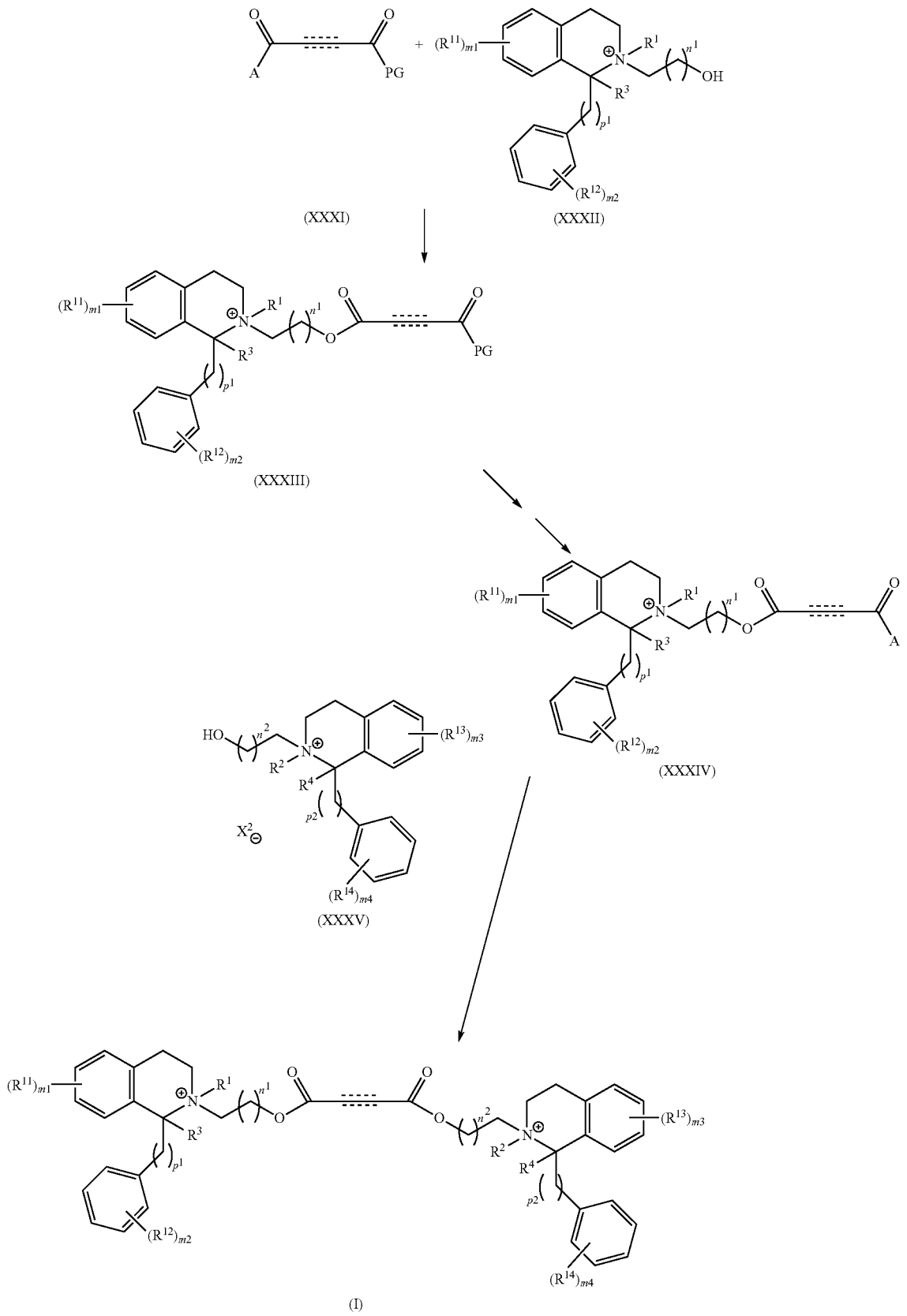

If an asymmetric diester is desired, particularly using a diacid for which a cyclic anhydride form is not sterically available, a more selective route can be employed, such as is shown in Synthetic Scheme 3, above.

Starting with a mono-protected maleic, fumaric, or acetylenedicarboxylic acid, as are known in the art, the unprotected carboxyl group can be activated for ester formation. A suitable protecting group PG blocks one of the two carboxylic acid groups. The protecting group PG is suitable for removal under conditions do not affect the other groups in intermediate (XXXIII). For example, starting with a mono-t-butyl, mono-activated maleate, fumarate, or acetylenedicarboxylate, the PG group in (XXXIII) will thus be t-butyl. As is known in the art, a t-butyl ester can then be cleaved with mild acid to yield the compound with a free carboxylic acid group at that position (not shown), which can then be activated using standard procedures (intermediate (XXXIV)), and coupled with an isoquinolylalkanol (XXXV) that can be different from (XXXII), to yield an asymmetric compound of formula (I).

Accordingly, in various embodiments, the invention provides a method of synthesis of a maleate compound of the invention, comprising contacting a compound of formula (III)

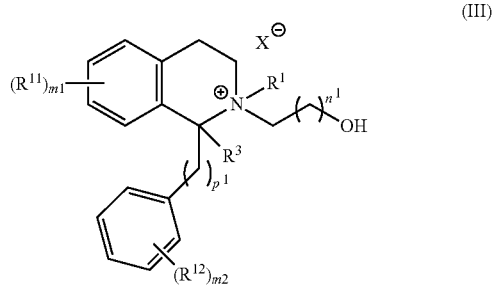

and maleic anhydride, to provide a compound of formula (IIIA)

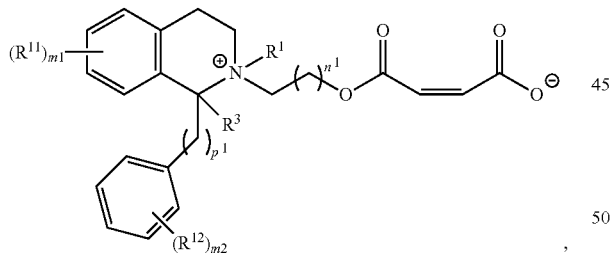

or any salt thereof, then, contacting the compound of formula (IIIA) and an independently selected compound of formula (IIIB)

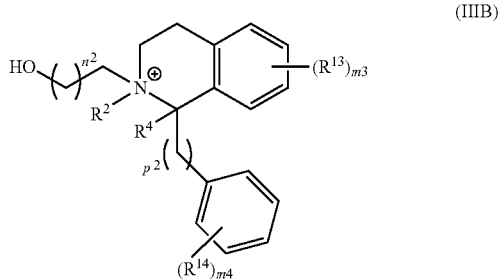

under conditions suitable to bring about ester formation, to provide the maleate compound of claim 2.

More specifically, all of $R^{11}$, $R^{12}$, $R^{13}$ and $R^{14}$ can be methoxy, m1 and m3 can each independently be 2, 3, or 4, and m2 and m4 can each independently be 2 or 3.

In various embodiments, the invention provides a method of synthesis of a compound of the invention, such as a fumarate, maleate, or acetylenedicarboxylate, comprising contacting a compound of formula (III)

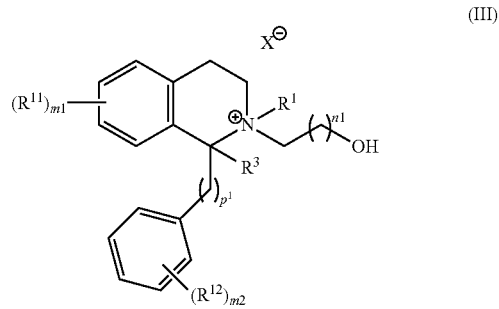

and an activated diacid of formula (IV)

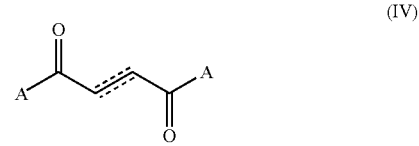

wherein the dashed lines indicate a double bond or a triple bond, wherein each A is each independently a carboxyl activating group, under conditions suitable to bring about ester formation, to provide the compound of formula (IA)

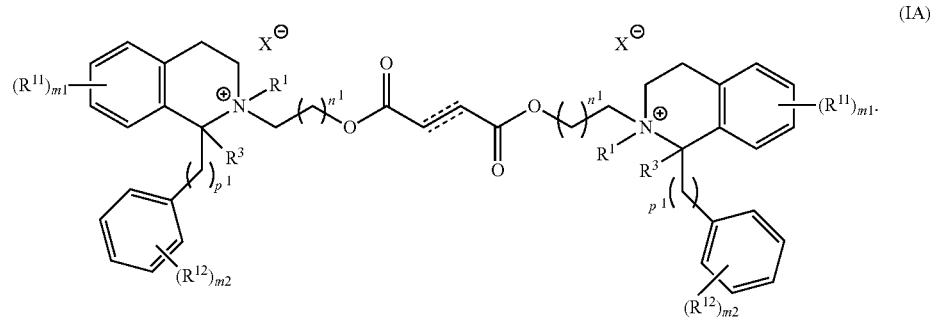

More specifically, $R^{11}$ and $R^{12}$ can be methoxy, m1 can be 2, 3, or 4, and m2 can be 2 or 3.

In various embodiments, the invention provides a method of synthesis of a compound of claim 1, wherein PG is a carboxy-protecting group and A is a carboxy-activating group, comprising contacting a mono-protected mono-activated diacid of formula (XXXI)

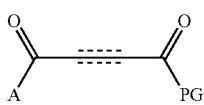

(XXXI)

and an isoquinolylalkanol of formula (XXXII)

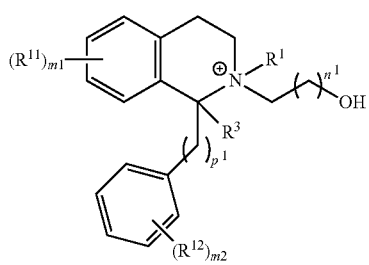

(XXXII)

under conditions suitable to bring about ester formation, to provide a compound of formula (XXXIII)

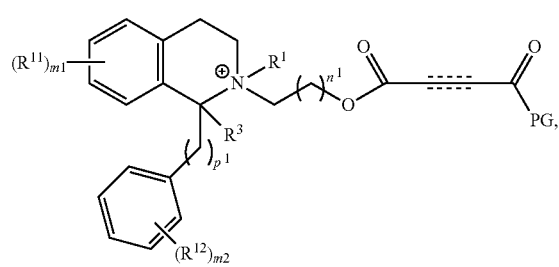

(XXXIII)

then, removing protecting group PG to provide a free carboxylic acid;
then, activating the free carboxylic acid to provide a compound of formula (XXXIV)

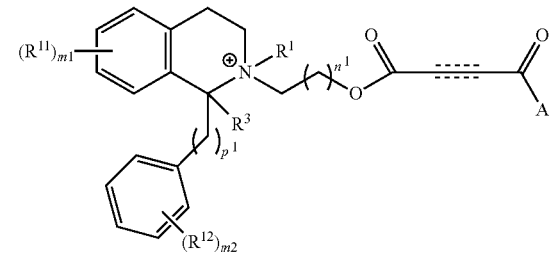

(XXXIV)

then, contacting the compound of formula (XXXIV), and a compound of formula (XXXV)

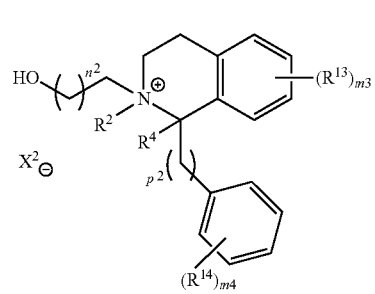

(XXXV)

under conditions suitable to bring about ester formation, to provide a compound of formula (I)

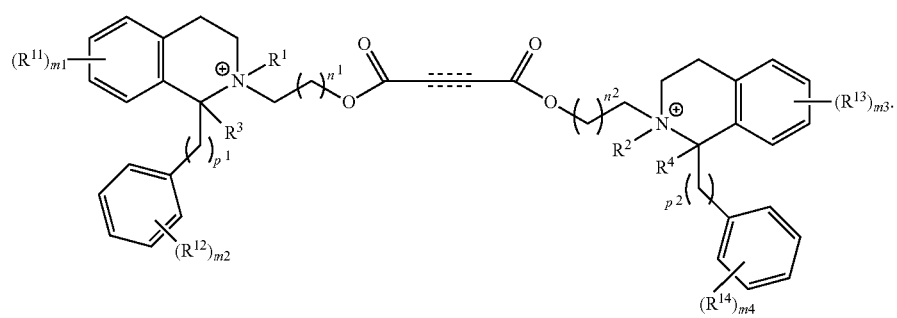

(I)

More specifically, $R^{11}$ and $R^{12}$ can be methoxy, m1 can be 2, 3, or 4, and m2 can be 2 or 3.

Some of the neuromuscular blocking agents can also be made as described in U.S. Pat. No. 6,187,789 and Boros et al., J. Med. Chem. 46:2502-15 (2003), which are incorporated herein by reference.

The pharmacological activity of the compounds of the invention can reside in the cation. Hence, the nature of the anion A⁻ is relatively unimportant. However, for therapeutic purposes, A⁻ is preferably pharmaceutically acceptable to the recipient of the compounds. Examples of pharmaceutically acceptable anions include iodide, mesylate, tosylate, bromide, chloride, hydrogen sulphate, sulphate$^{-2}$, phosphate$^{-3}$, hydrogen phosphates, acetate, besylate, succinate$^{-2}$, maleate, naphthalenesulphonate and propionate. Both pharmaceutically acceptable salts and salts that are not thus acceptable may be useful for isolating and/or purifying the compounds of the invention. The pharmaceutically unacceptable salts may also be useful in that they may be converted into acceptable salts by techniques available in the art.

Pharmaceutical Compositions and Uses

The neuromuscular blocking agents can be present within various compositions. These compositions can be employed to induce neuromuscular blockade in patients as needed. The neuromuscular blocking agents are used, for example, during surgery, for surgical anesthesia, for intubation of the trachea, or during electroshock therapy.

In some embodiments, the neuromuscular blocking agents, administered by injection in a suitable solution, produce neuromuscular blockade of sufficient completeness to enable the agent to effectively be used as an adjunct to anesthesia in major surgery. In various embodiments, an effective amount of a neuromuscular blocking agent for administration to a human patient is about 0.01 to 20.0 mg/kg of body weight, or about 0.01-10 mg per kg patient bodyweight. More specifically, in various embodiments, the effective amount is about 0.02 to 2.0 mg/kg of body weight, or about 0.1-1 mg per kg patient bodyweight, where the effective amount of neuromuscular blocking agent is based on the weight of the di-cation which is the active ingredient. The dosage for intramuscular administration is typically two to eight times the intravenous dose.

The neuromuscular blocking agents can be administered in a manner known to the anesthesiologist or surgeon of ordinary skill in the art, using the methods and apparatus well known for this procedure in surgery. For example, the neuromuscular blocking agent(s) may be administered parenterally, e.g., by intramuscular or intravenous injection of a solution.

The neuromuscular blocking agents can be provided in a composition comprising the neuromuscular blocking agent(s) and a pharmaceutically acceptable excipient. The composition can, for example, be adapted for parenteral administration to a human patient, comprising an injectable solution of the agent in a suitable biocompatible solvent. In various embodiments, an injectable solution of a neuromuscular blocking agent in a suitable solvent comprises about 1 mg/mL to about 10 mg/mL of the compound per dose of the injectable solution. The solution can be administered via syringe, via intravenous drip, or via any of the techniques well known to the practitioner of the art.

In various embodiments, a suitable biocompatible solvent comprises sterile, pyrogen-free water. The solvent can further comprise isotonic NaCl, or other tonicity adjustment substances. In various embodiments, the suitable biocompatible solvent can comprise alcohol, a polyethylene glycol, DMSO, or any mixture thereof, which can be neat or can be in a mixture with water.

Neuromuscular blocking agents may, to some extent, be unstable over prolonged storage in alkaline medium. Accordingly, a dosage form containing the neuromuscular blocking agent(s) can be adjusted to an acidic pH for stabilization. In various embodiments of a solution dosage form of the invention, the pH of the solution is about pH 2.0 to about 5.0 or about pH 2.5 to about 3.5. In various embodiments, the dosage form can be adapted for frozen storage, such as by packaging in containers that can withstand freezing, bearing freeze-resistant labeling, and the like.

The invention provides neuromuscular blocking agents, for example, in a kit where the blockade effects are reversible by administration to the patient of an effective amount of a thiol compound. Thus, the kit can include a container with a thiol compound, and a container with a composition that includes one or more neuromuscular blocking agents. An outstanding feature of the present invention is the ready reversibility of the neuromuscular blockade effects of some of the neuromuscular blocking agents described herein by administration to the patient, such as by intravenous administration, of a thiol compound. Thus, the kit can include a thiol compound such as L-cysteine or a pharmaceutically acceptable salt thereof, D-cysteine or a pharmaceutically acceptable salt thereof, or glutathione or a pharmaceutically acceptable salt thereof, or a stereoisomer of glutathione or a pharmaceutically acceptable salt thereof, or a combination thereof.

As discussed herein, without wishing to be bound by theory, the inventor believes that inactivation of the neuromuscular blockade effects by a thiol compound takes place via an intermolecular reaction in vivo of the neuromuscular blocking agent and the thiol, producing a reaction product therebetween. Each of the classes of fumarates, maleates, and acetylenedicarboxylates neuromuscular blocking agent are believed to be susceptible to this reaction, and it has been found that the neuromuscular blockade effects of specific fumarates (e.g., CW 002) and maleates (e.g. CW 011) are reversible by administration of thiol compounds such as cysteine (L or D) or glutathione. It has also been found that the neuromuscular blockade effect of a succinate neuromuscular blocking agent is not reversible by administration of a thiol compound. These observations support the mechanistic theory, and lead the inventor to the prediction that acetylenedicarboxylates of the invention will be both potent and reversible neuromuscular blocking agents.

The thiol compound used for reversal of the neuromuscular blockade can be L-cysteine or a pharmaceutically acceptable salt thereof, D-cysteine or a pharmaceutically acceptable salt thereof, or any mixture thereof, or glutathione or a pharmaceutically acceptable salt thereof, or a stereoisomer of glutathione or a pharmaceutically acceptable salt thereof, or a combination thereof.

In various embodiments, the blockade is reversible within about 2-5 minutes after administration of the thiol compound to the patient following induction of the neuromuscular blockade. Rapid reversal can be advantageous in carrying out surgical procedures, as it allows mechanical respiration to be used for only the necessary period of time, insomuch as the blockade can inhibit the action of the patient's diaphragm in natural respiration. Accordingly, the thiol compound such as cysteine (L or D) or a salt thereof can be administered to the patient immediately following a surgical procedure for which a compound of formula (I) had been previously administered to the patient. For example, the thiol compound used to immediately reverse the neuromuscular blockade following surgery can comprise cysteine or a salt thereof wherein the cysteine or salt thereof is administered at a dose of about 10 mg/kg to about 50 mg/kg on a free base basis. More specifically, the cysteine or salt thereof can be D-cysteine hydrochloride. Use of a D-cysteine salt can avoid some of the unwanted side-effects that may be experienced when using certain doses of an L-cysteine salt. A solution of L-cysteine, D-cysteine, glutathione, a glutathione stereoisomer, or a combination thereof can be adjusted to a pH of about 5-6 prior to administration to the patient to reverse the neuromuscular blockade.

Accordingly, the invention provides a use of a neuromuscular blocking agent for creating neuromuscular blockade, wherein the blockade is reversible by administration of a thiol compound.

The invention is further illustrated by the following non-limiting Examples.

EXAMPLE 1

Manufacture of Physiological Cysteine Solutions

This Example illustrates desirable compositions, pH ranges and storage conditions for physiological solutions of cysteines.

To develop a stable cysteine formulation for physiological administration, several factors were considered. First, the natural pH of cysteine hydrochloride solutions at concentrations of 50 mg/ml or more in 0.9% saline is very low—about pH 0.8 to pH 1.0. Second, when administering cysteine, venous irritation or trauma can be avoided by administering cysteines solutions with pH values of 4.0-5.0. Third, cysteine is not soluble at concentrations greater than 50 mg/ml in its base form, and this concentration is generally too dilute for convenient administration to a patient. Instead, a solution containing 150-200 mg/ml or more cysteine is much more convenient for intravenous injection.

This Example illustrates what types of cysteine formulations can be made and stored under conditions that avoid precipitation, followed by adjustment of the pH of these cysteine formulations for intravenous administration to patients.

Materials and Methods

The following supplies and equipment were employed:
1. Ethylenediaminetetraacetic acid calcium disodium salt hydrate, Sigma-Aldrich (PN 340073, lot 01929 KH). Karl Fisher result on this lot was 10.2% water.
2. L-Cysteine Hydrochloride Monohydrate, Ajinomoto Lot R009E015, drum 0010. Loss on drying for this lot is 12.2% water as previously determined at Trade Place. The purity is 100% per the CoA.
3. 6N Sodium Hydroxide, ACS Grade, Ricca Chemicals Lot 4708124.
4. Sterile Water for Injection (SWFI), Baxter Lot G061788, USP Grade.
5. Class A volumetric glassware.
6. Mettler AT 201 analytical balance, equipment ID INS-00910.
7. Radiometer Analytical; Combined pH Electrode, Calomel PN=E1GM333; Type=pHC4006-9, equipment ID INS-00751.
8. Milli-Q water purification system, equipment ID INS-C1005
9. Fluke digital thermometer, equipment ID INS-00936
10. Temperature controlled water bath, Lauda RC 20, INS-00675
11. Ultra pure nitrogen gas, number, UN1066
12. 0.22 micron PVDF filters, 500 mL receiver bottle, Millipore, SCGVU05RE, LotR7BN05327
13. Laminar flow hood, equipment ID, INS-C0318
14. Sterile 5 mL syringes and 18 gauge needles.

Proposed formulations of the L-Cysteine Hydrochloride drug product were prepared at different pH values (1.8 to 2.3), stored for various time periods under different conditions and then neutralized to pH 4-6 using Tris buffer. The pH of these L-Cys-HCl samples was evaluated and the impact of temperature on pH measurement was also observed.

Preparation of L-Cysteine HCl at pH 1.95:

A solution of L-Cysteine HCl at a concentration of 225 mg/mL containing 0.2 mg/ml CaNa$_2$EDTA was made using sterile water for injection (SWFI). A sterile plastic pipette attached to a nitrogen supply hose was inserted into the 500 mL bottle with gentle stream of nitrogen for approximately 1 hour prior to use. Approximately 300 mL of degassed water was added into a clean glass beaker with a stir bar. Calcium disodium ethylenediamine tetra acetate hydrate (112.9 mg) was added and the solution stirred until all visible solid had dissolved. A total of 128.1 grams of L-Cysteine HCl Monohydrate was slowly added with stirring until the solution appeared clear and all solid had dissolved completely. The pH was adjusted to 1.95±0.05 with 6.0N sodium hydroxide. The weight of 6N NaOH added to adjust the pH to 1.95 was 80 grams. The solution was then transferred to a volumetric flask quantitatively and the volume was adjusted to 500 mL with degassed water. The flask was mixed by inverting multiple times and the contents filtered it through a 0.22 micron PVDF filter under vacuum. The solution appearance and pH of the solution were measured after filtration. The filtrate was sparged for about 1 hour with nitrogen and the bulk filtered solution was degassed for about 1 hour and 16.5 mL aliquots were dispensed into 20 cc vials with a repeat pipettor. The vials were stoppered with 20 mm grey rubber stopper, and sealed by crimping with aluminum caps. A total of 29 vials were made and then stored at −20° C. in the upright configuration.

Mixing Experiments

The pH 1.95 L-Cys HCl formulation was mixed with buffering agent TRIS to raise the pH to physiologically acceptable levels the next day by adding 3.6 M Tris to vials (16.5 mL) of pH 1.95 L-Cys HCl. The mixing was performed by injecting 4.0 mL of Tris into the vials using a 5 mL sterile syringe and 18 gauge needles. In the first experiment, the pH was measured approximately 2 hours after mixing. In the second experiment, fresh aliquots were taken from the sealed vials every 2 hours for an 8 hour period and the pH was measured. In the third experiment, a vial was thawed after 10 days of storage at −20° C., mixed and the pH measured.

In another experiment, two vials were taken from the freezer, thawed and pooled. Aliquots (4.125-mL) of this L-Cys-HCl solution were placed into 6 test tubes using a calibrated volumetric pipetting device. The pH in each tube was adjusted with either HCl or NaOH to within ±0.05 of the following pH values, 1.7, 1.8, 1.95, 2.1, 2.2, and 2.3. The volume required to hit the target pH values was recorded. These solutions were then mixed with 3.6M Tris.

The Tris neutralizing diluent was prepared by pooling two vials of 436 mg/mL Tris (3.6 M) thawed to room temperature from −20° C. storage. A total of 1.0 mL of the Tris was added to each pH adjusted vial of the L-Cys-HCl. The solutions in the vials were mixed and the pH values were measured at 25° C.±2° C. Temperature was maintained using a circulating water bath and pH measured with a Calomel pH probe. If the pH was not between 4.5 and 5.5 more Tris was added until the pH was in range. If the pH was greater than 5.5, no further Tris was added.

The final pH of 1.0 mL Tris neutralized samples was plotted versus the starting pH of the L-Cys-HCl solution on the y and x axes, respectively.

pH Measurement on Historical Samples

The pH or vials prepared as described above and stored under various conditions was measured at 25° C.±2° C. where temperature was maintained by using a circulating water bath and pH measured with a Calomel pH probe. The WFJ-C0002 samples had been stored at 22.5° C. for approximately 6 months. The WFJ-C0003 samples had been stored at −20° C. for approximately 5 months. One vial from the WFJ-C0017 had been stored at −20° C. for approximately 3 months was also tested.

Temperature and pH Measurements

An experiment was performed to investigate the relationship of temperature relative to pH measurement. In this experiment, the pH meter was calibrated at 25° C.±2° C. between the range of 1.679 and 4.005 using the IUPAC Reference Standard Solutions. The temperature was changed using the circulating water bath and pH measurements were taken at 15° C., 20° C., 25° C. and 30° C. The data recorded were for a pH 1.679 IUPAC Standard Solution and for an aliquot of WFJ-C0007 GLP Filled L-Cys-HCl solution.

Results

Compounding pH 1.95 L-Cys-HCl

At the time of compounding, the final pH of the L-Cys-HCl formulation just prior to aliquoting into vials was pH 1.96 and the solution appeared clear, colorless and free from visible particles. The same observation was made when several other pH measurements were made on L-Cys-HCl samples stored frozen for up to 10 days. One vial was thawed on day 9 and stored at 5° C. overnight while another was taken from the freezer at day 10 and thawed just prior to pH measurement. The pH measured in the two separate vials was 1.97. All vials measured were clear and colorless free from visual particles.

Care was taken regarding temperature monitoring of the samples and after each measurement, that the 1.679 and 4.005 IUPAC Reference Standard Solutions exhibited pH measurements within 0.02 pH units of their assigned values. In addition, pH readings were allowed at least one minute to stabilize prior to recording in the notebook.

within the target pH range of 4.5 to 5.5. Results from mixing whole vials confirmed this observation.

TABLE 1 pH Adjustment of L-Cys-HCl followed by Mixing with 3.6M Tris pH 8.0

| Tube No. | uL HCl Added | uL NaOH Added | Total mL of TRIS Added | Starting pH | pH with 1 mL TRIS | Final pH |
|---|---|---|---|---|---|---|
| 1 | 90 | 0 | 1.250 | 1.68 | 3.64 | 4.55 |
| 2 | 50 | 0 | 1.125 | 1.81 | 4.15 | 4.58 |
| 3 | 0 | 0 | 1.000 | 1.97 | 4.71 | 4.71 |
| 4 | 0 | 60 | 1.000 | 2.10 | 5.68 | 5.68 |
| 5 | 0 | 110 | 1.000 | 2.21 | 6.52 | 6.52 |
| 6 | 0 | 155 | 1.000 | 2.29 | 6.87 | 6.87 |

The day after compounding the L-Cys-HCl, one whole vial was taken from storage at −20° C., mixed with an approximate one-quarter volume of 3.6M Tris and the pH of this mixed solution was measured. The pH of the whole 16.5 mL vial taken approximately two hours after mixing with 4.0 mL of 3.6M Tris was pH 4.60. In a repeat experiment performed two days after compounding, using fresh aliquots taken at two hour intervals over an eight hour period, the pH ranged from 4.57 to 4.59. All samples appeared clear and colorless free from visible particles up to 24 hours after mixing and storage on the lab bench. Prior to taking the each pH measurement, the pH meter was calibrated with appropriate standards.

pH Measurement on Historical Samples of L-Cys-HCl

Table 2 shows pH measurements on historical samples of L-Cys-HCl that were stored for up to 6 months at various temperatures.

TABLE 2

Results from pH Analysis of L-Cys-HCl Historical Samples

| Additional Ingredients | Storage | TTP No. | D.O.M. | Appearance | pH |
|---|---|---|---|---|---|
| 2.6 mg/mL NaAC, 10 mg/mL Asc. Acid, 0.2 mg/mL EDTA, pH 2.2 | 23° C./5° C. 6 mo. | WFJ-C0002 | Jun. 4, 2008 | clr, no color, white ppt | 2.77 |
| 0.2 mg/mL EDTA, pH 2.2 | 23° C./5° C. 6 mo. | WFJ-C0002 | Jun. 5, 2008 | clr, no color, white ppt | 2.45 |
| 10 mg/mL Ascorbic Acid, pH 2.2 | 23° C./5° C. 6 mo. | WFJ-C0002 | Jun. 5, 2008 | clr, no color, no ppt | 2.55 |
| 2.6 mg/mL NaAC, 10 mg/mL Ascorbic Acid, pH 2.2 | 23° C./5° C. 6 mo. | WFJ-C0002 | Jun. 5, 2008 | clr, no color, no ppt | 2.44 |
| Ascorbic Acid, pH 2.2, Lot WFJC0003_2, 8 mL | −20° C. 5 mo. | WFJ-C0003 | Jul. 1, 2008 | clr, no color, no ppt | 2.20 |
| EDTA, pH 2.2, Lot WFJC0003_1, 8 mL | −20° C. 5 mo. | WFJ-C0003 | Jul. 1, 2008 | clr, no color, no ppt | 2.20 |
| Asc. Acid, NaAC, pH 2.2, Lot WFJC0003_5, 8 mL | −20° C. 5 mo. | WFJ-C0003 | Jul. 1, 2008 | clr, no color, no ppt | 2.22 |
| A A, NaAc, EDTA, pH 2.1, Lot WFJC0003_3, 8 mL | −20° C. 5 mo. | WFJ-C0003 | Jul. 1, 2008 | clr, no color, no ppt | 2.12 |
| 10 mg/mL Asc. Acid,, pH 2.2 | 23° C. 6 mo. | WFJ-C0002 | Jun. 5, 2008 | clr, no color, few particles | 2.55 |
| 2.6 mg/mL Acetate, 10 mg/mL Asc. Acid, 0.2 mg.mL EDTA | 23° C. 6 mo. | WFJ-C0002 | Jun. 4, 2008 | clr, no color, white ppt | 2.80 |
| WFJ-00017/GLP Fill, Nitrogen purged prior to fill. Lot WFJ-C0007_090308 | −20° C. 3 mo. | WFJ-C0017 | Sep. 3, 2008 | clr, no color, no ppt | 2.39 |

Mixing Experiments

Table 1 shows the results from mixing 1.0 mL of 3.6M Tris with L-Cys-HCl pH adjusted aliquots. The Tris was added to raise the pH of the L-Cys-HCl samples to a target pH range of 4.5 to 5.5. The results were plotted and are shown in FIG. 1. If the starting pH is above 2.1, the resulting pH after mixing will exceed the 4.5 to 5.5 target range. However, if the starting pH is 1.9 to 2.0, the mixed Tris+L-Cys-HCl samples are The WFJ-C0002 samples that had been stored at 22.5° C. for approximately 6 months had pH values ranging from 2.44 to 2.77, although a pH of 2.2 was recorded for these samples when first made. In some vials there was definite white precipitate.

The WFJ-C0003 samples that were stored at −20° C. for approximately 5 months had pH values ranging from 2.12 to 2.22, which matched the pH at the time of compounding.

There was no visible precipitate observed in these vials.

The WFJ-C00017 GLP Filled sample that was stored at −20° C. for approximately 3 months had essentially the same pH value (2.39) as when first made; nor was there any precipitate in this sample.

These data indicate that that pH is stable if the vials are frozen after compounding.

Temperature and pH Measurements

Figure 2A:
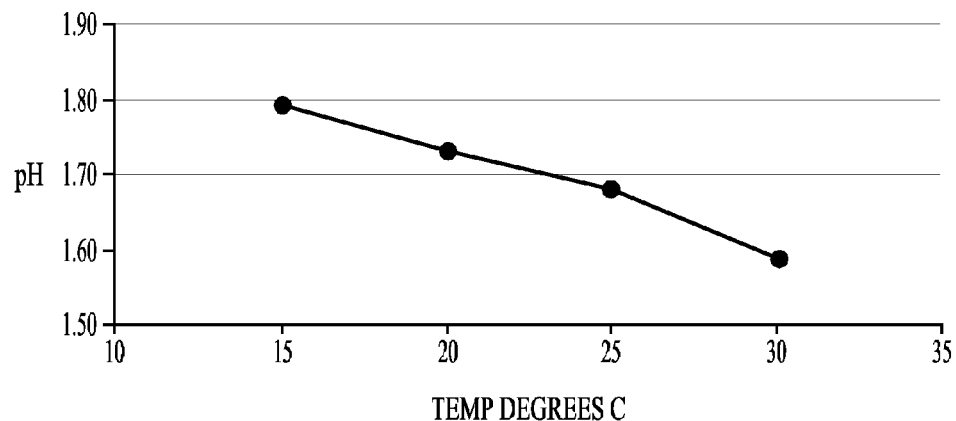
FIGS. 2A and 2B illustrate the effect of temperature on the pH of standard and L-Cys-HCl solutions. The effect of temperature on a pH standard (1.679) is shown in FIG. 2A while the effect of temperature on an L-Cys-HCl solution is shown in FIG. 2B.
Figure 2B:
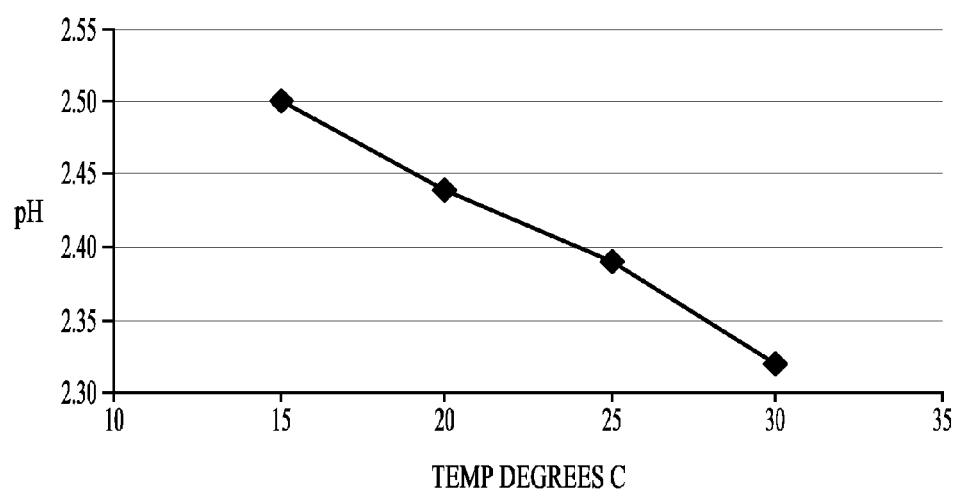

Results from changing the temperature and measuring pH using the 1.679 IUPAC reference Standard Solution and from analysis of L-Cys-HCl GLP Fill solution are shown in FIG. 2.

When temperature changes over a range of 15° C. to 30° C., the resulting change in pH of both solutions was about 0.20 pH units. These data indicate that the pH of L-Cys-HCl solutions can vary with temperature. Thus, it is advisable to monitor and control the temperature when measuring pH values of L-Cys-HCl solutions, especially if the tolerance for the L-Cys-HCl preparation is ±0.05 pH units.

Conclusions

A new preparation of L-Cys-HCl formulated at pH 1.95, with 225 mg/mL L-Cysteine HCl and 0.2 mg/mL $CaNa_2$ EDTA was prepared. The pH was stable as measured at 1.97 after 10 days of storage.

As demonstrated above, when L-Cys-HCl solutions having a pH ranging from 1.9 to 2.0, are mixed with 1.0 mL of 3.6M Tris, the resulting pH will be 4.5 to 5.5, which is a desirable pH for injection of cysteine. When the 3.6M Tris was mixed using a whole vial of L-Cysteine HCl, the resulting pH was 4.6 as observed in two separate preparations. The pH was stable for at least 8 hours after mixing whole vials and no particulates were observed.

A clear relationship between pH and temperature was demonstrated. In order to accurately maintain a pH tolerance of ±0.05 pH units, the temperature of samples and standards can be controlled and monitored, for example, using a circulating water bath.

Example 2

Cysteine Precipitates when Solutions are Exposed to Air

The Example shows that exposure of low pH cysteine solutions to air during neutralization leads to precipitation of the cysteine. In this Example, L-Cysteine Hydrochloride Monohydrate formulations were tested for formation of visual particulate matter after mixing with the Tris neutralizing agent.

Materials and Methods

The following supplies and equipment were employed:
1. Tris (hydroxymethyl)-aminomethane, 99.9%, Ultrapure grade, Lot 17120CH
2. L-Cysteine Hydrochloride Monohydrate, Sigma Aldrich, R&D Manufacturing Grade, Lot 087K0707611
3. Sodium Acetate Anhydrous, JT Baker, ACS Grade, Lot B31151
4. L-Ascorbic Acid, Sigma Aldrich, Ultra Grade, Lot 106K0053
5. EDTA Calcium disodium salt, hydrate, 98% pure, Aldrich Lot 01929 KH
6. Glacial Acetic Acid, Mallinckrodt, USP Grade, Lot E40005
7. 6N Sodium Hydroxide, ACS Grade, Ricca Chemicals Lot 4708124
8. Class A volumetric glassware
9. Mettler AT 201 analytical balance, equipment ID INS-C0910
10. Radiometer pH meter PHM 220, equipment ID, INS-C0751
11. Milli-Q water purification system, equipment ID INS-C1005
12. Fluke digital thermometer, equipment ID INS-C0739
13. Ultra pure nitrogen gas, number, UN1066
14. 0.22 micron PVDF filters, 500 mL receiver bottle, Millipore, SCGVU05RE, LotR7BN05327
15. Stirrer hot plate
16. Laminar flow hood, equipment ID, INS-C0318
17. Sterile 1 mL syringes and 18 gauge needles.

Preparation of 4M Tris pH 8.6±0.1

A 10% glacial Acetic Acid solution was prepared by mixing a ratio or 1 mL of glacial acetic acid per 9 mL of Milli-Q water and filtered through a 0.22 micron filter and deoxygenated with nitrogen gas sparging for at least one hour prior to use in mixing experiments as a neutralizing agent for the L-Cysteine Hydrochloride Monohydrate.

A 200-mL batch of 4M Tris buffer pH 8.6±0.1 was prepared by weighing 96.8 grams of Tris (FW 121.14) into a 200 mL glass beaker containing 10% glacial acetic acid. The solution was heated slightly until the solution was warm using on a hot plate while being stirred until all solid dissolved.

When the contents was completely dissolved and allowed to cool to room temperature the pH was adjusted to 8.6±0.1 with Glacial Acetic Acid. The solution was quantitatively transferred to a 200 mL volumetric flask and QS to mark with 10% glacial acetic acid and the final pH measured to ensure it remained within the target range. At the time of use, the TRIS solution was sparged with nitrogen for 30 to 60 minutes prior to use. The solution was stored at room temperature in the sterile filtered container.

Preparation of L-Cysteine Hydrochloride Monohydrate Solutions

Formulation 1, containing L-Cysteine Hydrochloride Monohydrate, 250 mg/mL, $CaNa_2EDTA$ at 0.2 mg/mL, pH 2.2 (Lot WFJC0003_1) was made as follows.

L-Cysteine Hydrochloride Monohydrate was prepared by weighing 125 grams of L-Cysteine Hydrochloride Monohydrate into a 500-mL glass beaker containing about 300 mL of deionized Milli Q water deoxygenated by nitrogen gas for at least 1 hour prior to use, and 100 milligrams of edatate calcium disodium (EDTA). As the L-Cysteine Hydrochloride Monohydrate dissolved, the solution became extremely cold so the solution was warmed on a hot plate with stirring until the solution reached room temperature and the contents were completely dissolved. The pH was then adjusted to 2.2±0.1 with 6.0N sodium hydroxide. The contents of the beaker were then quantitatively transferred to a 500 mL volumetric flask and degassed Milli-Q water was added to the mark. The solution was then sparged with nitrogen gas for about 30 minutes. After degassing, the solution was then filtered through a 0.22 micron PVDF filter and 8.0 mL aliquots were placed in clean 10 cc vials while in a laminar flow hood. The filled vials were sealed with 20 mm grey rubber stoppers, sealed by crimping with (blue) aluminum caps and labeled with the formulation components including the date of manufacturing (DOM). The appearance and pH were recorded after filtration and the samples stored at −20° C. until used for mixing studies.

Formulation 2, containing L-Cysteine Hydrochloride Monohydrate, 250 mg/mL, ascorbic acid at 10 mg/mL, pH 2.2 (Lot WFJC0003_2) was made as follows.

L-Cysteine Hydrochloride Monohydrate was prepared by weighing 125 grams of L-Cysteine Hydrochloride Monohydrate and 5 grams of ascorbic acid into a 500-mL glass beaker containing about 300 mL of deionized Milli Q water deoxygenated with nitrogen gas for at least 1 hour prior to use. As the L-Cysteine Hydrochloride Monohydrate dissolved, the solution became extremely cold so the solution was warmed on a hot plate with stirring until it reached room temperature and the contents were completely dissolved. The pH was then adjusted to 2.2±0.1 with 6.0N sodium hydroxide. The contents of the beaker were then quantitatively transferred to a 500 mL volumetric flask and degassed Milli-Q water was added to the mark. The solution was sparged with nitrogen gas for about 30 minutes. After degassing, the solution was filtered through a 0.22 micron PVDF filter and 8.0 mL aliquots were placed in clean 10 cc vials while in a laminar flow hood. The filled vials were sealed with 20 mm grey rubber stoppers crimped with (green) aluminum caps and labeled with the formulation components including the date of manufacturing. The appearance and pH were recorded after filtration and the samples were stored at −20° C. until used for mixing studies.

Formulation 3, containing L-Cysteine Hydrochloride Monohydrate at 250 mg/mL, ascorbic acid at 10 mg/mL, Sodium acetate at 2.6 mg/mL and CaNa$_2$EDTA at 0.2 mg/mL, pH 2.2 (Lot WFJC0003_3) was made as follows.

L-Cysteine Hydrochloride Monohydrate was prepared by weighing 125 grams of L-Cysteine Hydrochloride Monohydrate, 5 grams of ascorbic acid, 1.3 grams of sodium acetate and 100 milligrams of EDTA into a 500-mL glass beaker containing about 300 mL of deionized Milli Q water deoxygenated with nitrogen gas for at least 1 hour prior to use. As the L-Cysteine Hydrochloride Monohydrate dissolved, the solution became extremely cold so the solution was stirred on a hot plate until reaching room temperature and the contents were completely dissolved. The pH was adjusted to 2.2±0.1 with 6.0N sodium hydroxide. The contents of the beaker were quantitatively transferred to a 500 mL volumetric flask and degassed Milli-Q water was added to mark. The solution was sparged with nitrogen gas for about 30 minutes prior to filling into glass vials. After degassing, the solution was filtered through a 0.22 micron PVDF filter and 8.0 mL aliquots were placed in clean 10 cc vials while in a laminar flow hood. The filled vials were sealed with 20 mm grey rubber stoppers crimped with (orange) aluminum caps and labeled with the formulation components including the date of manufacturing. The appearance and pH were recorded after filtration and the samples were stored at −20° C. until used for mixing studies.

Formulation 4, containing L-Cysteine Hydrochloride Monohydrate at 216 mg/mL, pH 2.2 (Lot WFJC0003_4) was made as follows.

L-Cysteine Hydrochloride Monohydrate was prepared by weighing 125 grams of L-Cysteine Hydrochloride Monohydrate with about 400 mL of deoxygenated deionized Milli Q water by nitrogen gas for at least 1 hour prior to use.

As the L-Cysteine Hydrochloride Monohydrate dissolved, the solution became extremely cold so the solution was warmed on a hot plate until reaching room temperature and the contents were completely dissolved. The pH was then adjusted to 2.2±0.1 with 6.0N sodium hydroxide. The total volume of the solution was incorrectly adjusted to 580 mL (rather than 500 mL), yielding a concentration of 216 mg/mL for L-Cysteine Hydrochloride Monohydrate. The final solution was sparged with nitrogen gas for about 30 minutes prior to placing aliquots in glass vials. After degassing, the solution was filtered through a 0.22 micron PVDF filter and 8.0 mL aliquots were placed in clean 10 cc vials while in a laminar flow hood. The filled vials were sealed with 20 mm grey rubber stoppers crimped with (red) aluminum caps and labeled with the formulation components including the date of manufacturing. The appearance and pH were recorded after filtration and the samples were stored at −20° C. until used for mixing studies.

Formulation 5, containing L-Cysteine Hydrochloride Monohydrate at 250 mg/mL, ascorbic acid at 10 mg/mL and sodium acetate at 2.6 mg/mL pH 2.2 (Lot WFJC0003_5) was made as follows.

L-Cysteine Hydrochloride Monohydrate was prepared by weighing 125 grams of L-Cysteine Hydrochloride Monohydrate, 5 grams of ascorbic acid and 1.3 grams of sodium acetate into a 500-mL glass beaker containing about 300 mL of deionized Milli Q water deoxygenated with nitrogen gas for at least 1 hour prior to use.

As the L-Cysteine Hydrochloride Monohydrate dissolved, the solution became extremely cold so the solution was warmed on a hot plate with stirring until the solution reached room temperature and the contents were completely dissolved. The pH was then adjusted to 2.2±0.1 with 6.0N sodium hydroxide. The final solution was sparged with nitrogen gas for about 30 minutes prior to filling into glass vials. After degassing, the solution was then filtered through a 0.22 micron PVDF filter and filled with a repeat pipettor to a target volume of 8.0 mL into clean 10 cc vials in a laminar flow hood. The filled vials were sealed with 20 mm grey rubber stoppers crimped with (silver) aluminum caps and labeled appropriately with formulation components including the date of manufacturing. The appearance and pH were recorded after filtration and samples were stored at −20° C. until used for mixing studies.

Mixing Experiments

Two experiments were performed and observations made using only vials from Formulations 1, 2, 3 and 5. Formulation 4, containing L-Cysteine Hydrochloride Monohydrate alone at 216 mg/mL was not used for mixing studies since these vials contained a distinct white, insoluble precipitate after being thawed. In Experiment 1, TRIS was added by de-crimping the vials. In Experiment 2, TRIS was added by injecting through the stopper with de-crimping the vials.

In Experiment 1, one vial of L-Cysteine Hydrochloride Monohydrate was thawed, de-crimped and exposed to air. Various amounts of 4M TRIS, pH 8.6 solution were added methodically to determine the exact volume of TRIS that would obtain a target pH that ranged from 4.00 to 5.50. The 4M TRIS used was filtered through a 0.22 µm membrane and not sparged with nitrogen prior to use. The L-Cysteine Hydrochloride Monohydrate vials were exposed to air for an estimated 20 minutes while determining the exact TRIS volumes required to make the target pH. However, the headspace above each formulation was layered with nitrogen before re-crimping.

The vials were then observed over time for the formation of visible particles. Because particles appeared in all formulations several hours after mixing with neutralized with TRIS, a pilot study was performed to ascertain whether exposure to air might be responsible. An additional set of vials, each containing one of the formulations was prepared so that a determined volume of 4M TRIS could be added to achieve a target pH of 4.5 without exposing the formulations to air. Thus, these vials were not de-crimped and exposed to air. Instead, the 4M TRIS was added using a sterile 1 mL syringe and 18 gauge needle.

Based on the results from Experiment 1, Experiment 2 was performed where pre-determined volumes of 0.22 micron filtered 4M TRIS were added to Formulations 1, 2, 3 and 5 without opening or de-crimping the vials. To ensure minimal exposure to air the following three procedures were followed.

The TRIS was sparged for at least 1 hour with nitrogen prior to use and added to each sealed vial using a sterile 1 mL syringe with an 18 gauge needle. For Experiment 2, the target pH ranged from 3.50 to 5.50. The volume of 4M TRIS required to obtain a pH of 3.5 was determined by extrapolation of the data used to generate pH from 4.00 to 5.50 in Experiment 1. The mixed solutions were then left at room temperature and observed over a 90 hour period for the formation of visible particles. At the end of the observation period, the vials were opened and the final pH was measured. When pH was measured, one vial from each formulation was thawed and used as a control for determining the pH of the unmixed solution.

Results

Table 3 shows the volume (mL) for generating target pH values (3.5 to 5.5) for L-Cysteine Hydrochloride Monohydrate Formulations 1, 2, 3 and 5 by mixing in 4M TRIS pH 8.6. As described above, a cysteine solution at pH of 4.0-5.0 avoids venous irritation or trauma after intravenous administration. Hence, separate vials of each formulation were adjusted to a pH range of 3.50 to 5.50. For pH 4.50, two vials were set up as described above, one that was exposed to air and the other that was not exposed to air (labeled below with the asterisks * symbol).

TABLE 3

Volume (mL) of 4M TRIS pH 8.6 to Raise the pH of L-Cysteine Hydrochloride Monohydrate Formulations to Target pH Values

| Formulation Number | Target pH | | | | | |
|---|---|---|---|---|---|---|
| | 3.50 | 4.00 | 4.50* | 5.00 | 5.30 | 5.50 |
| 1 | 0.950 | 1.150 | 1.350 | 1.600 | 1.750 | 1.800 |
| 2 | 0.910 | 1.160 | 1.410 | 1.720 | 1.900 | 2.300 |
| 3 | 1.080 | 1.350 | 1.620 | 2.000 | 2.200 | 2.300 |
| 5 | 0.910 | 1.165 | 1.420 | 1.750 | 1.925 | 2.025 |

*The volumes cited for this target pH were added to an additional vial for each formulation using a sterile syringe and needle without de-crimping to minimize exposure to air.

The formulations were observed to ascertain when particulate matter appeared after mixing. The results are shown in Table 4, where TRIS was added to the pH 4.50* vials without exposing the cysteines solution to air.

TABLE 4

Approximate Time (Hours) Elapsed Until Particulate Matter Was First Observed in Experiment 1

| Formulation Number | Target pH | | | | | |
|---|---|---|---|---|---|---|
| | 4.00 | 4.50 | 4.50* | 5.00 | 5.30 | 5.50 |
| 1 | 1 | 1 | 47 | 1 | 1 | 1 |
| 2 | 1 | 1 | 47 | 1 | 1 | 1 |
| 3 | 1 | 1 | 18 | 1 | 1 | 1 |
| 5 | 1 | 1 | 37 | 1 | 1 | 1 |

*The volumes cited for this target pH were added to an additional vial for each formulation using a sterile syringe and needle without de-crimping to minimize exposure to air.

As illustrated in Table 4, there was a dramatic difference in the vials exposed to air versus vials not exposed to air with regards to the when particulates were first observed. Results from this experiment indicated that the procedures to be used in Experiment 2 should avoid exposure of the cysteine formulations to air, to increase the time before particles are formed.

Table 5 shows the pH observed after the observation period.

TABLE 5

Observed pH at the End of Experiment 2
(Reference NB 08-1381 Attachment F)

| Target pH | Form. 1 | Form. 2 | Form. 3 | Form. 5 |
|---|---|---|---|---|
| Non-Mixed control | 2.2 | 2.3 | 2.1 | 2.2 |
| 3.5 | 3.5 | 3.4 | 3.4 | 3.4 |
| 4.0 | 4.0 | 4.1 | 4.1 | 4.0 |
| 4.5 | 4.6 | 4.5 | 4.5 | 4.5 |
| 5.0 | 5.0 | 4.9 | 5.0 | 4.9 |
| 5.3 | 5.3 | 5.3 | 5.3 | 5.2 |
| 5.5 | 5.4 | 5.4 | 5.5 | 5.4 |

All values observed were within 0.1 unit of the target pH.

Also, it should be noted that care must be taken with electrodes to measure pH of the L-Cysteine Hydrochloride Monohydrate solutions that contain silver chloride (AgCl) as a reference filling solution. Precipitate was observed to form that impeded electrode performance. A simple mixing experiment using the AgCl and L-Cysteine Hydrochloride Monohydrate solution in a test tube results in immediate formation of a white precipitate. Proper care of the electrode when exposed to thiol compounds is necessary to get reproducible pH values. Alternatively, an electrode cam be used that does not contain AgCl as a reference filling solution, for example, a Calomel Combined pH Electrode.

The time until particles were first observed in the formulations of Experiment 2 are shown in Table 6.

TABLE 6

Approximate Time (Hours) Elapsed Until Particulate Matter Was First Observed in Experiment 2

| Target pH | Form. 1 | Form. 2 | Form. 3 | Form. 5 |
|---|---|---|---|---|
| 3.5 | None | None | 37 | None |
| 4.0 | None | None | 25 | None |
| 4.5 | 84 | None | 25 | 82 |
| 5.0 | 61 | 21 | 20 | 29 |
| 5.3 | 38 | 12 | 20 | 11 |
| 5.5 | 38 | 8 | 16 | 11 |

Results from Experiment 2 show that by reducing or eliminating the exposure of cysteine mixed with TRIS to air increases the time observed for particle formation.

Figure 3:
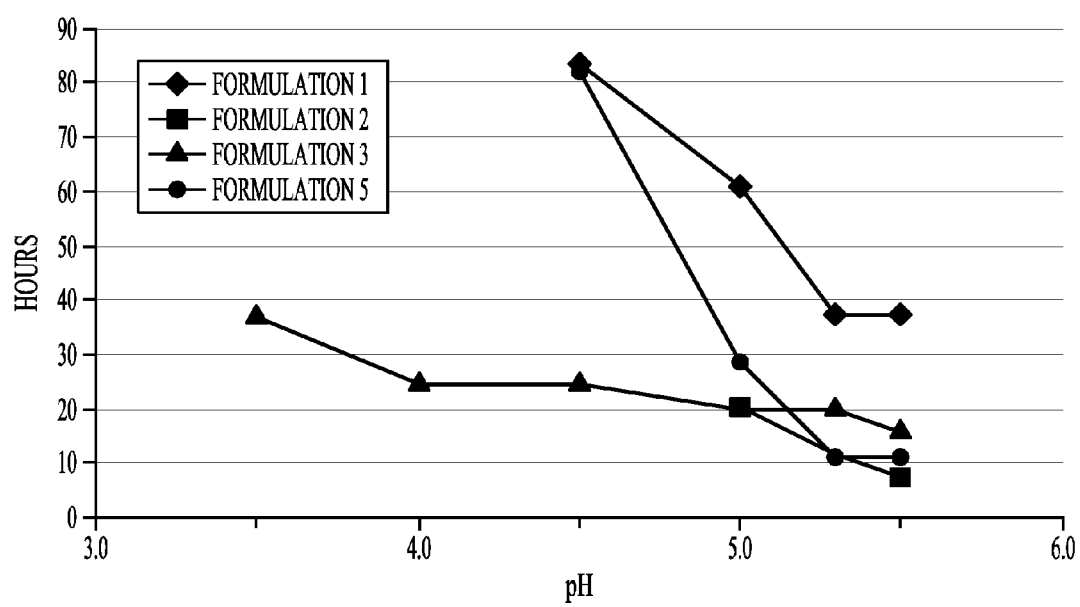
FIG. 3 shows the time in hours when precipitation was observed in various L-Cys-HCl solutions (formulations 1, 2, 3 and 5) as a function of pH. Formulations 1, 3 and 5 were particle free for at least 24 hours at a pH of about 5.

As illustrated by Experiment 1, the air exposure during brief pH adjustments and mixing occurring for approximately 20 minutes led to particle formation. The particles observed were most likely Cystine as opposed to contaminating particles introduced by sample handling. Experiment 2 shows that Formulations 1, 3 and 5 were particle free for at least 24 hours at a pH of about 5. Exposure of the solutions to air should be minimized or eliminated to control the formation of particles after mixing. Across the pH values monitored for visual particulate matter formation, Formulations 1 and 5 gave the longest times before particulate matter was observed (see FIG. 3).

EXAMPLE 3

Preliminary Cysteine Toxicology Studies

This Example describes toxicology studies performed using FDA guidelines.

The toxicology of L-cysteine was examined in rats, dogs and monkeys. Monkeys had been routinely used for several years to evaluate various neuromuscular blocking agents, with reversal of the neuromuscular blockade using various cysteine doses. Conscious rats received L-cysteine bolus injections of 750 mg/kg intravenously while conscious dogs received bolus injections of 400 mg/kg intravenously. Anesthetized dogs received 200 mg/kg by bolus intravenous injection to reverse the neuromuscular blocking agent CW002, which is the R-trans, R-trans isomer of the compound shown below.

The anesthetized dogs were awakened then sacrificed 2 days or 2 weeks later.

No animals exhibited clinical, biochemical, or histological evidence of organ toxicity. There was no indication of toxic effects in monkey colony that received multiple bolus doses of L-cysteine over a period of 3 years.

These results indicate that L-cysteine does not give rise to toxicity at the doses employed.

EXAMPLE 4

Comparative Pharmacology of L- and D-Cysteine for Reversal of a Neuromuscular Blocking Agent This Example shows that D-cysteine is effective for reversal of neuromuscular blocking agents and at high doses (e.g., 100 mg/kg) elicits a smaller rise in mean arterial pressure than L-cysteine.

Previous work by the inventors has established the efficacy and potency of L-cysteine for rapidly reversing the neuromuscular blockade produced by CW002. These investigations revealed that 100 mg/kg L-cysteine (2-3 fold higher than the dose projected for clinical use and no more effective than 50 mg/kg) produced a modest increase in blood pressure mediated in part by stimulation of the central nervous system. L-cysteine is produced endogenously and crosses the blood-brain barrier largely via a specific amino acid transporter. Thus, L-cysteine may contribute to central nervous stimulation following injection of 100 mg/kg. The D isomer of cysteine is not normally found in substantial quantities within the body, and is not a substrate for metabolic processes involving L-cysteine such as glutathione synthesis. In addition, D-cysteine is not a major substrate for the amino acid transporters which are L-isomer specific. Whether D-cysteine has similar potency to L-cysteine for reversal of CW002 was previously not known. Accordingly, the Example describes experiments designed to evaluate whether the two isomers differ in regards to adduction of the CW002 molecule and reversal of neuromuscular blockades.

Methods

The neuromuscular blocking agent employed for these studies was the R-trans, R-trans isomer of the following structure (called CW002):

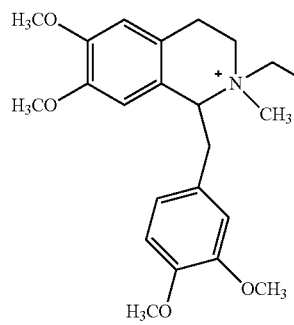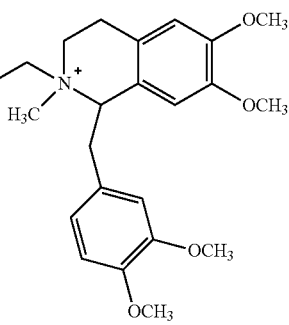

Three anesthetized male beagles received CW002. After 1 minute and complete loss of muscle twitch, D-cysteine was administered at dosages of 10, 20, 50 or 100 mg/kg. Each dose was given as a single experiment separated from other experiments by at least 7 days. The rate and time to complete recovery of muscle twitch in each animal was determined. These data were compared to the rate of spontaneous recovery and duration of the same dose of CW002 given in a previous study, and how these variables were altered by 10, 20, 50 or 100 mg/kg L-cysteine (see, e.g., Sunaga et al., Anesthesiology 112: 900-909 (2010)).

In addition to the 100 mg/kg dose of D-cysteine used for CW002 reversal, each of the 3 animals also received L-cysteine 70-90 minutes after recovery of muscle twitch. Arterial blood pressure and heart rate were continuously measured before and after each injection for comparison of the magnitude for each response. Baseline and peak response data for both isomers were compared by analysis of variance for repeated measures using SigmaStat. A p value<0.05 was considered significant.

Results

Figure 4A:
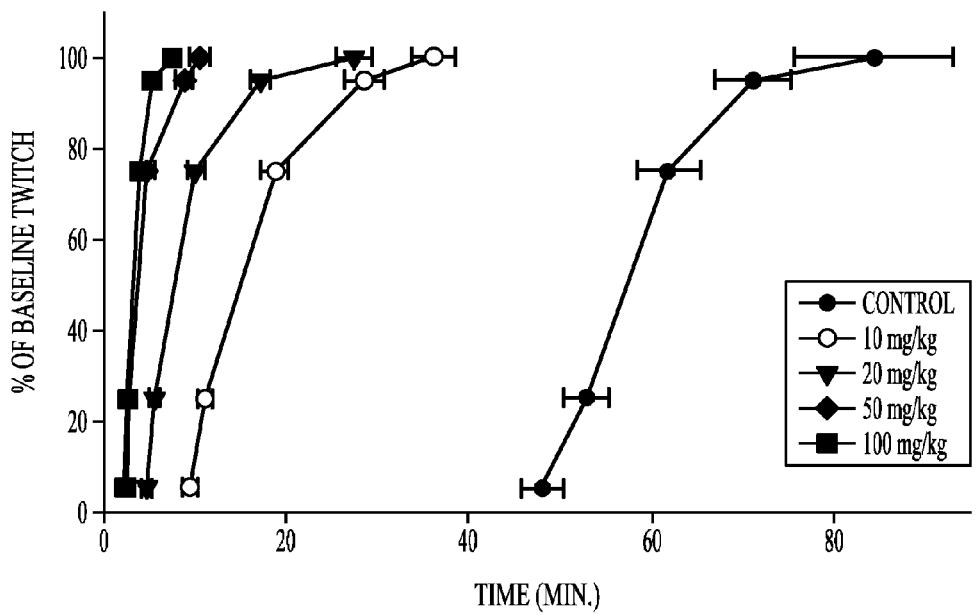
FIGS. 4A and 4B depict the time in minutes to 25, 75, 95 and 100% recovery of muscle twitch following 0.08 mg/kg CW002 for L-cysteine (FIG. 4A, n=6, data from previously published report), and D-cysteine (FIG. 4B, n=3).
Figure 4B:
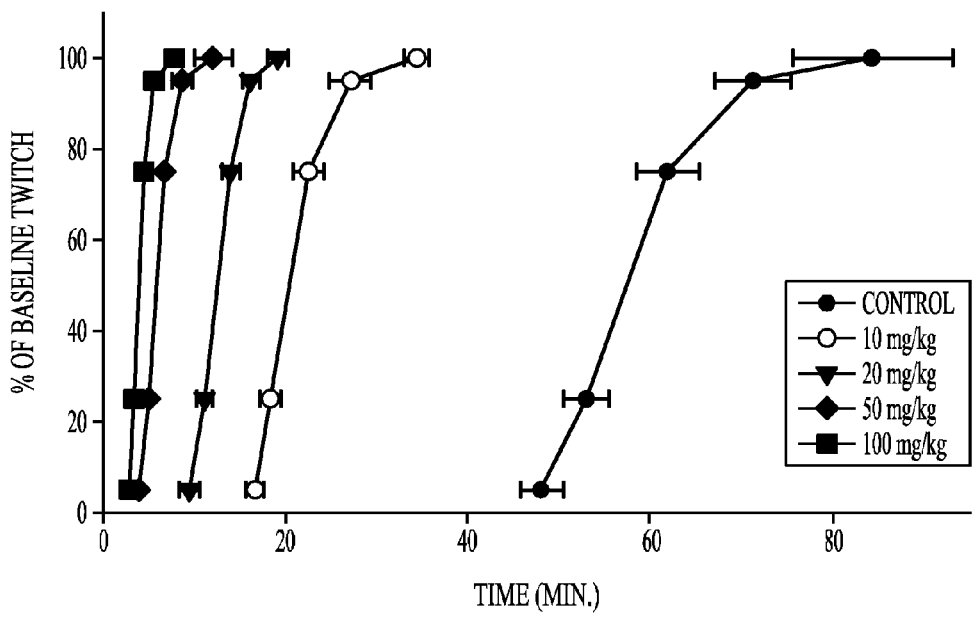

FIG. 4 depicts the time to 25, 75, 95 and 100% recovery of muscle twitch following 0.08 mg/kg CW002 for both L-cysteine (bottom panel, n=6, data from previously published report), and D-cysteine (top panel, n=3). Due to the small sample size for the D-cysteine group and the fact that data are not repeated measures from the same animals, low statistical power precludes precise comparison. Nonetheless, similarities between the recovery plots are clear.

Figure 5A:
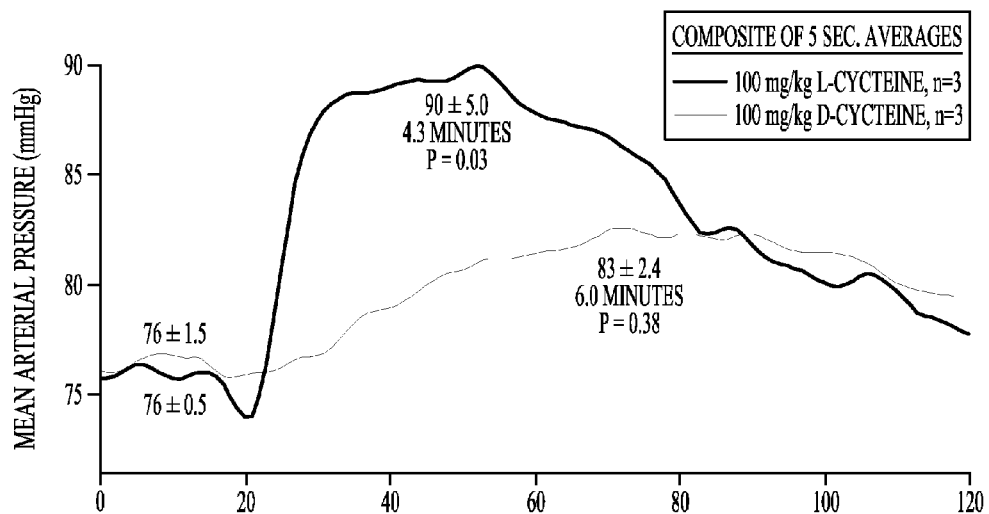
FIGS. 5A and 5B depict the mean arterial blood pressure (mAP.
Figure 5B:
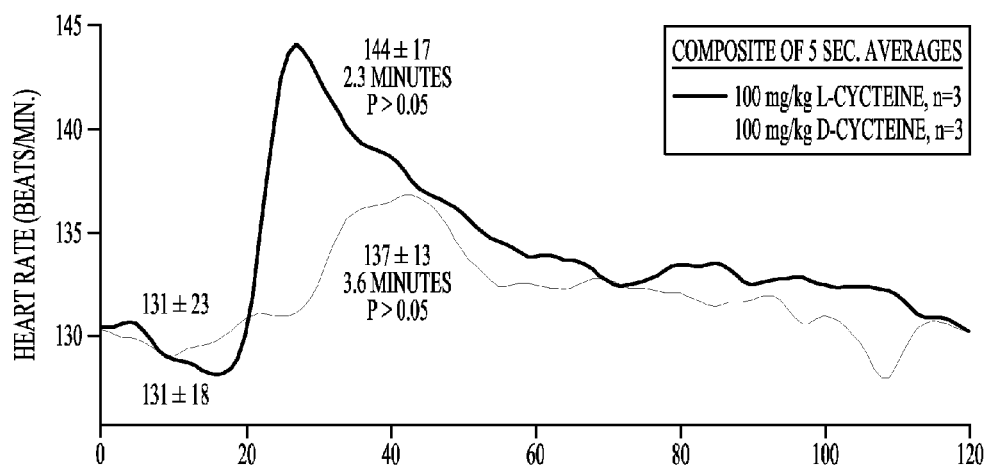

FIG. 5 depicts the mean arterial blood pressure (mAP) and heart rate (HR) responses to both D and L-cysteine in the same animals. Tracings represent the composite of 5 second averages for each animal beginning at the time of cysteine injection. Numerical data (mean±standard error) for variables at the time of injection (baseline) and peak response are shown, with the p value for the comparison. There was no difference between baseline mAP values for D and L-cysteine, but L-cysteine produced a two-fold higher rise in mAP relative to the D isomer. The peak response to L-cysteine also tended to occur earlier than that for D-cysteine, and was preceded by a small, transient depressor response. The increase in mAP seen after D-cysteine (7 mmHg, on average) was not significant. Similarly, following L-cysteine there was a transient fall followed by a rise in HR. Again, the change in HR following D-cysteine was roughly half that evident for L, and exhibited a slower onset. However, for neither D nor L-cysteine was the trend toward increased HR significant.

These data indicate that D-cysteine is effective for reversal of CW002 within a similar dose range to that previously described for L-cysteine, i.e. 30-50 mg/kg. At 100 mg/kg, D-cysteine elicits less of a rise in mean arterial pressure than L-cysteine, consistent with the probability of less entry into the central nervous system.

Embodiments of the Invention: The following statements describe certain aspects of the invention.

1. A method of making a cysteine solution for physiological administration that comprises:
   a. obtaining an aqueous solution of cysteine with a pH of about 1.80 to about 2.20; and
   b. mixing the aqueous solution of cysteine with a buffering solution to generate a cysteine solution for physiological administration that has a pH of about 4.5 to about 5.5, wherein oxygen is substantially removed from the aqueous solution of cysteine, the buffering solution and/or cysteine solution for physiological administration.
2. The method of statement 1, wherein the aqueous solution of cysteine has a pH of about 1.90 to about 2.00.
3. The method of statement 1 or 2, wherein the aqueous solution of cysteine comprises water or physiological saline.
4. The method of any of statements 1-3, wherein the buffering solution comprises a weak base.
5. The method of any of statements 1-4, wherein the buffering solution comprises tris(hydroxymethyl)methylamine (Tris), N,N-bis(2-hydroxyethyl)glycine (Bicine), N-tris(hydroxymethyl)methylglycine (Tricine), 4-2-hydroxyethyl-1-piperazineethanesulfonate (HEPES), {[tris(hydroxymethyl)methyl]amino}ethanesulfonate (TES), 3-(N-morpholino)propanesulfonate (MOPS), piperazine-N,N'-bis(2-ethanesulfonate (PIPES), 2-(N-morpholino)ethanesulfonate (MES) or combinations thereof.
6. The method of any of statements 1-5, wherein the cysteine solution for physiological administration has a cysteine concentration of 100 to 300 mg/ml.
7. The method of any of statements 1-5, wherein the cysteine solution for physiological administration has a cysteine concentration of 150-250 mg/ml.
8. The method of any of statements 1-7, wherein the aqueous solution of cysteine further comprises glutathione.
9. The method of statement 8, wherein the glutathione is present at a concentration of 100 to 200 mg/ml.
10. The method any of statements 1-9, wherein the aqueous solution of cysteine with a pH of 1.80 to about 2.20 further comprises a bacteriostatic agent, chelating agent, antioxidant or a combination thereof.
11. The method of statement 10, wherein the antioxidant is a vitamin, cofactor and combinations thereof.
12. The method of statement 10, wherein the antioxidant is ascorbic acid, vitamin A, vitamin E, coenzyme Q10, a flavonoid and combinations thereof.

13. The method of statement 10, wherein the chelating agent is citric acid, dicarboxymethylglutamic acid, ethylenediaminedisuccinic acid (EDDS), ethylenediaminetetraacetic acid (EDTA), hepta sodium salt of diethylene triamine penta (methylene phosphonic acid) (DTPMP.Na$_7$), malic acid, nitrilotriacetic acid (NTA), methionine, oxalic acid, phosphoric acid, polar amino acids (e.g., arginine, asparagine, aspartic acid, glutamic acid, glutamine, lysine, and ornithine), siderophores (e.g., Desferrioxamine B), succinic acid and combinations thereof.

14. A method of making a stable cysteine solution that can be stored prior to physiological administration, where the method involves:
    a. removing oxygen from a volume of physiological saline or water;
    b. adding sufficient cysteine to the physiological saline or water to generate a 150-250 mg/ml cysteine solution;
    c. adjusting the pH of the 150-250 mg/ml cysteine solution to a pH of about 1.90 to about 2.00 to generate a cysteine solution with a pH of about 1.90 to about 2.00;
    d. sparging the cysteine solution with the pH of about 1.90 to about 2.00 with non-oxygen containing gas to generate a deoxygenated cysteine solution;
    e. dispensing the deoxygenated cysteine solution into a container and sealing the container,
       to thereby make the stable cysteine solution that can be stored prior to physiological administration.

15. The method of statement 14, wherein the stable cysteine solution can be stored for up to about 1 year without significant precipitation or dimerization of the cysteine.

16. The method of statement 15, wherein the stable cysteine is stored frozen.

17. The method of any of statements 14-16, further comprising adjustment of the cysteine solution pH to about 4.4 to about 5.5.

18. The method of statement 17, wherein the adjustment comprises:
    f. adding a buffering solution to the stable cysteine solution to adjust the pH to about 4.4 to about 5.5 without exposing the stable cysteine solution to significant oxygen;
    g. mixing the buffering solution into the stable cysteine solution to generate a cysteine solution for physiological administration that has a pH of about 4.5 to about 5.5, wherein the mixing is performed without substantial exposure of the stable cysteine solution or the buffering solution to oxygen.

19. The method of statement 18, wherein oxygen has been substantially removed from the buffering solution.

20. A kit comprising:
    a. a first container with a stable solution of cysteine that has a pH of about 1.8 to about 2.1;
    b. a second container with a buffering solution for raising the pH of the stable solution of cysteine; and
    c. instructions for storing the kit, for raising the pH of the stable solution of cysteine to an appropriate pH and/or for administering the physiological solution of cysteine to reverse a neuromuscular blockade.

21. The kit of statement 20, further comprising one or more syringes and needles for transferring an appropriate amount of the buffering solution to the stable solution of cysteine and/or administering the physiological solution of cysteine to a patient.

22. The kit of statement 20 or 21, further comprising a third container that contains a neuromuscular blocking agent, wherein a neuromuscular blockade generated in a subject by the neuromuscular blocking agent can be reversed by cysteine.

23. The kit of any of statements 20-22, wherein the oxygen has been substantially removed from the first container and/or the second container.

24. The kit of any of statements 20-23, wherein the stable solution of cysteine is made by the method of any of statements 14-19.

25. A method of reversing a neuromuscular blockade in a patient to whom a cysteine-reversible neuromuscular blockade agent has been administered, comprising administering an effective amount of a physiological solution of cysteine to the patient, wherein the physiological solution of cysteine is made by a method comprising:
    a. removing oxygen from a volume of physiological saline or water;
    b. adding sufficient cysteine to the physiological saline or water to generate a 150-250 mg/ml cysteine solution;
    c. adjusting the pH of the 150-250 mg/ml cysteine solution to a pH of about 1.90 to about 2.00 to generate a cysteine solution with a pH of about 1.90 to about 2.00;
    d. sparging the cysteine solution with the pH of about 1.90 to about 2.00 with non-oxygen containing gas to generate a deoxygenated cysteine solution;
    e. dispensing the deoxygenated cysteine solution into a container and sealing the container to thereby make the stable cysteine solution that can be stored prior to physiological administration;
    f. adding a buffering solution to the stable cysteine solution to adjust the pH to about 4.4 to about 5.5 without exposing the stable cysteine solution to significant oxygen; and
    g. mixing the buffering solution into the stable cysteine solution to generate a physiological solution of cysteine that has a pH of about 4.5 to about 5.5, wherein the mixing is performed without substantial exposure of the stable cysteine solution or the buffering solution to oxygen.

26. The method of statement 25, wherein oxygen has been substantially removed from the buffering solution.

27. A method of making a stable cysteine solution that can be stored prior to physiological administration, where the method involves:
    a. removing oxygen from a volume of physiological saline or water;
    b. adding sufficient cysteine to the physiological saline or water to generate a 150-250 mg/ml cysteine solution;
    c. adjusting the pH of the 150-250 mg/ml cysteine solution to a pH of about 1.90 to about 2.00 to generate a cysteine solution with a pH of about 1.90 to about 2.00;
    d. sparging the cysteine solution with the pH of about 1.90 to about 2.00 with non-oxygen containing gas to generate a deoxygenated cysteine solution;
    e. dispensing the deoxygenated cysteine solution into a container and sealing the container,
       to thereby make the stable cysteine solution that can be stored prior to physiological administration.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method of reversing a neuromuscular blockade in a patient to whom a cysteine-reversible neuromuscular blockade agent has been administered, comprising administering an effective amount of a physiological solution comprising D-cysteine substantially free of L-cysteine to the patient.

2. A method of reversing a neuromuscular blockade in a patient to whom a cysteine-reversible neuromuscular blockade agent has been administered, comprising administering an effective amount of a physiological solution of cysteine substantially free of L-cysteine to the patient, wherein the physiological solution of cysteine has been made by a method comprising:
   adding NaOH and/or a buffering solution to cysteine HCl to generate a 150-250 mg/ml cysteine solution,
   wherein the solution is a physiological solution in a volume suitable for intravenous administration over a period of time of about 2 seconds to about 60 seconds.

3. The method of claim 2, wherein oxygen has been substantially removed from the NaOH or buffering solution.

4. A method of making a cysteine solution for physiological administration, where the method involves:
   adding NaOH and/or a buffering solution to cysteine HCl to generate a 150-250 mg/ml cysteine solution,
   wherein the solution is a physiological solution in a volume suitable for intravenous administration over a period of time of about 2 seconds to about 60 seconds.

5. The method of claim 2, wherein the cysteine is D-cysteine.

6. The method of claim 1, wherein the cysteine is D-cysteine.

* * * * *

UNITED STATES PATENT AND TRADEMARK OFFICE
CERTIFICATE OF CORRECTION

PATENT NO. : 9,220,700 B2  
APPLICATION NO. : 13/391154  
DATED : December 29, 2015  
INVENTOR(S) : Savarese et al.

Page 1 of 1

It is certified that error appears in the above-identified patent and that said Letters Patent is hereby corrected as shown below:

Title page

Item (30), in "Foreign Application Priority Data", in column 1, line 1,
after "PCT/US2010/000796", insert --¶Aug. 18, 2010 (WO) ............. PCT/US2010/045907--.

On page 3, in column 1, item (56), under "Other Publications", line 66, delete
"i-2-oxothiazolidne-4-carboxylate" and insert --i-2-oxothiazolidine-4-carboxylate--, therefor.

Signed and Sealed this
Twenty-eighth Day of June, 2016

Michelle K. Lee
*Director of the United States Patent and Trademark Office*